United States Patent
Stamler et al.

(10) Patent No.: US 10,959,996 B2
(45) Date of Patent: Mar. 30, 2021

(54) METHODS FOR THE TREATMENT OF ABNORMAL INVOLUNTARY MOVEMENT DISORDERS

(71) Applicant: Auspex Pharmaceuticals, Inc., Parsippany, NJ (US)

(72) Inventors: David Stamler, Menlo Park, CA (US); Michael Fangching Huang, Ladera Ranch, CA (US)

(73) Assignee: AUSPEX PHARMACEUTICALS, INC., North Wales, PA (US)

( * ) Notice: Subject to any disclaimer, the term of this patent is extended or adjusted under 35 U.S.C. 154(b) by 0 days.

(21) Appl. No.: 16/040,012

(22) Filed: Jul. 19, 2018

(65) Prior Publication Data

US 2018/0318281 A1 Nov. 8, 2018

Related U.S. Application Data

(63) Continuation of application No. 15/063,068, filed on Mar. 7, 2016, now abandoned.

(60) Provisional application No. 62/180,012, filed on Jun. 15, 2015, provisional application No. 62/175,112, (Continued)

(51) Int. Cl.
*A61P 25/14* (2006.01)
*A61K 9/20* (2006.01)
*A61K 31/4375* (2006.01)
*A61K 31/4745* (2006.01)
*A61K 45/06* (2006.01)
*A61K 31/473* (2006.01)

(52) U.S. Cl.
CPC .............. *A61K 31/473* (2013.01); *A61K 9/20* (2013.01); *A61K 9/2013* (2013.01); *A61K 9/2018* (2013.01); *A61K 9/2027* (2013.01); *A61K 9/2054* (2013.01); *A61K 31/4375* (2013.01); *A61K 31/4745* (2013.01); *A61K 45/06* (2013.01); *A61P 25/14* (2018.01)

(58) Field of Classification Search
None
See application file for complete search history.

(56) References Cited

U.S. PATENT DOCUMENTS

| 2,830,993 A | 4/1958 | Brossi et al. |
| 3,045,021 A | 9/1959 | Brossi |
| 8,039,627 B2 | 10/2011 | Gano |

(Continued)

FOREIGN PATENT DOCUMENTS

| EP | 1716145 | 11/2006 |
| GB | 2410947 A | 8/2005 |

(Continued)

OTHER PUBLICATIONS

Frank (Tetrabenazine as anti-chorea therapy in Huntington Disease: an open-label continuation study. Huntington Study Group/TETRA-HD Investigators, BMC Neurology, 2009, 9(62), pp. 1-10). (Year: 2009).*

(Continued)

*Primary Examiner* — Savitha M Rao
*Assistant Examiner* — Andrew P Lee
(74) *Attorney, Agent, or Firm* — BakerHostetler

(57) ABSTRACT

Disclosed herein are new dosage regimens for deuterium-substituted benzoquinoline compounds, and methods for the treatment of abnormal muscular activity, movement disorders, and related conditions.

40 Claims, 11 Drawing Sheets

Related U.S. Application Data filed on Jun. 12, 2015, provisional application No. 62/129,616, filed on Mar. 6, 2015.

(56) References Cited

U.S. PATENT DOCUMENTS

| | | | |
|---|---|---|---|
| 8,524,733 | B2 | 9/2013 | Gant et al. |
| 2010/0130480 | A1 | 5/2010 | Gant et al. |
| 2011/0046236 | A1 | 2/2011 | Czarnik et al. |
| 2012/0003330 | A1 | 1/2012 | Gant et al. |
| 2013/0197031 | A1 | 8/2013 | Sonesson |
| 2014/0336386 | A1* | 11/2014 | Sommer ............... A61K 9/0065 546/95 |

FOREIGN PATENT DOCUMENTS

| | | |
|---|---|---|
| JP | 2012-503010 A | 2/2012 |
| JP | 2013-501810 A | 1/2013 |
| JP | 2013-502227 A | 1/2013 |
| JP | 2013-536825 A | 9/2013 |
| WO | 2005/077946 | 8/2005 |
| WO | 2007/130365 | 11/2007 |
| WO | 2008/058261 | 5/2008 |
| WO | 2010/044981 A3 | 6/2010 |
| WO | 2011/019956 A2 | 2/2011 |
| WO | 2011/153157 | 12/2011 |
| WO | 2014/047167 A1 | 3/2014 |
| WO | 2014/120654 A1 | 8/2014 |
| WO | 2015/077520 | 11/2014 |

OTHER PUBLICATIONS

Teva, First Time Use of SD-809 in Huntington Disease (First-HD), 2013, https://clinicaltrials.gov/ct2/show/study/NCT01795859 (Year: 2013).*
Videnovic, Treatment of Huntington Disease, Current Treatment Options in Neurology, 2013, 15, pp. 424-438. (Year: 2013).*
Chen, Tetrabenazine for the Treatment of Hyperkinetic Movement Disorders: A Review of the Literature, 2012, Clinical Therapeutics, 34(7), pp. 1487-1504 (Year: 2012).*
Xenazine Label Highlights of Prescribing Information, 2015.
Weyler et al. "Purification and Properties of Mitochondrial Monoamine Oxidase type A From Human Placenta" (J Biol Chem. 1985, 260, 13199-13207).
Venuto, Pharmacologic Approaches to the Treatment of Huntington's Disease, Movement Disorders, 2012, 27(1), pp. 31-42.
Uebelhack et al. "Inhibition of Platelet MAO-B by Kava Pyrone-Enriched Extract from Piper Methysticum Forster (Kava-Kava)", (Pharmacopsychiatry, 1998, 31, 187-192).
Sung et al., "Physician Perceptions of Unmet Medical Needs in Huntington Disease in the United States", Presented by Academy of Managed Care Pharmacy Nexus, Dallas, Texas, Oct. 16-19, 2017.
Schwartz et al., "Metabolic Studies of Tetrabenazine, a Psychotropic Drug in Animals and Man" Biochem. Pharmacol., 1966, 15, 645-655.
Savani et a., Neurology 2007, 68(10) 797.
Roberts et al., Journal of Chromatography, Biomedical Applications, 1981, 226(1), 175-182.
Rishel et al., J. Org. Chem, 209, 74, 4001-4004.
Popp et al., "Synthesis of Potential Antineplastic Agents XXVI: 1,3,4,6,7, 11 b-Hexahydro-9, 10-dimethoxy-2H-benzo[a] 2-quinolizinone Derivatives" J Pharm. Sci., 1978, 67(6), 871-873.
NDA 21-894 Xenazine® (tetrabenazine), Risk Evaluation and Mitigation Strategy (REMS), Valeant Pharmaceuticals North America LLC, Aug. 2013.
Mehvar et al., Drug Metabolism and Disposition, 1987, 15(2), 250-255.
Li et al. "Simultaneously Quantifying Parent Drugs and Screening for Metabolites in Plasma Pharmacokinetic Samples using Selected Reaction Monitoring Information—Dependent Acquisition on a QTrap Instrument" Rapid Communications in Mass Spectrometry 2005, 19, 1943-1950.
Lee et al., "In Vitro and in Vivo Studies of Benzisoquinoline Ligands for the Brain Synaptic Vesicle Monoamine Transporter" J Med Chem., 1996, (39), 191-196.
Ko et al, "In vitro inhibition of the cytochrome P450 (CYP450) system by the antiplatelet drug ticlopidine: potent effect on CYP2C19 and CYP2D6", British Journal of Clinical Pharmacology, 2000, 49, 343-351.
Kilbourn et al., Chirality, 1997, (9), 59-62.
Kenney et al., Expert Review of Neurotherapeutics, 2006, 6(1), 7-17.
Kenney et al., "Long-Term Tolerability of Tetrabenazine in the Treatment of Hyperkinetic Movement Disorders", Movement Disorders, vol. 22, No. 2, 2007.
Jindal, et al., Journal of Chromatography, Biomedical Applications, 1989, 493(2), 392-397.
Jankovic et al., "Tetrabenazine Therapy of Dystonia, Chorea, Tics, and other Dyskinesias", Neurology, 38, pp. 391-394, Mar. 1988.
Jankovic et al., "Long-Term Effects of Tetrabenazine in Hyperkinetic Movement Disorders" American Academy of Neurology, pp. 358-362, Feb. 1997.
Ivanov et al., "Application of Hexamethylenetetramine in a Pictet-Spengler Type Reaction for Synthesis Ofisoquinoline Derivatives Heterocycles" May 2001, 55(8), 1569-1572.
Ho, Health-Related Quality of Life in Huntington's Disease: Which Factors Matter Most?, Movement Disorders, 2009, 24(4), pp. 574-578.
Hauser et al., "Long-Term Treatment with Deutetrabenazine is Associated With Continued Improvement in Tardive Dyskinesia (TD): Results from an Open-Labeled Extension Study" Presented at the American Academy of Neurology 2018 Annual Meeting, Los Angeles, California, Apr. 21-27, 2018.
Gharabawi, Abnormal Involuntary Movement Scale (AIMS) and xtrapyramidal Symptom Rating Scale (ESRS): Cross-scale comparison in assessing tardive dyskinesia, Schizophrenia Research, 2005, 77, pp. 119-128.
Gardner, Modern antipsychotic drugs: a critical overview, CMAJ, 2005, 172 (13), pp. 1703-1711.
Frank, Tetrabenazine as anti-chorea therapy in Huntington Disease: an open-label continuation study. Huntington Study Group/TETRA-HD Investigators, BMC Neurology, 2009, 9(62), pp. 1-10.
DaSilva et al., "Synthesis of [I IC]tetrabenazine, a Vesicular Monoamine Uptake Inhibitor, for PET Imaging Studies" Appl. Radiat. Isot., 1993, 44(4), 673-676.
Cohen, et al., "Clinical Assessment of Tourette Syndrome and Tic Disorders", Neurosc. Biobehav. Rev., 2013, 37(6), pp. 997-1007.
Clinical Trials.gov. Reducing Involuntary Movements in Tardive Dyskinesia (RIM-TD), https://clincialtrials.gov/ct2/show/CNT02198794?term=SD809&rank=4 2014.
Clinical Trials.gov, First Time use SD-809 in Huntington Disease (First-HD), https://clinicaltrials.gov/ct2/show/study/NCT01795859?term=SD809&rank=1 2013.
Clinical Trials.gov, Alternatives for Reducing Chorea in HD (ARC-HD), https://clinicaltrials.gov/ct2/show/NCT01897896?term=SD809&rank=3 2013.
Clinical Trials.gov, Aim to Reduce Movements in Tardive Dyskinesia (ARM-TD), https://clinicaltrials.gov/ct2/show/NCT02195700?term=SD809&rank=5 2014.
Clinical Trials.gov, Addressing involuntary movements in Tardive Dyskinesia (AIM-TD), https://clinicaltrials.gov/ct2/show/NCT02291861?term=SD809&rank=6 2014.
Clinical Trials.gov, A Pilot Study of SD-809 (Deutetrabenazine) in Moderate to Severe Tourette Syndrome (TS), https://clinicaltrials.gov/ct2/show/NCT02674321?term=SD809&rank=2 2014.
Chen, Tetrabenazine for the Treatment of Hyperkinetic Movement Disorders: A Review of the Literature, Clinical Therapeutics, 2012, 34(7), pp. 1487-1504.
Boldt et al., "Synthesis of (+)- and (−)-Tetrabenazine from the Resolution of a-Dihydrotetrabenazine" Synth. Commun., Nov. 2009, (39), 3574-3585.

(56) References Cited

OTHER PUBLICATIONS

"Determination of Whether SD-809 (Dutetrabenazine) and Tetrabenazine are Different Active Moieties" Center for Drug Evaluation and Research (CDER), Department of Health & Human Services, USA, Jul. 31, 2015, 5 Pages.

Frank, et al: JAMA Neurology, Safety of Converting From Tetrabenazine to Deutetrabenazine for the Treatment of Chorea; 2017; 74(8): pp. 977-982. doi:10.1001/jamaneurol.2017.1352.

Tetrabenazine as antichorea therapy in Huntington disease: A randomized controlled trial; Huntington Study Group; DOI: 10.1212/01.wnl.0000198586.85250.13; Neurology, Feb. 2006; 66; pp. 366-372.

\* cited by examiner

METHODS FOR THE TREATMENT OF ABNORMAL INVOLUNTARY MOVEMENT DISORDERS

This application is a continuation of U.S. application Ser. No. 15/063,068, filed Mar. 7, 2016, which claims the benefit of priority of U.S. Provisional Applications No. 62/129,616, filed Mar. 6, 2015, No. 62/175,112, filed Jun. 12, 2015, and No. 62/180,012, filed Jun. 15, 2015, the disclosures of each of which is hereby incorporated by reference as if written herein in its entirety.

Disclosed herein are new dosing regimens for deuterium-substituted benzoquinoline compounds, and methods for the treatment of abnormal involuntary movements, abnormal muscular activity, movement disorders, and related conditions.

Movement disorders are neurological conditions that affect the speed, fluency, quality, and ease of movement. Movement disorders can be classified into two basic categories: those characterized by disordered or excessive movement (referred to as "dyskinesia" and "hyperkinesia" or "hyperkinetic movement disorders," respectively), and those that are characterized by slowness, or a lack of movement (referred to as "hypokinesia," "bradykinesia," or "akinesia"). An example of a "hyperkinetic" movement disorder is chorea, such as that associated with Huntington's disease (HD), while Parkinson's disease (PD) can be classified as "hypokinetic," because it is often characterized by slow, deliberate movements, or even freezing in place. Both hyperkinetic and hypokinetic movement disorders can severely affect a subject's quality of life, making daily tasks difficult. Additionally, movement disorders can cause a subject physical pain and increase the probability of accidents.

For example, chorea is an abnormal, involuntary, sudden movement that can affect all muscle groups and flow randomly from one body region to another; like many abnormal involuntary movements, it is often alternatively referred to as a movement disorder. Chorea is a hallmark of Huntington's Disease. In the United States, an estimated 30,000 people have Huntington's disease. As many as 90% of patients with HD experience chorea and it is moderate to severe in approximately 70% of these patients. It is considered by clinicians to be a serious condition, given its significant interference with daily functioning and increased risk for injury to the patient. In its early stages, chorea can contribute to impaired speaking, writing, and activities of daily living such as feeding, dressing, and bathing. In its later stages, chorea can cause gait instability and poor postural control, with an increased risk of serious injury from falling or from flailing into objects. Severity of chorea and parkinsonism has been shown to be independently associated with falls in later-stage patients with HD. Dysphagia is a component of HD and can lead to recurrent aspiration pneumonia, weight loss, and behavioral problems.

The American Academy of Neurology's guideline indicates that, "Huntington's disease remains a devastating neurodegenerative disease in need of neuroprotective and symptomatic treatments" and that "treating chorea is an important part of Huntington's disease management." A survey of 52 international experts indicated they would treat chorea for the following reasons: 88% physical injury, 81% loss of balance, 77% social isolation, and 77% interference with work. Despite this guidance, patients with HD who have chorea are not often treated.

The only FDA-approved therapy in the United States for the treatment of chorea associated with HD is tetrabenazine (XENAZINE®), an inhibitor of VMAT2. Tetrabenazine reduces presynaptic concentrations of monoamines, such as dopamine, in neurons that regulate body movements. Although approximately 30,000 people in the United States are affected by HD and approximately 200,000 individuals may carry the gene and be at risk of developing HD, according to a November 2013 presentation by Lundbeck, only approximately 4,000 patients received this therapy. A substantial majority of patients with chorea of HD are not receiving treatment with tetrabenazine. Furthermore, based on interviews with physicians in 2011, it is estimated that use of tetrabenazine in hyperkinetic movement disorders other than the chorea of HD may account for up to half of its use, indicating that as few as 2,000 patients with HD are receiving tetrabenazine. Additionally, a report from the Baylor College of Medicine indicated that only 78 of the 349 hyperkinetic movement disorder patients treated with tetrabenazine between 2006 and 2009 were patients with chorea. Clearly, a substantial need for effective treatments for movement disorders exists, and is only partially met by available therapies.

In addition to chorea, impairment in overall motor symptoms severely disrupt day-to-day functioning. The National Institutes of Neurological Disorders and Stroke considers the Unified Huntington's Disease Rating Scale (UHDRS) motor function assessments in the Total Motor Score (TMS) to be a core outcome in the evaluation of HD. All currently recruiting large Phase 2b/3 randomized clinical trials in patients with HD in the United States are using UHDRS-TMS as their primary endpoint. Significant correlations between the UHDRS-TMS and functional measures for sleep, rest, eating, work, recreation and past-times, ambulation, mobility, body care and movement, social interaction, communication, physical, and psychosocial dimensions have been shown in patients with HD. Higher UHDRS-TMS scores are associated with a statistically significant lower likelihood of performing work, managing finances, driving safely, supervising children, and volunteering. Every 1-point worsening in the TMS was associated a 5% to 10% reduction in the likelihood of being able to complete these certain tasks. The UHDRS-TMS is an independent predictor of functional disability based on scales including the 36-Item Short-Form Health Survey (SF-36).

Also in the United States, an estimated 500,000 patients have the movement disorder tardive dyskinesia and experience abnormal muscular activity. Tardive dyskinesia is a hyperkinetic movement disorder that typically manifests as rapid, repetitive, stereotypic movements that can be induced by certain drugs, such as neuroleptics, such as dopamine receptor blocking agents, which are used for treating psychiatric conditions, as well as by drugs such as metoclopramide, which are used for treating various gastrointestinal disorders. These patients are managed largely by psychiatrists and movement disorder neurologists, and there are no FDA-approved treatments for tardive dyskinesia.

Also in the United States, an estimated 100,000 children have tics (abnormal involuntary movements or vocalizations) associated with Tourette syndrome, with an estimated 27% categorized as moderate to severe. Peak severity of the disorder is around 12 years of age, with an estimated 13% to 22% of affected children continuing to take medications for tics as adults. Few new drugs have been introduced for treating a tic associated with Tourette syndrome in more than 30 years; inadequacies can be identified in the two approved neuroleptics and one recently-approved dopamine antagonist. For example, these treatments carry, among other adverse events, the risk of causing permanent neurologic deficits, such as tardive dyskinesia.

Accordingly, there remains a need for improved compositions, dosing regimens, and methods for the treatment of abnormal muscular activity, abnormal involuntary movement and other related disorders.

DETAILED DESCRIPTION OF THE INVENTION

Figure 1:
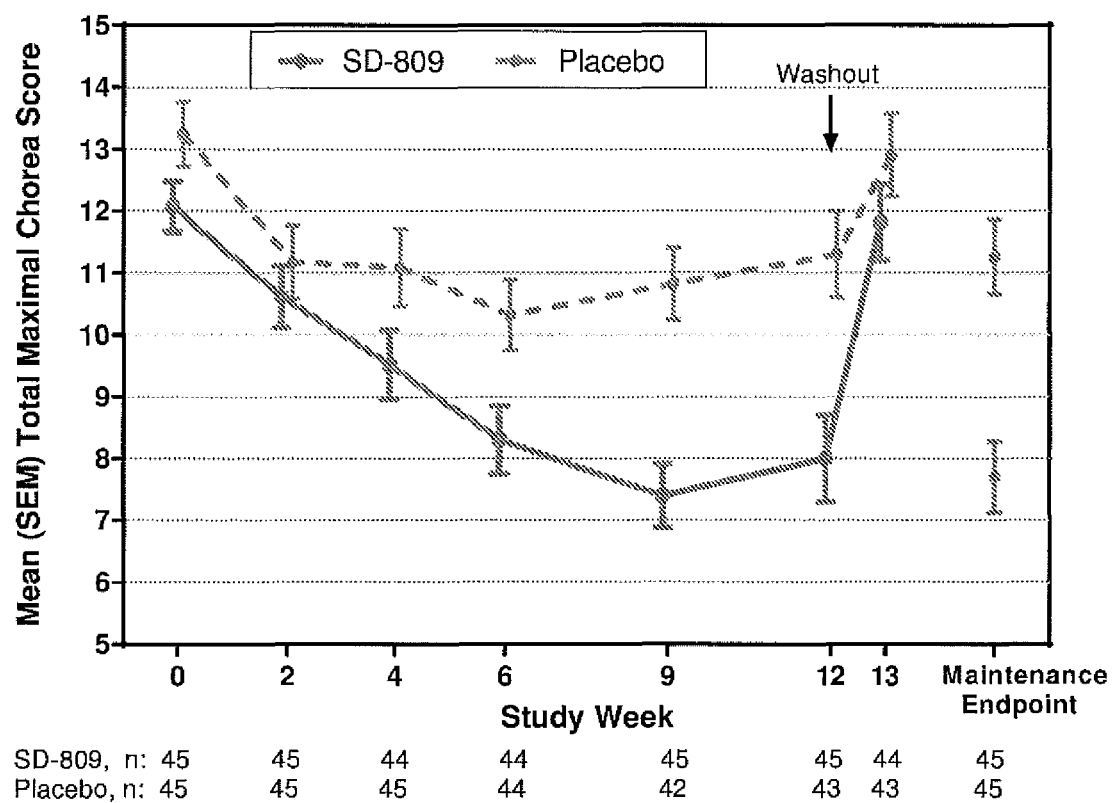
FIG. 1 shows change in mean chorea score observed in patients taking either deutetrabenazine or placebo from the First-HD study.

Disclosed herein is a method of treating abnormal involuntary movement in a subject, comprising:
   a) administering to the subject an initial daily amount of a deuterium substituted tetrabenazine comprising at least about 6 mg per day;
   b) determining after about one week the degree of control of abnormal involuntary movement achieved with the initial daily amount and the tolerability of the initial daily amount;
   c) increasing the daily amount of the deuterium substituted tetrabenazine upward by 6 or more mg/day to a subsequent daily amount if the degree of control of abnormal involuntary movement is inadequate and the initial daily amount is tolerable;
   d) optionally, repeating steps b) and c) until the degree of control of abnormal involuntary movement is adequate and the daily amount of the deuterium substituted tetrabenazine is tolerable; and
   e) if any subsequent amount is intolerable, decreasing the daily amount downward by 6 or more mg/day to a subsequent daily amount.

Also disclosed is a method of treating abnormal involuntary movement in a subject, comprising:
   a) administering to the subject an initial daily amount of deutetrabenazine of at least about 6 mg per day;
   b) determining after about one week the degree of control of abnormal involuntary movement achieved with the initial daily amount and the tolerability of the initial daily amount;
   c) increasing the daily amount of the deutetrabenazine upward by 6 mg/day to a subsequent daily amount if the abnormal involuntary movement is not reduced and the initial daily amount is tolerable;
   d) after about one week, optionally, repeating steps b) and c) provided that abnormal involuntary movement is reduced and the daily amount of the deutetrabenazine is tolerable; and
   e) if any subsequent amount is not tolerated, decreasing the daily amount downward by at least 6 mg/day to a subsequent daily amount.

In certain embodiments, the abnormal involuntary movement is caused by a movement disorder.

In certain embodiments, the movement disorder is chosen from akathisia, akinesia, ataxia, athetosis, ballismus, bradykinesia, cerebral palsy, chorea, corticobasal degeneration, dyskinesias (e.g., paroxysmal), dystonia (general, segmental, or focal) including blepharospasm, writer's cramp (limb dystonia), laryngeal dystonia (spasmodic dysphonia), and oromandibular dystonia, essential tremor, geniospasm, hereditary spastic paraplegia, Huntington's Disease, multiple system atrophy (Shy Drager Syndrome), myoclonus, Parkinson's Disease, Parkinson's disease levodopa-induced dyskinesia, parkinsonism, progressive supranuclear palsy, restless legs syndrome, Rett Syndrome, spasmodic torticollis (cervical dystonia), spasticity due to stroke, cerebral palsy, multiple sclerosis, spinal cord or brain injury, stereotypic movement disorder, stereotypy, Sydenham's Chorea, synkinesis, tardive dyskinesia, tics, Tourette syndrome, and Wilson's Disease.

In certain embodiments, the movement disorder is a hyperkinetic movement disorder.

In certain embodiments, the abnormal involuntary movement is chosen from chorea, akathisia, dyskinesia, tremor, and tic.

In certain embodiments, the abnormal involuntary movement is chorea. In certain embodiments, the abnormal involuntary movement is chorea associated with Huntington's disease. In certain embodiments, the abnormal involuntary movement is a tic. In certain embodiments, the abnormal involuntary movement is a tic associated with Tourette syndrome.

In certain embodiments, movement disorder is chosen from Huntington's disease, tardive dyskinesia, tics associated with Tourette syndrome, dystonia, and Parkinson's disease levodopa-induced dyskinesia.

In certain embodiments, the movement disorder is chosen from Huntington's disease, tardive dyskinesia, and Tourette syndrome.

In certain embodiments, the movement disorder is Huntington's disease.

In certain embodiments, the movement disorder is chorea associated with Huntington's disease.

In certain embodiments, the absence of a reduction or suspension in an initial or subsequent daily amount indicates that the daily amount is tolerable. In certain embodiments, the tolerability is determined by assessment of one or more of the subject's levels of depression, anxiety, insomnia, somnolence, fatigue, dizziness, restlessness, agitation, irritability, akathisia, tardive dyskinesia, swallowing, parkinsonism, vomiting and nausea. In certain embodiments, a dose is not tolerated if one or more of the foregoing occur. In certain embodiments, a dose is not tolerated if somnolence or dizziness occur.

In certain embodiments, the deuterium substituted tetrabenazine is deutetrabenazine. In certain embodiments, the deutetrabenazine is a plus isomeric form of deutetrabenazine. In certain embodiments, the plus isomeric form of deutetrabenazine is an alpha isomer. In certain embodiments, the VMAT2 inhibitor is a plus isomeric form of tetrabenazine. In certain embodiments, the plus isomeric form of tetrabenazine is an alpha isomer.

In certain embodiments, the initial daily amount of deutetrabenazine is about 30% to about 70% of an existing total daily amount of tetrabenazine that provides adequate control of the abnormal involuntary movement. In certain embodiments, the initial daily amount of deutetrabenazine is about 40% to about 60% of an existing total daily amount of tetrabenazine that provides adequate control of the abnormal involuntary movement. In certain embodiments, the initial daily amount of deutetrabenazine is about 45% to about 55% of an existing total daily amount of tetrabenazine that provides adequate control of the abnormal involuntary movement. In certain embodiments, the initial daily amount of deutetrabenazine is about 30% to about 50% of an existing total daily amount of tetrabenazine that provides adequate control of the abnormal involuntary movement.

In certain embodiments, the daily amount of deutetrabenazine is administered in one dose or two doses.

In certain embodiments, the initial daily amount of deutetrabenazine is chosen from about 6 mg, about 12 mg, about 18 mg, about 24 mg, about 30 mg, about 36 mg, about 42 mg, about 48 mg, about 54 mg, about 60 mg, about 66 mg, about 72 mg, and about 78 mg. In certain embodiments, the initial daily amount of deutetrabenazine is chosen from about 6 mg, about 12 mg, about 18 mg, about 24 mg, about 30 mg, about 36 mg, about 42 mg, and about 48 mg.

In certain embodiments, the initial daily amount of deutetrabenazine is administered in two doses, consisting of a first dose and a second dose.

In certain embodiments:
the first dose about 6 mg and the second dose is about 6 mg;
the first dose about 9 mg and the second dose is about 9 mg;
the first dose about 12 mg and the second dose is about 12 mg;
the first dose about 15 mg and the second dose is about 15 mg;
the first dose about 18 mg and the second dose is about 18 mg;
the first dose about 21 mg and the second dose is about 21 mg;
the first dose about 24 mg and the second dose is about 24 mg;
the first dose about 27 mg and the second dose is about 27 mg;
the first dose about 30 mg and the second dose is about 30 mg;
the first dose about 33 mg and the second dose is about 33 mg;
the first dose about 36 mg and the second dose is about 36 mg; and
the first dose about 39 mg and the second dose is about 39 mg.

In certain embodiments:
the first dose about 6 mg and the second dose is about 6 mg;
the first dose about 9 mg and the second dose is about 9 mg;
the first dose about 12 mg and the second dose is about 12 mg;
the first dose about 15 mg and the second dose is about 15 mg;
the first dose about 18 mg and the second dose is about 18 mg;
the first dose about 21 mg and the second dose is about 21 mg; and
the first dose about 24 mg and the second dose is about 24 mg.

In certain embodiments, the daily amount of deutetrabenazine is about 6 mg to about 78 mg. In certain embodiments, the daily amount of deutetrabenazine is chosen from about 6 mg, about 12 mg, about 18 mg, about 24 mg, about 30 mg, about 36 mg, about 42 mg, about 48 mg, about 54 mg, about 60 mg, about 66 mg, about 72 mg, and about 78 mg. In certain embodiments, the daily amount of deutetrabenazine is chosen from about 6 mg, about 12 mg, about 18 mg, about 24 mg, about 30 mg, about 36 mg, about 42 mg, and about 48 mg.

In certain embodiments, the daily amount of deutetrabenazine administered is less than or equal to about 48 mg, or less than or equal to about 36 mg for a subject concurrently receiving a strong CYP2D6 inhibitor. In certain embodiments, the strong CYP2D6 inhibitor is chosen from fluoxetine, paroxetine, bupropion, quinidine, cinacalcet, and ritonavir. In certain embodiments, the strong CYP2D6 inhibitor is chosen from paroxetine, fluoxetine, and bupropion.

In certain embodiments, the degree of chorea control is improved by a reduction of at least 0.5 points on the Total Maximal Chorea (TMC) score. In certain embodiments, the reduction in TMC score is at least 1 point. In certain embodiments, the reduction in TMC score is at least 1.5 points. In certain embodiments, the reduction in TMC score is at least 2.0 points. In certain embodiments, the reduction in TMC score is at least 2.5 points. In certain embodiments, the improvement is over a pre-treatment, "baseline" TMC score of at least 8.0. In certain embodiments, the improvement is over a pre-treatment, "baseline" TMC score of at least 10.0. In certain embodiments, the improvement is over a pre-treatment, "baseline" TMC score of at least 12.0. In certain embodiments, the improvement is over a pre-treatment, "baseline" TMC score of at least 12.7. In certain embodiments, the improvement is over a pre-treatment, "baseline" TMC score of at least 14.0.

In certain embodiments, chorea is reduced by at least 10%. In certain embodiments, chorea is reduced by at least 15%. In certain embodiments, chorea is reduced by at least 20%.

In certain embodiments, motor function is improved. In certain embodiments, motor function is improved by a reduction of at least 1 point on the Total Motor Score (TMS). In certain embodiments, the reduction in TMS score is at least 2 points. In certain embodiments, the reduction in TMS score is at least 3 points. In certain embodiments, the reduction in TMS score is at least 4 points.

In certain embodiments, dystonia is improved. In certain embodiments, gait is improved. In certain embodiments, postural instability is alleviated. In certain embodiments, treatment reduces the symptoms of parkinsonism.

In certain embodiments, the treatment does not worsen balance. In certain embodiments, the treatment improves balance.

In certain embodiments, the treatment improves physical functioning. In certain embodiments, the subject's physical functioning is improved as measured by the SF-36 physical functioning scale. In certain embodiments, the subject's physical functioning is improved as measured by the SF-36 physical functioning scale from baseline. In certain embodiments, the subject's physical functioning is improved as measured by the SF-36 physical functioning scale compared to untreated subjects.

In certain embodiments, the subject is much improved on the PGIC scale. In certain embodiments, the subject is very much improved on the PGIC scale. In certain embodiments, the subject is much improved on the CGIC scale. In certain embodiments, the subject is very much improved on the CGIC scale. In certain embodiments, the subject is much improved on the PGIC and CGIC scales. In certain embodiments, the subject is very much improved on the PGIC and CGIC scales.

In certain embodiments, the treatment improves swallowing.

In certain embodiments, treatment causes no significant increase in insomnia, depression, anxiety, agitation, suicidal ideation, akathisia, irritability, or fatigue.

In certain embodiments, treatment causes no significant symptoms of parkinsonism or dysphagia.

In certain embodiments, the treatment does not significantly prolong the QT interval. In certain embodiments, the treatment does not significantly change the QTcF value. In certain embodiments, the maximal increases in QTcF is less than 5 ms.

Also provided are embodiments wherein any embodiment above in paragraphs [023]-[054] above may be combined with any one or more of these embodiments, provided the combination is not mutually exclusive. As used herein, two embodiments are "mutually exclusive" when one is defined to be something which cannot overlap with the other. Also provided is the use of deutetrabenazine for treating abnormal involuntary movement in a subject, as set forth herein or in any of the embodiments above in paragraphs [023]-[054] above. Also provided is the use of deutetrabenazine in the manufacture of a medicament for treating abnormal involuntary movement in a subject, as set forth herein or in any of the embodiments above in paragraphs [023]-[054] above. Also provided is a composition comprising deutetrabenazine for treating abnormal involuntary movement in a subject, as set forth herein or in any of the embodiments above in paragraphs [023]-[054] above.

Also provided is a method of transitioning a subject receiving an existing total daily amount of tetrabenazine for control of abnormal involuntary movement, comprising:
a) administering to the subject an initial daily amount of a deuterium substituted tetrabenazine which is about 30% to about 70% of the existing total daily amount of tetrabenazine and is at least about 6 mg per day;
b) concurrently discontinuing the daily amount of tetrabenazine;
c) optionally, after about one week, determining the degree of control of abnormal involuntary movement achieved with the initial daily amount of a deuterium substituted tetrabenazine and the tolerability of the initial amount;
d) optionally, if the degree of control of abnormal involuntary movement is comparable to the control when the subject was receiving tetrabenazine or inadequate and the initial amount is tolerable, increasing the daily amount upward by 6 or more mg/day to a subsequent daily amount;
e) optionally, repeating steps c) and d) until the degree of control of abnormal involuntary movement is improved and the initial amount is tolerable; and
f) optionally, if any subsequent amount is intolerable, decreasing the daily amount downward by 6 or more mg/day to a subsequent daily amount.

Also provided is a method of transitioning a subject receiving an existing daily amount of tetrabenazine for control of abnormal involuntary movement from tetrabenazine to deutetrabenazine, comprising:
a) discontinuing the daily amount of tetrabenazine;
b) the next day, administering to the subject an initial daily amount of deutetrabenazine, which is about 30% to about 70% of the existing total daily amount of tetrabenazine and is at least about 6 mg per day;
c) after about one week, determining the degree of control of abnormal involuntary movement achieved with the initial daily amount of a deuterium substituted tetrabenazine and the tolerability of the initial amount;
d) if the degree of control of abnormal involuntary movement is comparable to the control when the subject was receiving tetrabenazine or inadequate and the initial amount is tolerated, increasing the daily amount upward by 6 mg/day to a subsequent daily amount of deutetrabenazine;
e) after about one week, optionally, repeating steps c) and d) provided that abnormal involuntary movement is reduced and the amount is tolerated; and
f) optionally, if any subsequent amount is not tolerated, decreasing the daily amount downward by 6 mg/day to a subsequent daily amount.

In certain embodiments, the initial daily amount of deutetrabenazine is about 40% to about 60% of the existing total daily amount of tetrabenazine and is at least about 6 mg per day. In certain embodiments, the initial daily amount of deutetrabenazine is about 45% to about 55% of the existing total daily amount of tetrabenazine and is at least about 6 mg per day. In certain embodiments, the initial daily amount of deutetrabenazine is about 30% to about 50% of the existing total daily amount of tetrabenazine and is at least about 6 mg per day.

In certain embodiments, the abnormal involuntary movement is caused by a movement disorder.

In certain embodiments, the movement disorder is chosen from akathisia, akinesia, ataxia, athetosis, ballismus, bradykinesia, cerebral palsy, chorea, corticobasal degeneration, dyskinesias (e.g., paroxysmal), dystonia (general, segmental, or focal) including blepharospasm, writer's cramp (limb dystonia), laryngeal dystonia (spasmodic dysphonia), and oromandibular dystonia, essential tremor, geniospasm, hereditary spastic paraplegia, Huntington's Disease, multiple system atrophy (Shy Drager Syndrome), myoclonus, Parkinson's Disease, Parkinson's disease levodopa-induced dyskinesia, parkinsonism, progressive supranuclear palsy, restless legs syndrome, Rett Syndrome, spasmodic torticollis (cervical dystonia), spasticity due to stroke, cerebral palsy, multiple sclerosis, spinal cord or brain injury, stereotypic movement disorder, stereotypy, Sydenham's Chorea, synkinesis, tardive dyskinesia, tics, Tourette syndrome, and Wilson's Disease.

In certain embodiments, the movement disorder is a hyperkinetic movement disorder.

In certain embodiments, the abnormal involuntary movement is chosen from chorea, akathisia, dyskinesia, tremor, and tic.

In certain embodiments, the abnormal involuntary movement is chorea. In certain embodiments, the abnormal involuntary movement is chorea associated with Huntington's disease. In certain embodiments, the abnormal involuntary movement is a tic. In certain embodiments, the abnormal involuntary movement is a tic associated with Tourette syndrome.

In certain embodiments, movement disorder is chosen from Huntington's disease, tardive dyskinesia, tics associated with Tourette syndrome, dystonia, and Parkinson's disease levodopa-induced dyskinesia.

In certain embodiments, the movement disorder is chosen from Huntington's disease, tardive dyskinesia, and Tourette syndrome.

In certain embodiments, the movement disorder is Huntington's disease.

In certain embodiments, the movement disorder is chorea associated with Huntington's disease.

In certain embodiments, the absence of a reduction or suspension in an initial or subsequent daily amount indicates that the daily amount is tolerable. In certain embodiments, the tolerability is determined by assessment of one or more of the subject's levels of depression, anxiety, insomnia, somnolence, fatigue, dizziness, restlessness, agitation, irritability, akathisia, tardive dyskinesia, swallowing, parkinsonism, vomiting and nausea. In certain embodiments, a dose is not tolerated if one or more of the foregoing occur. In certain embodiments, a dose is not tolerated if somnolence or dizziness occur.

In certain embodiments, the deuterium substituted tetrabenazine is deutetrabenazine. In certain embodiments, the deutetrabenazine is a plus isomeric form of deutetrabenazine. In certain embodiments, the plus isomeric form of deutetrabenazine is an alpha isomer. In certain embodiments, the VMAT2 inhibitor is a plus isomeric form of tetrabenazine. In certain embodiments, the plus isomeric form of tetrabenazine is an alpha isomer.

In certain embodiments, the daily amount of deutetrabenazine is administered in one dose or two doses.

In certain embodiments, the initial daily amount of deutetrabenazine is chosen from about 6 mg, about 12 mg, about 18 mg, about 24 mg, about 30 mg, about 36 mg, about 42 mg, about 48 mg, about 54 mg, about 60 mg, about 66 mg, about 72 mg, and about 78 mg. In certain embodiments, the initial daily amount of deutetrabenazine is chosen from about 6 mg, about 12 mg, about 18 mg, about 24 mg, about 30 mg, about 36 mg, about 42 mg, and about 48 mg. In certain embodiments, the daily amount of deutetrabenazine is about 6 mg to about 78 mg. In certain embodiments, the daily amount of deutetrabenazine is chosen from about 6 mg, about 12 mg, about 18 mg, about 24 mg, about 30 mg, about 36 mg, about 42 mg, about 48 mg, about 54 mg, about 60 mg, about 66 mg, about 72 mg, and about 78 mg. In certain embodiments, the daily amount of deutetrabenazine is chosen from about 6 mg, about 12 mg, about 18 mg, about 24 mg, about 30 mg, about 36 mg, about 42 mg, and about 48 mg.

In certain embodiments, the initial daily amount of deutetrabenazine is administered in two doses, consisting of a first dose and a second dose.

In certain embodiments:

the first dose about 6 mg and the second dose is about 6 mg;

the first dose about 9 mg and the second dose is about 9 mg;

the first dose about 12 mg and the second dose is about 12 mg;

the first dose about 15 mg and the second dose is about 15 mg;

the first dose about 18 mg and the second dose is about 18 mg;

the first dose about 21 mg and the second dose is about 21 mg;

the first dose about 24 mg and the second dose is about 24 mg;

the first dose about 27 mg and the second dose is about 27 mg;

the first dose about 30 mg and the second dose is about 30 mg;

the first dose about 33 mg and the second dose is about 33 mg;

the first dose about 36 mg and the second dose is about 36 mg; and the first dose about 39 mg and the second dose is about 39 mg.

In certain embodiments:

the first dose about 6 mg and the second dose is about 6 mg;

the first dose about 9 mg and the second dose is about 9 mg;

the first dose about 12 mg and the second dose is about 12 mg;

the first dose about 15 mg and the second dose is about 15 mg;

the first dose about 18 mg and the second dose is about 18 mg;

the first dose about 21 mg and the second dose is about 21 mg; and the first dose about 24 mg and the second dose is about 24 mg.

In certain embodiments:

the existing total daily amount of tetrabenazine is about 12.5 mg and the initial daily amount of deutetrabenazine is about 6 mg;

the existing total daily amount of tetrabenazine is about 25 mg and the initial daily amount of deutetrabenazine is about 12 mg;

the existing total daily amount of tetrabenazine is about 37.5 mg and the initial daily amount of deutetrabenazine is about 18 mg;

the existing total daily amount of tetrabenazine is about 50 mg and the initial daily amount of deutetrabenazine is about 24 mg;

the existing total daily amount of tetrabenazine is about 62.5 mg and the initial daily amount of deutetrabenazine is about 30 mg;

the existing total daily amount of tetrabenazine is about 75 mg and the initial daily amount of deutetrabenazine is about 36 mg;

the existing total daily amount of tetrabenazine is about 87.5 mg and the initial daily amount of deutetrabenazine is about 42 mg; or the existing total daily amount of tetrabenazine is about 100 mg and the initial daily amount of deutetrabenazine is about 48 mg.

In certain embodiments, the daily amount of deutetrabenazine is about 6 mg to about 78 mg. In certain embodiments, the daily amount of deutetrabenazine is chosen from about 6 mg, about 12 mg, about 18 mg, about 24 mg, about 30 mg, about 36 mg, about 42 mg, about 48 mg, about 54 mg, about 60 mg, about 66 mg, about 72 mg, and about 78 mg. In certain embodiments, the daily amount of deutetrabenazine is chosen from about 6 mg, about 12 mg, about 18 mg, about 24 mg, about 30 mg, about 36 mg, about 42 mg, and about 48 mg.

In certain embodiments, the daily amount of deutetrabenazine administered is less than or equal to about 48 mg, or less than or equal to about 36 mg for subjects concurrently receiving a strong CYP2D6 inhibitor. In certain embodiments, the strong CYP2D6 inhibitor is chosen from fluoxetine, paroxetine, bupropion, quinidine, cinacalcet, and ritonavir. In certain embodiments, the strong CYP2D6 inhibitor is chosen from paroxetine, fluoxetine, and bupropion.

In certain embodiments, the chorea control is improved by a reduction of at least 0.5 points on the Total Maximal Chorea (TMC) score. In certain embodiments, the reduction in TMC score is at least 1 point. In certain embodiments, the reduction in TMC score is at least 1.5 points. In certain embodiments, the reduction in TMC score is at least 2.0 points. In certain embodiments, the reduction in TMC score is at least 2.5 points. In certain embodiments, the improvement is over a pre-treatment, "baseline" TMC score of at least 8.0. In certain embodiments, the improvement is over a pre-treatment, "baseline" TMC score of at least 10.0. In certain embodiments, the improvement is over a pre-treatment, "baseline" TMC score of at least 12.0. In certain embodiments, the improvement is over a pre-treatment, "baseline" TMC score of at least 12.7. In certain embodiments, the improvement is over a pre-treatment, "baseline" TMC score of at least 14.0.

In certain embodiments, chorea is reduced by at least 10%. In certain embodiments, chorea is reduced by at least 15%. In certain embodiments, chorea is reduced by at least 20%.

In certain embodiments, motor function is improved.

In certain embodiments, motor function is improved by a reduction of at least 1 point on the Total Motor Score (TMS). In certain embodiments, the reduction in TMS score is at least 2 points. In certain embodiments, the reduction in TMS score is at least 3 points. In certain embodiments, the reduction in TMS score is at least 4 points.

In certain embodiments, dystonia is improved. In certain embodiments, gait is improved. In certain embodiments, postural instability is alleviated. In certain embodiments, treatment reduces the symptoms of parkinsonism.

In certain embodiments, the treatment does not worsen the subject's balance. In certain embodiments, the treatment improves balance.

In certain embodiments, the treatment improves physical functioning. In certain embodiments, the subject's physical functioning is improved as measured by the SF-36 physical functioning scale. In certain embodiments, the subject's physical functioning is improved as measured by the SF-36 physical functioning scale from baseline. In certain embodiments, the subject's physical functioning is improved as measured by the SF-36 physical functioning scale compared to untreated subjects.

In certain embodiments, the subject is much improved on the PGIC scale. In certain embodiments, the subject is very much improved on the PGIC scale. In certain embodiments, the subject is much improved on the CGIC scale. In certain embodiments, the subject is very much improved on the CGIC scale. In certain embodiments, the subject is much improved on the PGIC and CGIC scales. In certain embodiments, the subject is very much improved on the PGIC and CGIC scales.

In certain embodiments, the treatment improves swallowing.

In certain embodiments, treatment causes no significant increase in insomnia, depression, anxiety, agitation, suicidal ideation, akathisia, irritability, or fatigue.

In certain embodiments, treatment causes no significant parkinsonism or dysphagia.

In certain embodiments, the treatment does not significantly prolong the QT interval. In certain embodiments, the treatment does not significantly change the QTcF value. In certain embodiments, the maximal increases in QTcF is less than 5 ms.

Also provided are embodiments wherein any embodiment above in paragraphs [056]-[090] above may be combined with any one or more of these embodiments, provided the combination is not mutually exclusive. Also provided is the use of deutetrabenazine for transitioning a subject receiving an existing total daily amount of tetrabenazine for control of abnormal involuntary movement, as set forth herein or in any of the embodiments above in paragraphs [056]-[090] above. Also provided is the use of deutetrabenazine in the manufacture of a medicament for transitioning a subject receiving an existing total daily amount of tetrabenazine for control of abnormal involuntary movement, as set forth herein or in any of the embodiments above in paragraphs [056]-[090] above. Also provided is a composition comprising deutetrabenazine for use in transitioning a subject receiving an existing total daily amount of tetrabenazine for control of abnormal involuntary movement, as set forth herein or in any of the embodiments above in paragraphs [056]-[090] above.

Also provided is a method of treating a movement disorder in a subject comprising the administration of a daily amount of a VMAT2 inhibitor, wherein either:

chorea is reduced by at least 10% and any one or more of the following are true:

motor function is improved by at least 10%;
the subject's physical functioning is improved;
swallowing is improved;
balance is not worsened;
treatment causes no significant increase in insomnia, depression, anxiety, agitation, suicidal ideation, akathisia, irritability, fatigue, parkinsonism or dysphagia; and
the maximal increases in QTcF is less than 5 ms;

or motor function is improved by at least 10%, and any one or more of the following are true:

chorea is reduced by at least 10%;
the subject's physical functioning is improved;
swallowing is improved;
balance is not worsened;
treatment causes no significant increase in insomnia, depression, anxiety, agitation, suicidal ideation, akathisia, irritability, fatigue, parkinsonism or dysphagia; and
the maximal increases in QTcF is less than 5 ms.

In certain embodiments, the movement disorder is chosen from akathisia, akinesia, ataxia, athetosis, ballismus, bradykinesia, cerebral palsy, chorea, corticobasal degeneration, dyskinesias (e.g., paroxysmal), dystonia (general, segmental, or focal) including blepharospasm, writer's cramp (limb dystonia), laryngeal dystonia (spasmodic dysphonia), and oromandibular dystonia, essential tremor, geniospasm, hereditary spastic paraplegia, Huntington's Disease, multiple system atrophy (Shy Drager Syndrome), myoclonus, Parkinson's Disease, Parkinson's disease levodopa-induced dyskinesia, parkinsonism, progressive supranuclear palsy, restless legs syndrome, Rett Syndrome, spasmodic torticollis (cervical dystonia), spasticity due to stroke, cerebral palsy, multiple sclerosis, spinal cord or brain injury, stereotypic movement disorder, stereotypy, Sydenham's Chorea, synkinesis, tardive dyskinesia, tics, Tourette syndrome, and Wilson's Disease.

In certain embodiments, the movement disorder is a hyperkinetic movement disorder.

In certain embodiments, dystonia is improved. In certain embodiments, gait is improved. In certain embodiments, postural instability is alleviated. In certain embodiments, treatment reduces the symptoms of parkinsonism.

In certain embodiments, the movement disorder is chosen from Huntington's disease, tardive dyskinesia, and tics associated with Tourette syndrome.

In certain embodiments, the movement disorder is Huntington's disease. In certain embodiments, the movement disorder is chorea associated with Huntington's disease.

In certain embodiments, the movement disorder is a tic. In certain embodiments, the movement disorder is a tic associated with Tourette syndrome.

In certain embodiments, the VMAT2 inhibitor is a deuterium substituted tetrabenazine. In certain embodiments, the deuterium substituted tetrabenazine is deutetrabenazine. In certain embodiments, the deutetrabenazine is a plus isomeric form of deutetrabenazine. In certain embodiments, the plus isomeric form of deutetrabenazine is an alpha isomer. In certain embodiments, the VMAT2 inhibitor is a plus isomeric form of tetrabenazine. In certain embodiments, the plus isomeric form of tetrabenazine is an alpha isomer. In certain embodiments, the VMAT2 inhibitor is valbenazine.

In certain embodiments, the daily amount of deutetrabenazine is administered in one dose or two doses.

In certain embodiments, the daily amount of deutetrabenazine is about 6 mg to about 78 mg. In certain embodiments, the daily amount of deutetrabenazine is chosen from about 6 mg, about 12 mg, about 18 mg, about 24 mg, about 30 mg, about 36 mg, about 42 mg, about 48 mg, about 54 mg, about 60 mg, about 66 mg, about 72 mg, and about 78 mg. In certain embodiments, the daily amount of deutetrabenazine is chosen from about 6 mg, about 12 mg, about 18 mg, about 24 mg, about 30 mg, about 36 mg, about 42 mg, and about 48 mg.

In certain embodiments, the daily amount of deutetrabenazine is administered in two doses, consisting of a first dose and a second dose.

In certain embodiments:
the first dose about 6 mg and the second dose is about 6 mg;
the first dose about 9 mg and the second dose is about 9 mg;
the first dose about 12 mg and the second dose is about 12 mg;
the first dose about 15 mg and the second dose is about 15 mg;
the first dose about 18 mg and the second dose is about 18 mg;
the first dose about 21 mg and the second dose is about 21 mg;
the first dose about 24 mg and the second dose is about 24 mg;
the first dose about 27 mg and the second dose is about 27 mg;
the first dose about 30 mg and the second dose is about 30 mg;
the first dose about 33 mg and the second dose is about 33 mg;
the first dose about 36 mg and the second dose is about 36 mg; and
the first dose about 39 mg and the second dose is about 39 mg.

In certain embodiments:
the first dose about 6 mg and the second dose is about 6 mg;
the first dose about 9 mg and the second dose is about 9 mg;
the first dose about 12 mg and the second dose is about 12 mg;
the first dose about 15 mg and the second dose is about 15 mg;
the first dose about 18 mg and the second dose is about 18 mg;
the first dose about 21 mg and the second dose is about 21 mg; and
the first dose about 24 mg and the second dose is about 24 mg.

In certain embodiments, the daily amount of deutetrabenazine is about 6 mg to about 78 mg. In certain embodiments, the daily amount of deutetrabenazine is chosen from about 6 mg, about 12 mg, about 18 mg, about 24 mg, about 30 mg, about 36 mg, about 42 mg, about 48 mg, about 54 mg, about 60 mg, about 66 mg, about 72 mg, and about 78 mg. In certain embodiments, the daily amount of deutetrabenazine is chosen from about 6 mg, about 12 mg, about 18 mg, about 24 mg, about 30 mg, about 36 mg, about 42 mg, and about 48 mg.

In certain embodiments, the daily amount of deutetrabenazine administered is less than or equal to about 48 mg, or less than or equal to about 36 mg for subjects concurrently receiving a strong CYP2D6 inhibitor. In certain embodiments, the strong CYP2D6 inhibitor is chosen from fluoxetine, paroxetine, bupropion, quinidine, cinacalcet, and ritonavir. In certain embodiments, the strong CYP2D6 inhibitor is chosen from paroxetine, fluoxetine, and bupropion.

In certain embodiments, the chorea control is improved by a reduction of at least 0.5 points on the Total Maximal Chorea (TMC) score. In certain embodiments, the reduction in TMC score is at least 1 point. In certain embodiments, the reduction in TMC score is at least 1.5 points. In certain embodiments, the reduction in TMC score is at least 2.0 points. In certain embodiments, the reduction in TMC score is at least 2.5 points. In certain embodiments, the improvement is over a pre-treatment, "baseline" TMC score of at least 8.0. In certain embodiments, the improvement is over a pre-treatment, "baseline" TMC score of at least 10.0. In certain embodiments, the improvement is over a pre-treatment, "baseline" TMC score of at least 12.0. In certain embodiments, the improvement is over a pre-treatment, "baseline" TMC score of at least 12.7. In certain embodiments, the improvement is over a pre-treatment, "baseline" TMC score of at least 14.0.

In certain embodiments, chorea is reduced by at least 10%. In certain embodiments, chorea is reduced by at least 15%. In certain embodiments, chorea is reduced by at least 20%.

In certain embodiments, motor function is improved.

In certain embodiments, motor function is improved by a reduction of at least 1 point on the Total Motor Score (TMS). In certain embodiments, the reduction in TMS score is at least 2 points. In certain embodiments, the reduction in TMS score is at least 3 points. In certain embodiments, the reduction in TMS score is at least 4 points.

In certain embodiments, dystonia is improved. In certain embodiments, gait is improved. In certain embodiments, postural instability is improved. In certain embodiments, treatment reduces the symptoms of parkinsonism.

In certain embodiments, the treatment does not worsen the subject's balance. In certain embodiments, the treatment improves balance.

In certain embodiments, the treatment improves physical functioning. In certain embodiments, the subject's physical functioning is improved as measured by the SF-36 physical functioning scale. In certain embodiments, the subject's physical functioning is improved as measured by the SF-36 physical functioning scale from baseline. In certain embodiments, the subject's physical functioning is improved as measured by the SF-36 physical functioning scale compared to untreated subjects.

In certain embodiments, the subject is much improved on the PGIC scale. In certain embodiments, the subject is very much improved on the PGIC scale. In certain embodiments, the subject is much improved on the CGIC scale. In certain embodiments, the subject is very much improved on the CGIC scale. In certain embodiments, the subject is much improved on the PGIC and CGIC scales. In certain embodiments, the subject is very much improved on the PGIC and CGIC scales.

In certain embodiments, the treatment improves swallowing.

In certain embodiments, treatment causes no significant increase in insomnia, depression, anxiety, agitation, suicidal ideation, akathisia, irritability, or fatigue.

In certain embodiments, treatment causes no significant parkinsonism or dysphagia.

In certain embodiments, the treatment does not significantly prolong the QT interval. In certain embodiments, the treatment does not significantly change the QTcF value. In certain embodiments, the maximal increases in QTcF is less than 5 ms.

Also provided are embodiments as recited in any of the embodiments above in paragraphs [089]-[0115], wherein either:
  chorea is reduced by at least 10% and any two or more of the following are true:
    motor function is improved by at least 10%;
    the subject's physical functioning is improved;
    swallowing is improved;
    balance is not worsened;
    treatment causes no significant increase in insomnia, depression, anxiety, agitation, suicidal ideation, akathisia, irritability, fatigue, parkinsonism or dysphagia; and
    the maximal increases in QTcF is less than 5 ms;
  or motor function is improved by at least 10%, and any two or more of the following are true:
    chorea is reduced by at least 10%;
    the subject's physical functioning is improved;
    swallowing is improved;
    balance is not worsened;
    treatment causes no significant increase in insomnia, depression, anxiety, agitation, suicidal ideation, akathisia, irritability, fatigue, parkinsonism or dysphagia; and
    the maximal increases in QTcF is less than 5 ms.

Also provided are embodiments as recited in any of the embodiments above in paragraphs [089]-[0115], wherein either:
  chorea is reduced by at least 10% and any three or more of the following are true:
    motor function is improved by at least 10%;
    the subject's physical functioning is improved;
    swallowing is improved;
    balance is not worsened;
    treatment causes no significant increase in insomnia, depression, anxiety, agitation, suicidal ideation, akathisia, irritability, fatigue, parkinsonism or dysphagia; and
    the maximal increases in QTcF is less than 5 ms;
  or motor function is improved by at least 10%, and any three or more of the following are true:
    chorea is reduced by at least 10%;
    the subject's physical functioning is improved;
    swallowing is improved;
    balance is not worsened;
    treatment causes no significant increase in insomnia, depression, anxiety, agitation, suicidal ideation, akathisia, irritability, fatigue, parkinsonism or dysphagia; and
    the maximal increases in QTcF is less than 5 ms.

Also provided are embodiments wherein any embodiment above in paragraphs [092]-[0120] above may be combined with any one or more of these embodiments, provided the combination is not mutually exclusive. Also provided is the use of a VMAT2 inhibitor for treating a movement disorder in a subject, as set forth herein or in any of the embodiments above in paragraphs [092]-[0120] above. Also provided is the use of a VMAT2 inhibitor in the manufacture of a medicament for treating a movement disorder in a subject, as set forth herein or in any of the embodiments above in paragraphs [092]-[0120] above. Also provided is a composition comprising a VMAT2 inhibitor for use in treating a movement disorder in a subject, as set forth herein or in any of the embodiments above in paragraphs [092]-[0120] above.

Also provided is a method of treating abnormal involuntary movement in a subject, comprising administering an initial daily amount of a VMAT2 inhibitor to the subject, in a manner that:
  a) adequately reduces the subject's abnormal involuntary movement; and
  b) improves one or more of the subject's symptoms of anxiety, swallowing, body weight, irritability, overall behavior, and compulsive behavior.

In further embodiments, the method comprises the additional steps of:
  c) determining after about one week the degree of control of abnormal involuntary movement achieved with the initial daily amount and the tolerability of the initial daily amount; and
  d) increasing the daily amount of the deuterium substituted tetrabenazine upward by 6 or more mg/day to a subsequent daily amount if the degree of control of abnormal involuntary movement is inadequate and the initial daily amount is tolerable;
  e) optionally, repeating steps b) and c) until the degree of control of abnormal involuntary movement is adequate and the daily amount of the deuterium substituted tetrabenazine is tolerable; and
  f) if any subsequent amount is intolerable, decreasing the daily amount downward by 6 or more mg/day to a subsequent daily amount.

Also provided is a method of treating abnormal involuntary movement in a subject, comprising administering a daily amount of deutetrabenazine to the subject, which:
  a) adequately reduces the subject's abnormal involuntary movement; and
  b) improves one or more of the subject's symptoms of depression, insomnia, somnolence, fatigue, dizziness, restlessness, agitation, akathisia, parkinsonism, nausea, anxiety, impaired swallowing, body weight gain, irritability, and compulsive behavior.

In certain embodiments, the method comprises the additional steps of:
  c) determining after about one week of treatment the degree of control of abnormal involuntary movement achieved with the daily amount of deutetrabenazine (the initial daily amount) and the tolerability of the initial daily amount; and
  d) increasing the daily amount of the deuterium substituted tetrabenazine upward by at least 6 mg/day to a subsequent daily amount if abnormal involuntary movement is not reduced and the initial daily amount is tolerated;
  e) after one week, optionally, repeating steps b) and c) provided that abnormal involuntary movement is reduced and the daily amount of the deuterium substituted tetrabenazine is tolerated; and
  f) if any subsequent amount is not tolerated, decreasing the daily amount downward by 6 mg/day to a subsequent daily amount.

In certain embodiments, the abnormal involuntary movement is a caused by a movement disorder.

In certain embodiments, the movement disorder is chosen from chorea associated with Huntington's disease, tardive dyskinesia, a tic associated with Tourette syndrome, dystonia, and and Parkinson's disease levodopa-induced dyskinesia.

In certain embodiments, the movement disorder is chosen from chorea associated with Huntington's disease, tardive dyskinesia, and tics associated with Tourette syndrome.

In certain embodiments, the movement disorder is chorea associated with Huntington's disease.

In certain embodiments, the abnormal muscular activity is a tic. In certain embodiments, the abnormal muscular activity is a tic associated with Tourette syndrome.

In certain embodiments, the daily amount of deutetrabenazine improves one or more of the subject's symptoms of anxiety, swallowing, body weight, irritability, overall behavior, and compulsive behavior. In certain embodiments, the movement disorder is chorea associated with Huntington's disease, and the daily amount of deutetrabenazine improves one or more of the subject's symptoms of depression, insomnia, somnolence, fatigue, dizziness, restlessness, agitation, akathisia, parkinsonism, nausea, anxiety, impaired swallowing, body weight gain, irritability, and compulsive behavior. In certain embodiments, the movement disorder is chosen from tardive dyskinesia and Tourette syndrome, and the daily amount of deutetrabenazine improves one or more of the subject's symptoms of depression, insomnia, somnolence, fatigue, dizziness, restlessness, agitation, akathisia, parkinsonism, nausea, anxiety, impaired swallowing, irritability, and compulsive behavior.

In certain embodiments, the absence of a reduction or suspension in an initial or subsequent daily amount indicates that the daily amount is tolerable. In certain embodiments, the tolerability is determined by assessment of one or more of the subject's levels of depression, anxiety, insomnia, somnolence, fatigue, dizziness, restlessness, agitation, irritability, akathisia, tardive dyskinesia, swallowing, parkinsonism, vomiting and nausea. In certain embodiments, a dose is not tolerated if one or more of the foregoing occur. In certain embodiments, a dose is not tolerated if somnolence or dizziness occur.

In certain embodiments, the VMAT2 inhibitor is a deuterium substituted tetrabenazine. In certain embodiments, the deuterium substituted tetrabenazine is deutetrabenazine. In certain embodiments, the deutetrabenazine is a plus isomeric form of deutetrabenazine. In certain embodiments, the plus isomeric form of deutetrabenazine is an alpha isomer. In certain embodiments, the VMAT2 inhibitor is a plus isomeric form of tetrabenazine. In certain embodiments, the plus isomeric form of tetrabenazine is an alpha isomer. In certain embodiments, the VMAT2 inhibitor is valbenazine.

In certain embodiments, the daily amount of deutetrabenazine is administered in one dose or two doses.

In certain embodiments, the initial daily amount of deutetrabenazine is chosen from about 6 mg, about 12 mg, about 18 mg, about 24 mg, about 30 mg, about 36 mg, about 42 mg, about 48 mg, about 54 mg, about 60 mg, about 66 mg, about 72 mg, and about 78 mg. In certain embodiments, the initial daily amount of deutetrabenazine is chosen from about 6 mg, about 12 mg, about 18 mg, about 24 mg, about 30 mg, about 36 mg, about 42 mg, and about 48 mg.

In certain embodiments, the initial daily amount of deutetrabenazine is administered in two doses, consisting of a first dose and a second dose.

In certain embodiments:
  the first dose about 6 mg and the second dose is about 6 mg;
  the first dose about 9 mg and the second dose is about 9 mg;
  the first dose about 12 mg and the second dose is about 12 mg;
  the first dose about 15 mg and the second dose is about 15 mg;
  the first dose about 18 mg and the second dose is about 18 mg;
  the first dose about 21 mg and the second dose is about 21 mg;
  the first dose about 24 mg and the second dose is about 24 mg;
  the first dose about 27 mg and the second dose is about 27 mg;
  the first dose about 30 mg and the second dose is about 30 mg;

the first dose about 33 mg and the second dose is about 33 mg;

the first dose about 36 mg and the second dose is about 36 mg; and the first dose about 39 mg and the second dose is about 39 mg.

In certain embodiments:

the first dose about 6 mg and the second dose is about 6 mg;

the first dose about 9 mg and the second dose is about 9 mg;

the first dose about 12 mg and the second dose is about 12 mg;

the first dose about 15 mg and the second dose is about 15 mg;

the first dose about 18 mg and the second dose is about 18 mg;

the first dose about 21 mg and the second dose is about 21 mg; and the first dose about 24 mg and the second dose is about 24 mg.

In certain embodiments, the daily amount of deutetrabenazine is about 6 mg to about 78 mg. In certain embodiments, the daily amount of deutetrabenazine is chosen from about 6 mg, about 12 mg, about 18 mg, about 24 mg, about 30 mg, about 36 mg, about 42 mg, about 48 mg, about 54 mg, about 60 mg, about 66 mg, about 72 mg, and about 78 mg. In certain embodiments, the daily amount of deutetrabenazine is chosen from about 6 mg, about 12 mg, about 18 mg, about 24 mg, about 30 mg, about 36 mg, about 42 mg, and about 48 mg.

In certain embodiments, the daily amount of deutetrabenazine administered is less than or equal to about 48 mg, or less than or equal to about 36 mg for subjects concurrently receiving a strong CYP2D6 inhibitor. In certain embodiments, the strong CYP2D6 inhibitor is chosen from fluoxetine, paroxetine, bupropion, quinidine, cinacalcet, and ritonavir. In certain embodiments, the strong CYP2D6 inhibitor is chosen from paroxetine, fluoxetine, and bupropion.

In certain embodiments, the chorea control is improved by a reduction of at least 0.5 points on the Total Maximal Chorea (TMC) score. In certain embodiments, the reduction in TMC score is at least 1 point. In certain embodiments, the reduction in TMC score is at least 1.5 points. In certain embodiments, the reduction in TMC score is at least 2.0 points. In certain embodiments, the reduction in TMC score is at least 2.5 points. In certain embodiments, the improvement is over a pre-treatment, "baseline" TMC score of at least 8.0. In certain embodiments, the improvement is over a pre-treatment, "baseline" TMC score of at least 10.0. In certain embodiments, the improvement is over a pre-treatment, "baseline" TMC score of at least 12.0. In certain embodiments, the improvement is over a pre-treatment, "baseline" TMC score of at least 12.7. In certain embodiments, the improvement is over a pre-treatment, "baseline" TMC score of at least 14.0.

In certain embodiments, chorea is reduced by at least 10%. In certain embodiments, chorea is reduced by at least 15%. In certain embodiments, chorea is reduced by at least 20%.

In certain embodiments, motor function is improved.

In certain embodiments, motor function is improved by a reduction of at least 1 point on the Total Motor Score (TMS). In certain embodiments, the reduction in TMS score is at least 2 points. In certain embodiments, the reduction in TMS score is at least 3 points. In certain embodiments, the reduction in TMS score is at least 4 points.

In certain embodiments, dystonia is improved. In certain embodiments, gait is improved. In certain embodiments, postural instability is improved. In certain embodiments, treatment reduces the symptoms of parkinsonism.

In certain embodiments, the treatment does not worsen the subject's balance. In certain embodiments, the treatment improves balance.

In certain embodiments, the treatment improves physical functioning. In certain embodiments, the subject's physical functioning is improved as measured by the SF-36 physical functioning scale. In certain embodiments, the subject's physical functioning is improved as measured by the SF-36 physical functioning scale from baseline. In certain embodiments, the subject's physical functioning is improved as measured by the SF-36 physical functioning scale compared to untreated subjects.

In certain embodiments, the subject is much improved on the PGIC scale. In certain embodiments, the subject is very much improved on the PGIC scale. In certain embodiments, the subject is much improved on the CGIC scale. In certain embodiments, the subject is very much improved on the CGIC scale. In certain embodiments, the subject is much improved on the PGIC and CGIC scales. In certain embodiments, the subject is very much improved on the PGIC and CGIC scales.

In certain embodiments, the treatment improves swallowing.

In certain embodiments, treatment causes no significant increase in insomnia, depression, anxiety, agitation, suicidal ideation, akathisia, irritability, or fatigue.

In certain embodiments, treatment causes no significant parkinsonism or dysphagia.

In certain embodiments, the treatment does not significantly prolong the QT interval. In certain embodiments, the treatment does not significantly change the QTcF value. In certain embodiments, the maximal increases in QTcF is less than 5 ms.

Also provided are embodiments wherein any embodiment above in paragraphs [0122]-[0152] above may be combined with any one or more of these embodiments, provided the combination is not mutually exclusive. Also provided is the use of a VMAT2 inhibitor for treating abnormal involuntary movement in a subject, as set forth herein or in any of the embodiments above in paragraphs [0122]-[0152] above. Also provided is the use of a VMAT2 inhibitor in the manufacture of a medicament for treating abnormal involuntary movement in a subject, as set forth herein or in any of the embodiments above in paragraphs [0122]-[0152] above. Also provided is a composition comprising a VMAT2 inhibitor for use in treating abnormal involuntary movement in a subject, as set forth herein or in any of the embodiments above in paragraphs [0122]-[0152] above.

Also provided is a method of reducing chorea and improving motor function in a subject with Huntington's disease, comprising the administration of a daily amount of a VMAT2 inhibitor.

In certain embodiments, the VMAT2 inhibitor is a deuterium substituted tetrabenazine. In certain embodiments, the deuterium substituted tetrabenazine is deutetrabenazine. In certain embodiments, the deutetrabenazine is a plus isomeric form of deutetrabenazine. In certain embodiments, the plus isomeric form of deutetrabenazine is an alpha isomer. In certain embodiments, the VMAT2 inhibitor is a plus isomeric form of tetrabenazine. In certain embodiments, the plus isomeric form of tetrabenazine is an alpha isomer. In certain embodiments, the VMAT2 inhibitor is valbenazine.

In certain embodiments, the daily amount of deutetrabenazine is administered in one dose or two doses.

In certain embodiments, the daily amount of deutetrabenazine is chosen from about 6 mg, about 12 mg, about 18 mg, about 24 mg, about 30 mg, about 36 mg, about 42 mg, about 48 mg, about 54 mg, about 60 mg, about 66 mg, about 72 mg, and about 78 mg. In certain embodiments, the daily amount of deutetrabenazine is chosen from about 6 mg, about 12 mg, about 18 mg, about 24 mg, about 30 mg, about 36 mg, about 42 mg, and about 48 mg.

In certain embodiments, the daily amount of deutetrabenazine is administered in two doses, consisting of a first dose and a second dose.

In certain embodiments:
the first dose about 6 mg and the second dose is about 6 mg;
the first dose about 9 mg and the second dose is about 9 mg;
the first dose about 12 mg and the second dose is about 12 mg;
the first dose about 15 mg and the second dose is about 15 mg;
the first dose about 18 mg and the second dose is about 18 mg;
the first dose about 21 mg and the second dose is about 21 mg;
the first dose about 24 mg and the second dose is about 24 mg;
the first dose about 27 mg and the second dose is about 27 mg;
the first dose about 30 mg and the second dose is about 30 mg;
the first dose about 33 mg and the second dose is about 33 mg;
the first dose about 36 mg and the second dose is about 36 mg; and
the first dose about 39 mg and the second dose is about 39 mg.

In certain embodiments:
the first dose about 6 mg and the second dose is about 6 mg;
the first dose about 9 mg and the second dose is about 9 mg;
the first dose about 12 mg and the second dose is about 12 mg;
the first dose about 15 mg and the second dose is about 15 mg;
the first dose about 18 mg and the second dose is about 18 mg;
the first dose about 21 mg and the second dose is about 21 mg; and
the first dose about 24 mg and the second dose is about 24 mg.

In certain embodiments, the daily amount of deutetrabenazine is about 6 mg to about 78 mg. In certain embodiments, the daily amount of deutetrabenazine administered is less than or equal to about 48 mg, or less than or equal to about 36 mg for subjects concurrently receiving a strong CYP2D6 inhibitor. In certain embodiments, the strong CYP2D6 inhibitor is chosen from fluoxetine, paroxetine, bupropion, quinidine, cinacalcet, and ritonavir. In certain embodiments, the strong CYP2D6 inhibitor is chosen from paroxetine, fluoxetine, and bupropion.

In certain embodiments, the chorea control is improved by a reduction of at least 0.5 points on the Total Maximal Chorea (TMC) score. In certain embodiments, the reduction in TMC score is at least 1 point. In certain embodiments, the reduction in TMC score is at least 1.5 points. In certain embodiments, the reduction in TMC score is at least 2.0 points. In certain embodiments, the reduction in TMC score is at least 2.5 points. In certain embodiments, the improvement is over a pre-treatment, "baseline" TMC score of at least 8.0. In certain embodiments, the improvement is over a pre-treatment, "baseline" TMC score of at least 10.0. In certain embodiments, the improvement is over a pre-treatment, "baseline" TMC score of at least 12.0. In certain embodiments, the improvement is over a pre-treatment, "baseline" TMC score of at least 12.7. In certain embodiments, the improvement is over a pre-treatment, "baseline" TMC score of at least 14.0.

In certain embodiments, chorea is reduced by at least 10%. In certain embodiments, chorea is reduced by at least 15%. In certain embodiments, chorea is reduced by at least 20%.

In certain embodiments, motor function is improved. In certain embodiments, motor function is improved by a reduction of at least 1 point on the Total Motor Score (TMS). In certain embodiments, the reduction in TMS score is at least 2 points. In certain embodiments, the reduction in TMS score is at least 3 points. In certain embodiments, the reduction in TMS score is at least 4 points.

In certain embodiments, dystonia is improved. In certain embodiments, gait is improved. In certain embodiments, postural instability is improved. In certain embodiments, treatment reduces the symptoms of parkinsonism.

In certain embodiments, the treatment does not worsen the subject's balance. In certain embodiments, the treatment improves balance.

In certain embodiments, the treatment improves physical functioning. In certain embodiments, the subject's physical functioning is improved as measured by the SF-36 physical functioning scale. In certain embodiments, the subject's physical functioning is improved as measured by the SF-36 physical functioning scale from baseline. In certain embodiments, the subject's physical functioning is improved as measured by the SF-36 physical functioning scale compared to untreated subjects.

In certain embodiments, the subject is much improved on the PGIC scale. In certain embodiments, the subject is very much improved on the PGIC scale. In certain embodiments, the subject is much improved on the CGIC scale. In certain embodiments, the subject is very much improved on the CGIC scale. In certain embodiments, the subject is much improved on the PGIC and CGIC scales. In certain embodiments, the subject is very much improved on the PGIC and CGIC scales.

In certain embodiments, the treatment improves swallowing.

In certain embodiments, treatment causes no significant increase in insomnia, depression, anxiety, agitation, suicidal ideation, akathisia, irritability, or fatigue.

In certain embodiments, treatment causes no significant parkinsonism or dysphagia.

In certain embodiments, the treatment does not significantly prolong the QT interval. In certain embodiments, the treatment does not significantly change the QTcF value. In certain embodiments, the maximal increases in QTcF is less than 5 ms.

Also provided are embodiments wherein any embodiment above in paragraphs [0154]-[0173] above may be combined with any one or more of these embodiments, provided the combination is not mutually exclusive. Also provided is the use of a VMAT2 inhibitor for chorea and improving motor function in a subject with Huntington's disease, as set forth herein or in any of the embodiments above in paragraphs [0154]-[0173] above. Also provided is the use of a VMAT2 inhibitor in the manufacture of a medicament for chorea and improving motor function in a subject with Huntington's disease, as set forth herein or in any of the embodiments above in paragraphs [0154]-[0173] above. Also provided is a composition comprising a VMAT2 inhibitor for use in chorea and improving motor function in a subject with Huntington's disease, as set forth herein or in any of the embodiments above in paragraphs [0154]-[0173] above.

Also provided is a method of improving motor function in a subject with Huntington's disease, tardive dyskinseia, or Tourette syndrome, comprising the administration of about a daily amount of a VMAT2 inhibitor. In certain embodiments, the VMAT2 inhibitor is a deuterium substituted tetrabenazine.

In certain embodiments, the subject has Huntington's disease. In certain embodiments, the subject has tardive dyskinseia. In certain embodiments, the subject has Tourette syndrome.

In certain embodiments, the deuterium substituted tetrabenazine is deutetrabenazine. In certain embodiments, the deutetrabenazine is a plus isomeric form of deutetrabenazine. In certain embodiments, the plus isomeric form of deutetrabenazine is an alpha isomer. In certain embodiments, the VMAT2 inhibitor is a plus isomeric form of tetrabenazine. In certain embodiments, the plus isomeric form of tetrabenazine is an alpha isomer.

In certain embodiments, the VMAT2 inhibitor is valbenazine.

In certain embodiments, the daily amount of deutetrabenazine is administered in one dose or two doses.

In certain embodiments, the daily amount of deutetrabenazine is chosen from about 6 mg, about 12 mg, about 18 mg, about 24 mg, about 30 mg, about 36 mg, about 42 mg, about 48 mg, about 54 mg, about 60 mg, about 66 mg, about 72 mg, and about 78 mg. In certain embodiments, the daily amount of deutetrabenazine is chosen from about 6 mg, about 12 mg, about 18 mg, about 24 mg, about 30 mg, about 36 mg, about 42 mg, and about 48 mg.

In certain embodiments, the daily amount of deutetrabenazine is administered in two doses, consisting of a first dose and a second dose.

In certain embodiments:
the first dose about 6 mg and the second dose is about 6 mg;
the first dose about 9 mg and the second dose is about 9 mg;
the first dose about 12 mg and the second dose is about 12 mg;
the first dose about 15 mg and the second dose is about 15 mg;
the first dose about 18 mg and the second dose is about 18 mg;
the first dose about 21 mg and the second dose is about 21 mg;
the first dose about 24 mg and the second dose is about 24 mg;
the first dose about 27 mg and the second dose is about 27 mg;
the first dose about 30 mg and the second dose is about 30 mg;
the first dose about 33 mg and the second dose is about 33 mg;
the first dose about 36 mg and the second dose is about 36 mg; and
the first dose about 39 mg and the second dose is about 39 mg.

In certain embodiments:
the first dose about 6 mg and the second dose is about 6 mg;
the first dose about 9 mg and the second dose is about 9 mg;
the first dose about 12 mg and the second dose is about 12 mg;
the first dose about 15 mg and the second dose is about 15 mg;
the first dose about 18 mg and the second dose is about 18 mg;
the first dose about 21 mg and the second dose is about 21 mg; and
the first dose about 24 mg and the second dose is about 24 mg.

In certain embodiments, the daily amount of deutetrabenazine is about 6 mg to about 78 mg. In certain embodiments, the daily amount of deutetrabenazine is chosen from about 6 mg, about 12 mg, about 18 mg, about 24 mg, about 30 mg, about 36 mg, about 42 mg, about 48 mg, about 54 mg, about 60 mg, about 66 mg, about 72 mg, and about 78 mg. In certain embodiments, the daily amount of deutetrabenazine is chosen from about 6 mg, about 12 mg, about 18 mg, about 24 mg, about 30 mg, about 36 mg, about 42 mg, and about 48 mg. In certain embodiments, the daily amount of deutetrabenazine administered is less than or equal to about 48 mg, or less than or equal to about 36 mg for subjects concurrently receiving a strong CYP2D6 inhibitor. In certain embodiments, the strong CYP2D6 inhibitor is chosen from fluoxetine, paroxetine, bupropion, quinidine, cinacalcet, and ritonavir. In certain embodiments, the strong CYP2D6 inhibitor is chosen from paroxetine, fluoxetine, and bupropion.

In certain embodiments, the chorea control is improved by a reduction of at least 0.5 points on the Total Maximal Chorea (TMC) score. In certain embodiments, the reduction in TMC score is at least 1 point. In certain embodiments, the reduction in TMC score is at least 1.5 points. In certain embodiments, the reduction in TMC score is at least 2.0 points. In certain embodiments, the reduction in TMC score is at least 2.5 points. In certain embodiments, the improvement is over a pre-treatment, "baseline" TMC score of at least 8.0. In certain embodiments, the improvement is over a pre-treatment, "baseline" TMC score of at least 10.0. In certain embodiments, the improvement is over a pre-treatment, "baseline" TMC score of at least 12.0. In certain embodiments, the improvement is over a pre-treatment, "baseline" TMC score of at least 12.7. In certain embodiments, the improvement is over a pre-treatment, "baseline" TMC score of at least 14.0.

In certain embodiments, chorea is reduced by at least 10%. In certain embodiments, chorea is reduced by at least 15%. In certain embodiments, chorea is reduced by at least 20%.

In certain embodiments, motor function is improved.

In certain embodiments, motor function is improved by a reduction of at least 1 point on the Total Motor Score (TMS). In certain embodiments, the reduction in TMS score is at least 2 points. In certain embodiments, the reduction in TMS score is at least 3 points. In certain embodiments, the reduction in TMS score is at least 4 points.

In certain embodiments, dystonia is improved. In certain embodiments, gait is improved. In certain embodiments, postural instability is alleviated. In certain embodiments, treatment reduces the symptoms of parkinsonism.

In certain embodiments, the treatment does not worsen the subject's balance. In certain embodiments, the treatment improves balance.

In certain embodiments, the subject is much improved on the PGIC scale. In certain embodiments, the subject is very much improved on the PGIC scale. In certain embodiments, the subject is much improved on the CGIC scale. In certain embodiments, the subject is very much improved on the CGIC scale. In certain embodiments, the subject is much improved on the PGIC and CGIC scales. In certain embodiments, the subject is very much improved on the PGIC and CGIC scales.

In certain embodiments, the treatment improves physical functioning. In certain embodiments, the subject's physical functioning is improved as measured by the SF-36 physical functioning scale. In certain embodiments, the subject's physical functioning is improved as measured by the SF-36 physical functioning scale from baseline. In certain embodiments, the subject's physical functioning is improved as measured by the SF-36 physical functioning scale compared to untreated subjects.

In certain embodiments, the treatment improves swallowing.

In certain embodiments, treatment causes no significant increase in insomnia, depression, anxiety, agitation, suicidal ideation, akathisia, irritability, or fatigue.

In certain embodiments, treatment causes no significant parkinsonism or dysphagia.

In certain embodiments, the treatment does not significantly prolong the QT interval. In certain embodiments, the treatment does not significantly change the QTcF value. In certain embodiments, the maximal increases in QTcF is less than 5 ms.

Also provided are embodiments wherein any embodiment above in paragraphs [0175]-[0196] above may be combined with any one or more of these embodiments, provided the combination is not mutually exclusive. Also provided is the use of deutetrabenazine, or a VMAT2 inhibitor, for improving motor function in a subject with Huntington's disease, tardive dyskinseia, or Tourette syndrome, as set forth herein or in any of the embodiments above in paragraphs [0175]-[0196] above. Also provided is the use of deutetrabenazine, or a VMAT2 inhibitor, in the manufacture of a medicament for improving motor function in a subject with Huntington's disease, tardive dyskinseia, or Tourette syndrome, as set forth herein or in any of the embodiments above in paragraphs [0175]-[0196] above. Also provided is a composition comprising deutetrabenazine, or a VMAT2 inhibitor, for use in improving motor function in a subject with Huntington's disease, tardive dyskinseia, or Tourette syndrome, as set forth herein or in any of the embodiments above in paragraphs [0175]-[0196] above.

Also provided is a method of reducing motor or phonic tics in a subject with Tourette syndrome, comprising the administration of about a daily amount of deutetrabenazine.

In certain embodiments, the tics are motor tics.

In certain embodiments, the tics are phonic tics.

In certain embodiments, the subject is between 6 and 16 years of age. In certain embodiments, the subject is between 12 and 18 years of age. In certain embodiments, the subject is between 6 and 18 years of age.

In certain embodiments, the daily amount of deutetrabenazine is about 6 mg to about 48 mg. In certain embodiments, the daily amount of deutetrabenazine is chosen from about 6 mg, about 12 mg, about 18 mg, about 24 mg, about 30 mg, about 36 mg, about 42 mg, and about 48 mg. In certain embodiments, the daily amount of deutetrabenazine administered is less than or equal to about 48 mg, or less than or equal to about 36 mg for subjects concurrently receiving a strong CYP2D6 inhibitor. In certain embodiments, the strong CYP2D6 inhibitor is chosen from fluoxetine, paroxetine, bupropion, quinidine, cinacalcet, and ritonavir. In certain embodiments, the strong CYP2D6 inhibitor is chosen from paroxetine, fluoxetine, and bupropion.

In certain embodiments, the daily amount of deutetrabenazine is administered with food.

In certain embodiments, the daily amount of deutetrabenazine is split into at least two doses.

In certain embodiments, the daily amount of deutetrabenazine is administered in two equal doses, consisting of a first dose and a second dose.

In certain embodiments, the motor or phonic tics are reduced ≥25% as measured by the Total Tic Score of the Yale Global Tic Severity Scale.

In certain embodiments, the motor or phonic tics are reduced by 2 or more points on the Tourette Syndrome Clinical Global Impression (TS-CGI).

In certain embodiments, the motor or phonic tics are reduced by 1 or more points on the Tourette Syndrome Patient Global Impression of severity (TS-PGIS). In certain embodiments, the motor or phonic tics are reduced by 2 or more points on the Tourette Syndrome Patient Global Impression of severity (TS-PGIS).

In certain embodiments, the reduction is from baseline to at least two weeks.

In certain embodiments, the reduction is from baseline to at least four weeks. In certain embodiments, the reduction is from baseline to at least eight weeks. In certain embodiments, the reduction is from baseline to at least twelve weeks.

Also provided are embodiments wherein any embodiment above in paragraphs [0198]-[0211] above may be combined with any one or more of these embodiments, provided the combination is not mutually exclusive. Also provided is the use of deutetrabenazine, or a VMAT2 inhibitor, for reducing motor or phonic tics in a subject with Tourette syndrome, as set forth herein or in any of the embodiments above in paragraphs [0198]-[0211] above. Also provided is the use of deutetrabenazine, or a VMAT2 inhibitor, in the manufacture of a medicament for reducing motor or phonic tics in a subject with Tourette syndrome, as set forth herein or in any of the embodiments above in paragraphs [0198]-[0211] above. Also provided is a composition comprising deutetrabenazine, or a VMAT2 inhibitor, for use in reducing motor or phonic tics in a subject with Tourette syndrome, as set forth herein or in any of the embodiments above in paragraphs [0198]-[0211] above.

Also provided is a method of reducing motor and phonic tics in a subject with Tourette syndrome, comprising the administration of about a daily amount of deutetrabenazine.

In certain embodiments, the daily amount of deutetrabenazine is about 6 mg to about 48 mg. In certain embodiments, the daily amount of deutetrabenazine is between 6 and 48 mg. In certain embodiments, the daily amount of deutetrabenazine is chosen from about 6 mg, about 12 mg, about 18 mg, about 24 mg, about 30 mg, about 36 mg, about 42 mg, and about 48 mg. In certain embodiments, the daily amount of deutetrabenazine administered is less than or equal to about 48 mg, or less than or equal to about 36 mg for subjects concurrently receiving a strong CYP2D6 inhibitor. In certain embodiments, the strong CYP2D6 inhibitor is chosen from fluoxetine, paroxetine, bupropion, quinidine, cinacalcet, and ritonavir. In certain embodiments, the strong CYP2D6 inhibitor is chosen from paroxetine, fluoxetine, and bupropion.

In certain embodiments, the daily amount of deutetrabenazine is administered with food.

In certain embodiments, the daily amount of deutetrabenazine is split into at least two doses.

In certain embodiments, the daily amount of deutetrabenazine is administered in two equal doses, consisting of a first dose and a second dose.

In certain embodiments, the subject is between 6 and 16 years of age. In certain embodiments, the subject is between 12 and 18 years of age. In certain embodiments, the subject is between 6 and 18 years of age.

In certain embodiments, the motor and phonic tics are reduced ≥25% as measured by the Total Tic Score of the Yale Global Tic Severity Scale.

In certain embodiments, the motor or phonic tics are reduced by 2 or more points on the Tourette Syndrome Clinical Global Impression.

In certain embodiments, the reduction is from baseline to at least two weeks. In certain embodiments, the reduction is from baseline to at least four weeks. In certain embodiments, the reduction is from baseline to at least eight weeks. In certain embodiments, the reduction is from baseline to at least twelve weeks.

In certain embodiments, the deutetrabenazine is a plus isomeric form of deutetrabenazine. In certain embodiments, the plus isomeric form of deutetrabenazine is an alpha isomer.

In certain embodiments, the treatment does not significantly prolong the QT interval. In certain embodiments, the treatment does not significantly change the QTcF value. In certain embodiments, the maximal increases in QTcF is less than 5 ms.

Also provided are embodiments wherein any embodiment above in paragraphs [0213]-[0223] above may be combined with any one or more of these embodiments, provided the combination is not mutually exclusive. Also provided is the use of deutetrabenazine, or a VMAT2 inhibitor, for reducing motor and phonic tics in a subject with Tourette syndrome, as set forth herein or in any of the embodiments above in paragraphs [0213]-[0223] above. Also provided is the use of deutetrabenazine, or a VMAT2 inhibitor, in the manufacture of a medicament for reducing motor and phonic tics in a subject with Tourette syndrome, as set forth herein or in any of the embodiments above in paragraphs [0213]-[0223] above. Also provided is a composition comprising deutetrabenazine, or a VMAT2 inhibitor, for use in reducing motor and phonic tics in a subject with Tourette syndrome, as set forth herein or in any of the embodiments above in paragraphs [0213]-[0223] above.

Also provided is a method of reducing tic severity as measured by the subject's Tourette Syndrome Patient Global Impression of Severity (TS-PGIS) in a subject with Tourette syndrome, comprising the administration of about a daily amount of deutetrabenazine. In certain embodiments, the method comprises: a) administering a daily amount of deutetrabenazine; and b) at least once every 4 weeks, assessing tic severity using the TS-PGIS. In further embodiments, the method additionally comprises: c) after assessing tic severity using the TS-PGIS, if the daily amount of deutetrabenazine is tolerable, increasing the daily amount of deutetrabenazine by at least 6 mg/day; d) repeating steps b) and c) until TS-PGIS is not further reduced or the daily amount of the deutetrabenazine is tolerated; and e) if any subsequent amount is not tolerated, decreasing the daily amount of deutetrabenazine downward by 6 mg/day.

In certain embodiments, the tics are motor tics.
In certain embodiments, the tics are phonic tics.
In certain embodiments, the subject is between 6 and 16 years of age. In certain embodiments, the subject is between 12 and 18 years of age. In certain embodiments, the subject is between 6 and 18 years of age.

In certain embodiments, the daily amount of deutetrabenazine is between 6 and 48 mg. In certain embodiments, the daily amount of deutetrabenazine is chosen from about 6 mg, about 12 mg, about 18 mg, about 24 mg, about 30 mg, about 36 mg, about 42 mg, and about 48 mg. In certain embodiments, the daily amount of deutetrabenazine is administered with food.

In certain embodiments, tic severity is assessed using the TS-PGIS at least every two weeks. In certain embodiments, tic severity is assessed using the TS-PGIS at least weekly. In certain embodiments, tic severity is assessed using the TS-PGIS at least monthly. In certain embodiments, tic severity is assessed using the TS-PGIS at least every three months.

In certain embodiments, the daily amount of deutetrabenazine is split into two doses.

In certain embodiments, the reduction is from baseline to at least two weeks. In certain embodiments, the reduction is from baseline to at least four weeks. In certain embodiments, the reduction is from baseline to at least eight weeks. In certain embodiments, the reduction is from baseline to at least twelve weeks.

In certain embodiments, the deutetrabenazine is a plus isomeric form of deutetrabenazine. In certain embodiments, the plus isomeric form of deutetrabenazine is an alpha isomer.

In certain embodiments, the treatment does not significantly prolong the QT interval. In certain embodiments, the treatment does not significantly change the QTcF value. In certain embodiments, the maximal increases in QTcF is less than 5 ms.

Also provided are embodiments wherein any embodiment above in paragraphs [0213]-[0234] above may be combined with any one or more of these embodiments, provided the combination is not mutually exclusive. Also provided is the use of deutetrabenazine for reducing tic severity as measured by the subject's Tourette Syndrome Patient Global Impression of Severity (TS-PGIS), as set forth herein or in any of the embodiments above in paragraphs [0213]-[0234] above. Also provided is the use of deutetrabenazine in the manufacture for reducing tic severity as measured by the subject's Tourette Syndrome Patient Global Impression of Severity (TS-PGIS), as set forth herein or in any of the embodiments above in paragraphs [0213]-[0234] above. Also provided is a composition comprising deutetrabenazine for use in reducing tic severity as measured by the subject's Tourette Syndrome Patient Global Impression of Severity (TS-PGIS), as set forth herein or in any of the embodiments above in paragraphs [0213]-[0234] above.

Also provided is a method of maintaining control of abnormal involuntary movements in a human subject with a movement disorder, comprising administering to the subject a therapeutically effective daily amount of deutetrabenazine for a period of time sufficient to do one or more of the following: reduce chorea by at least 10%; improve motor function by at least 10%; improve physical functioning; improve swallowing; improve balance; reduce abnormal involuntary movements in subjects with tardive dyskinesia; reduce motor tics; reduce vocal/phonic tics; reduce motor and vocal/phonic tics; reduce impairment in subjects with Tourette syndrome; reduce the severity of Tourette syndrome; reduce the patient global impression of severity in subjects with Tourette Syndrome; and much or very much improve the subject's patient of clinical global impression of change.

In certain embodiments, the disorder is chosen from Huntington's disease, tardive dyskinesia, and Tourette syndrome.

In certain embodiments, or improvement in each of the endpoints above is measured as follows: reduction in chorea is measured by the Unified Huntington's Disease Rating Scale (UHDRS) or a subscale thereof; reduction in chorea is measured by the Total Maximal Chorea (TMC) score of the UHDRS; improvement in motor function is measured by the Total Motor Score (TMS) score of the UHDRS; improvement in physical functioning is measured by the SF-36 physical functioning scale; improvement in swallowing is measured by the Swallowing Disturbance Questionnaire (SDQ); improvement in balance is measured by the Berg Balance Test (BBT); reduction in abnormal involuntary movements in subjects with tardive dyskinesia is measured by the AIMS; reduction in motor tics in subjects with Tourette Syndrome is measured by the MTSS of the YGTSS; reduction in vocal/phonic tics in subjects with Tourette Syndrome is measured by the VTSS of the YGTSS; reduction in total (motor and vocal/phonic) tics is measured by the TTS of the YGTSS; reduction in impairment is measured by the Impairment score of the YGTSS; reduction in the severity of Tourette syndrome is measured by the the global severity score of the YGTSS; and reduction in patient global impression of severity in subjects with Tourette Syndrome is measured by the TS-PGIS.

In certain embodiments, the daily amount of deutetrabenazine is about 6 mg to about 78 mg. In certain embodiments, the daily amount of deutetrabenazine is chosen from about 6 mg, about 12 mg, about 18 mg, about 24 mg, about 30 mg, about 36 mg, about 42 mg, about 48 mg, about 54 mg, about 60 mg, about 66 mg, about 72 mg, and about 78 mg. In certain embodiments, the daily amount of deutetrabenazine is chosen from about 6 mg, about 12 mg, about 18 mg, about 24 mg, about 30 mg, about 36 mg, about 42 mg, and about 48 mg. In certain embodiments, the daily amount of deutetrabenazine administered is less than or equal to about 48 mg, or less than or equal to about 36 mg for subjects concurrently receiving a strong CYP2D6 inhibitor. In certain embodiments, the strong CYP2D6 inhibitor is chosen from fluoxetine, paroxetine, bupropion, quinidine, cinacalcet, and ritonavir. In certain embodiments, the strong CYP2D6 inhibitor is chosen from paroxetine, fluoxetine, and bupropion.

In certain embodiments, the sufficient period of time is at least four weeks. In certain embodiments, the sufficient period of time is at least eight weeks. In certain embodiments, the sufficient period of time is at least twelve weeks.

In certain embodiments, the reduction or improvement in the relevant measure or measures is by at least 10% over baseline. In certain embodiments, the reduction or improvement in the relevant measure or at least one of the measures is by at least 20% over baseline. In certain embodiments, the reduction or improvement in the relevant measure or at least one of the measures is by at least 30% over baseline. In certain embodiments, the reduction or improvement in the relevant measure or at least one of the measures is by at least 40% over baseline. In certain embodiments, the reduction or improvement in the relevant measure or at least one of the measures is by at least 50% over baseline.

In certain embodiments, the disorder is Huntington's disease. In certain embodiments, the abnormal involuntary movement is chorea associated with Huntington's disease.

In certain embodiments, the disorder is tardive dyskinesia.

In certain embodiments, the disorder is Tourette syndrome. In certain embodiments, the abnormal involuntary movement is a tic associated with Tourette syndrome.

In certain embodiments, the deutetrabenazine is a plus isomeric form of deutetrabenazine. In certain embodiments, the plus isomeric form of deutetrabenazine is an alpha isomer.

In certain embodiments, the treatment does not significantly prolong the QT interval. In certain embodiments, the treatment does not significantly change the QTcF value. In certain embodiments, the maximal increases in QTcF is less than 5 ms.

Also provided are embodiments wherein any embodiment above in paragraphs [0238]-[0246] above may be combined with any one or more of these embodiments, provided the combination is not mutually exclusive. Also provided is the use of deutetrabenazine for maintaining control of abnormal involuntary movements in a human subject with a movement disorder, as set forth herein or in any of the embodiments above in paragraphs [0238]-[0246] above. Also provided is the use of deutetrabenazine in the manufacture of a medicament for maintaining control of abnormal involuntary movements in a human subject with a movement disorder, as set forth herein or in any of the embodiments above in paragraphs [0238]-[0246] above. Also provided is a composition comprising deutetrabenazine for maintaining control of abnormal involuntary movements in a human subject with a movement disorder, as set forth herein or in any of the embodiments above in paragraphs [0238]-[0246] above.

Compositions

Tetrabenazine (Nitoman, Xenazine, Ro 1-9569), 1,3,4,6, 7,11b-Hexahydro-9,10-dimethoxy-3-(2-methylpropyl)-2H-benzo[a]quinoline, is a vesicular monoamine transporter 2 (VMAT2) inhibitor. Tetrabenazine is commonly prescribed for the treatment of Huntington's disease (Savani et al., *Neurology* 2007, 68(10), 797; and Kenney et al., *Expert Review of Neurotherapeutics* 2006, 6(1), 7-17). Tetrabenazine is subject to extensive oxidative metabolism, including O-demethylation of the methoxy groups, as well as hydroxylation of the isobutyl group (Schwartz et al., *Biochem. Pharmacol.*, 1966, 15, 645-655). Adverse effects associated with the administration of tetrabenazine include neuroleptic malignant syndrome, drowsiness, fatigue, nervousness, anxiety, insomnia, agitation, confusion, orthostatic hypotension, nausea, dizziness, depression, and Parkinsonism.

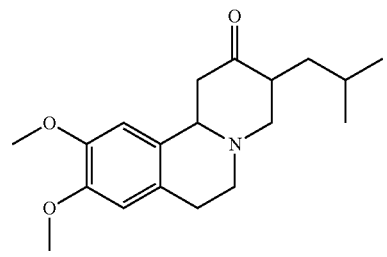

Tetrabenazine

Deuterium Enriched Tetrabenazine Analogues d$_6$-Tetrabenazine (equivalently, deutetrabenazine, SD-809, or DTBZ) is a deuterated analog of tetrabenazine currently under clinical development. U.S. Pat. No. 8,524,733, US 20100130480, and US 20120003330.

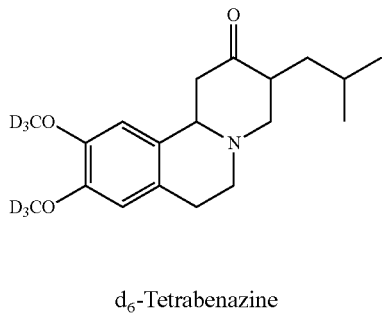

d$_6$-Tetrabenazine (RR, SS)-1,3,4,6,7,11b-hexahydro-9,10-di(methoxy-d$_3$)-3-(2-methylpropyl)-2H-benzo[a]quinolizin-2-one In all of the the methods and compositions disclosed herein using deutetrabenazine, the deutetrabenazine may be administered or formulated as part of a pharmaceutical composition wherein the composition has deuterium enrichment of at least 90% at each of the positions designated D. In certain embodiments, the composition has deuterium enrichment of at least 95% at each of the positions designated D. In certain embodiments, the composition has deuterium enrichment of at least 98% at each of the positions designated D.

In humans, as shown below, d$_6$-tetrabenazine is rapidly and extensively converted in the liver (similarly to non-isotopically enriched tetrabenazine) to major, active dihydrotetrabenazine (HTBZ) metabolites referred to as d$_6$-α-HTBZ and d$_6$-β-HTBZ (as a mixture of the + and − isomers) which have the structures below (+isomers shown). These metabolites are believed to drive clinical efficacy.

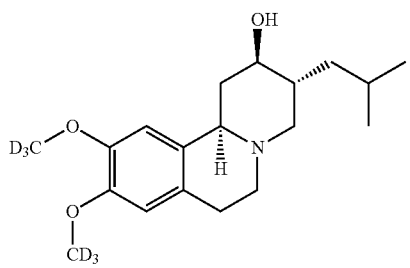

d$_6$-α-HTBZ

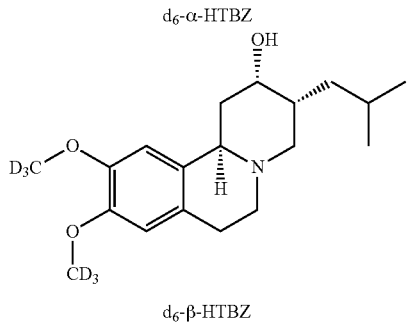

d$_6$-β-HTBZ

Deuterium substituted tetrabenazines include, in addition to deutetrabenazine disclosed above, compounds as disclosed in U.S. Pat. No. 8,524,733, US 20100130480, and US 20120003330, and PCT/US2014/066740, filed Nov. 14, 2014. Examples of such compounds are given in the following structural formulas.

In certain embodiments of the present invention, compounds have structural Formula I:

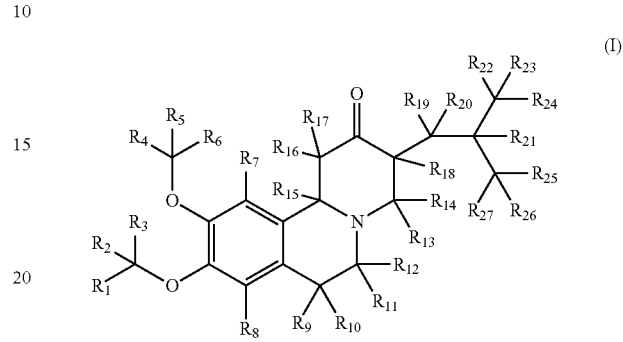

or a salt, solvate, or prodrug thereof, wherein:
R$_1$-R$_{27}$ are independently selected from the group consisting of hydrogen and deuterium; and
at least one of R$_1$-R$_{27}$ is deuterium.

In certain embodiments, Formula I can include a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof.

In certain embodiments of the present invention, compounds have structural Formula II:

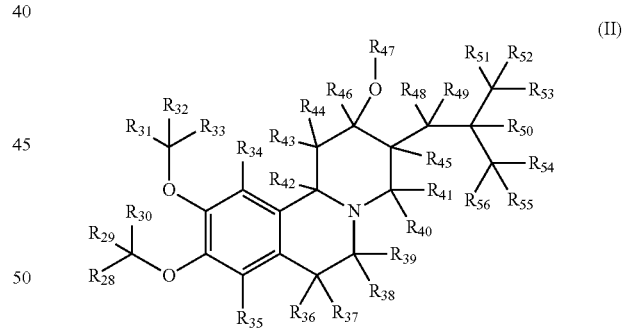

or a salt thereof, wherein:
R$_{28}$-R$_{46}$ and R$_{48}$-R$_{56}$ are independently selected from the group consisting of hydrogen and deuterium;
R$_{47}$ is selected from the group consisting of hydrogen, deuterium, —C(O)O-alkyl and —C(O)—C$_{1-6}$alkyl, or a group cleavable under physiological conditions, wherein said alkyl or C$_{1-6}$alkyl is optionally substituted with one or more substituents selected from the group consisting of —NH—C(NH)NH2, —CO$_2$H, —CO$_2$alkyl, —SH, —C(O)NH$_2$, —NH$_2$, phenyl, —OH, 4-hydroxyphenyl, imidazolyl, and indolyl, and any R$_{46}$ substituent is further optionally substituted with deuterium; and
at least one of R$_{28}$-R$_{56}$ is deuterium or contains deuterium.

In certain embodiments, the compounds of Formula II have alpha stereochemistry.

In further embodiments, the compounds of Formula II have beta stereochemistry.

In yet further embodiments, the compounds of Formula II are a mixture of alpha and beta stereoisomers. In yet further embodiments, the ratio of alpha/beta stereoisomers is at least 100:1, at least 50:1, at least 20:1, at least 10:1, at least 5:1, at least 4:1, at least 3:1, or at least 2:1. In yet further embodiments, the ratio of beta/alpha stereoisomers is at least 100:1, at least 50:1, at least 20:1, at least 10:1, at least 5:1, at least 4:1, at least 3:1, or at least 2:1.

In certain embodiments, if $R_{50}$-$R_{56}$ are deuterium, at least one of $R_1$-$R_{49}$ is deuterium.

In certain embodiments of the present invention, compounds have structural Formula III:

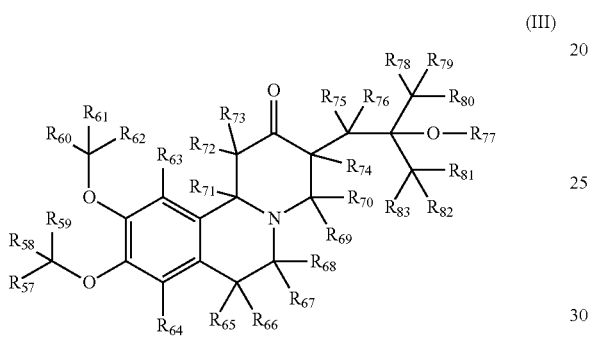

(III)

or a salt, stereoisomer, or racemic mixture thereof, wherein:
$R_{57}$-$R_{83}$ are independently selected from the group consisting of hydrogen and deuterium; and
at least one of $R_{57}$-$R_{83}$ is deuterium.

In certain embodiments of the present invention, compounds have structural Formula IV:

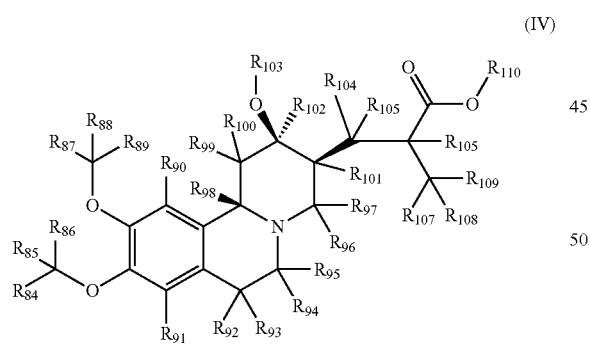

(IV)

or a salt, diastereomer, or mixture of diastereomers thereof, wherein:
$R_{84}$-$R_{110}$ are independently selected from the group consisting of hydrogen and deuterium; and
at least one of $R_{84}$-$R_{110}$ is deuterium.

Deuterium substituted tetrabenazine metabolites include, in addition to $d_6$-α-HTBZ and $d_6$-β-HTBZ disclosed above, compounds disclosed in of the following structural formulas.

The terms "alpha-dihydrotetrabenazine", "α-dihydrotetrabenazine", or the terms "alpha" or "alpha stereoisomer" or the symbol "α" as applied to dihydrotetrabenazine refers to either of the dihydrotetrabenazine stereoisomers having the structural formulas shown below, or a mixture thereof:

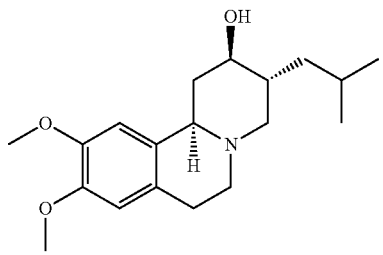

(+)-alpha-dihydrotetrabenazine

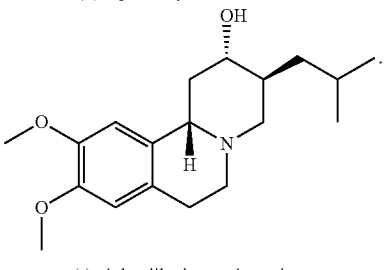

(-)-alpha-dihydrotetrabenazine

The terms "alpha" or "alpha stereoisomer" or the symbol "α" as applied to a compound of Formula II refers to either of the stereoisomers of compounds of Formula II shown below, or a mixture thereof:

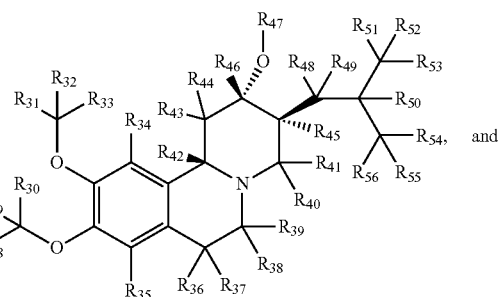

and

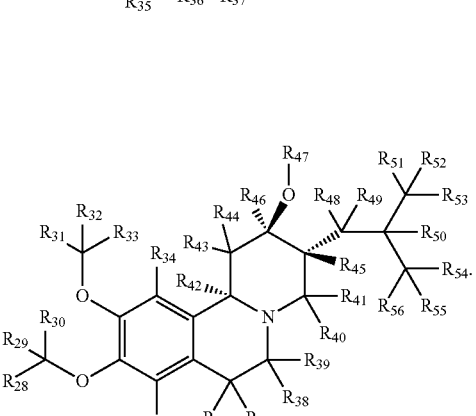

The terms "beta-dihydrotetrabenazine", "β-dihydrotetrabenazine", or the terms "beta" or "beta stereoisomer" or the symbol "β" as applied to dihydrotetrabenazine refers to either of the dihydrotetrabenazine stereoisomers having the structural formulas shown below, or a mixture thereof:

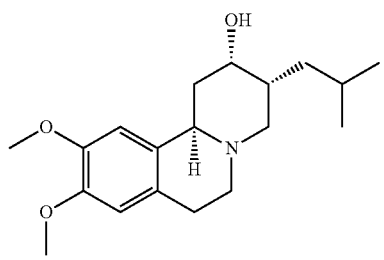

(+)-beta-dihydrotetrabenazine

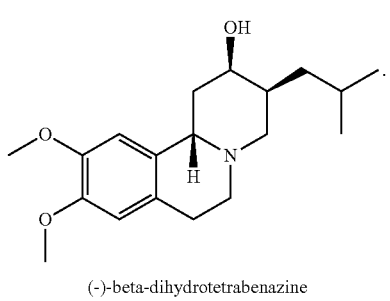

(-)-beta-dihydrotetrabenazine

The terms "beta" or "beta stereoisomer" or the symbol "β" as applied to a compound of Formula II refers to either of the stereoisomers of compounds of Formula II shown below, or a mixture thereof:

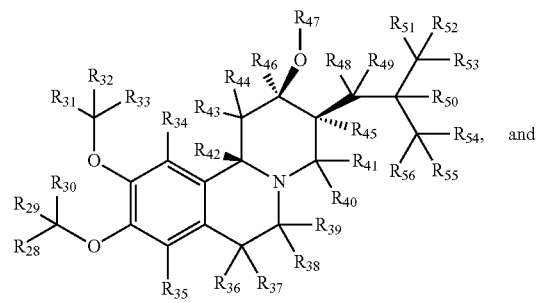

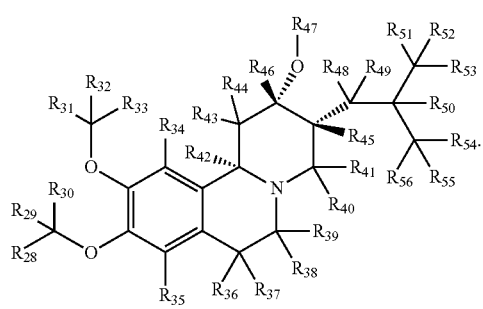

The terms "3S,11bS enantiomer" or the term "3R,11bR enantiomer" refers to either of the $d_6$-tetrabenazine M4 metabolite stereoisomers having the structural formulas shown below:

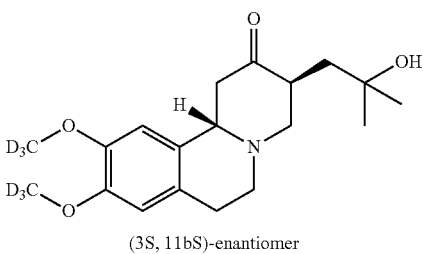

(3S, 11bS)-enantiomer

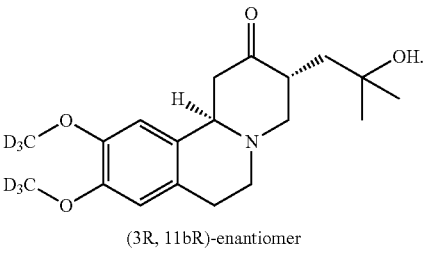

(3R, 11bR)-enantiomer

In certain embodiments, a chemical structure may be drawn as either the 3S,11bS enantiomer or the 3R,11bR enantiomer, but the text of the specification may indicate that the 3S,11bS enantiomer, the 3R,11bR enantiomer, a racemic mixture thereof, or all of the foregoing may be intended to be described.

The terms "(3S, 11bS)-enantiomer" or "(3R, 11bR)-enantiomer" or the as applied to a compound of Formula I refers to either of the stereoisomers of compounds of Formula III shown below:

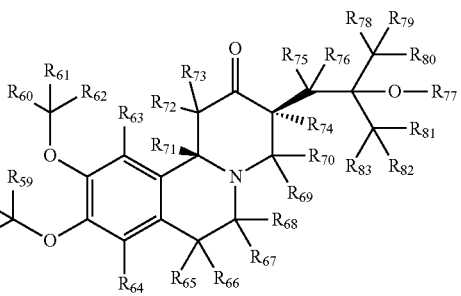

(3S, 11bS)-enantiomer

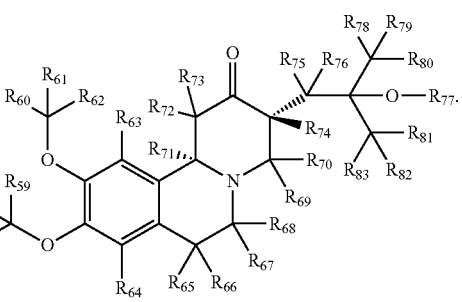

(3R, 11bR)-enantiomer

The term "mixture of diastereomers" refers to either of the $d_6$-tetrabenazine M1 metabolite stereoisomers having the structural formulas shown below:

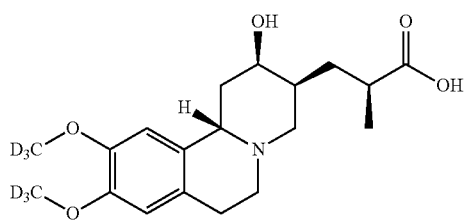
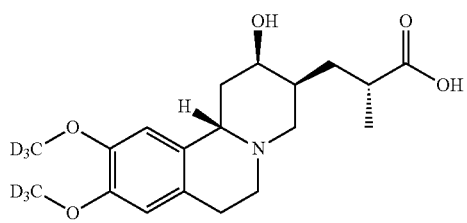
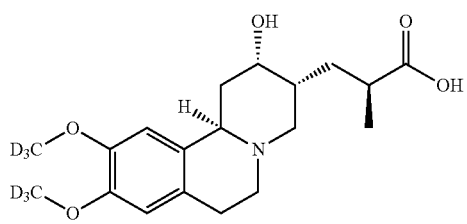
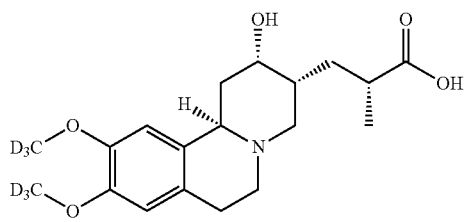

In certain embodiments, a chemical structure may be drawn as one of the diastereomers shown above, but the text of the specification may indicate that each individual diastereomer or a mixture thereof, or all of the foregoing may be intended to be described.

The term "mixture of diastereomers" as applied to a compound of Formula IV refers to a mixture of the stereoisomers of compounds of Formula IV shown below:

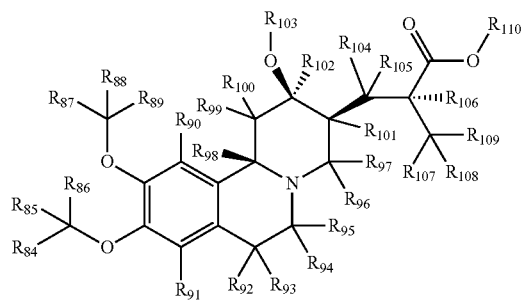
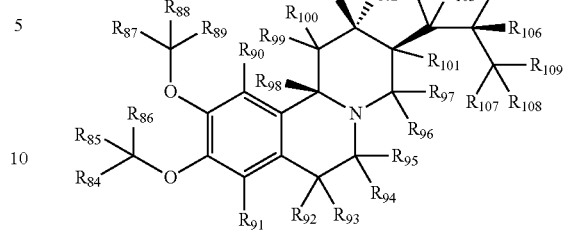
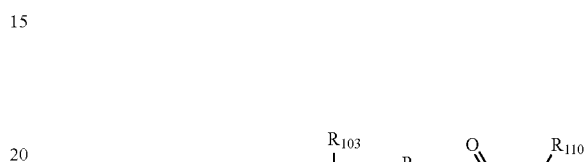
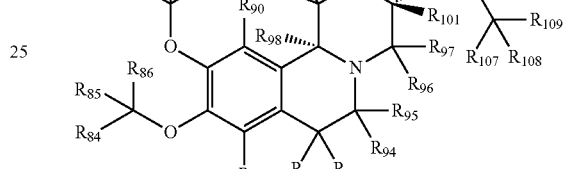

Additional deuterium enriched tetrabenazine analogues include analogs of valbenazine. Valbenazine (NBI-98854, CAS #1025504-59-9, (S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate) is a VMAT2 inhibitor. Valbenazine is currently under investigation for the treatment of movement disorders including tardive dyskinesia. WO 2008058261; WO 2011153157; and U.S. Pat. No. 8,039,627. Valbenazine, a valine ester of (+)-α-dihydrotetrabenazine, in humans is slowly hydrolyzed to (+)-α-dihydrotetrabenazine which is an active metabolite of tetrabenazine which is currently used for the treatment of Huntington's disease. Savani et al., *Neurology* 2007, 68(10), 797; and Kenney et al., *Expert Review of Neurotherapeutics* 2006, 6(1), 7-17.

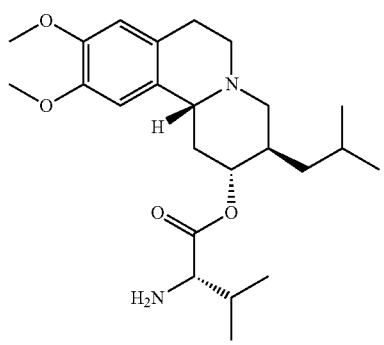

Valbenazine

Dihydrotetrabenazine, formed by hydrolysis of the valine ester of valbenazine, is subject to extensive oxidative metabolism, including O-demethylation of the methoxy groups, as well as hydroxylation of the isobutyl group (Schwartz et al., *Biochem. Pharmacol.*, 1966, 15, 645-655). Adverse effects associated potentially associated with the administration of valbenazine include neuroleptic malignant syndrome, drowsiness, fatigue, nervousness, anxiety, insomnia, agitation, confusion, orthostatic hypotension, nausea, dizziness, depression, and Parkinsonism.

Deuterium-substituted analogues of valbenazine include those as disclosed in WO2014120654. Examples of such compounds are given in the Formulas below.

In certain embodiments of the present invention, compounds have structural Formula I:

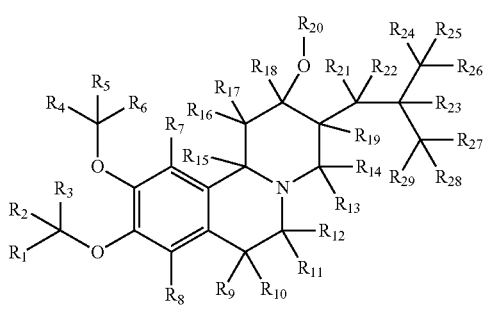

(V)

or a salt thereof, wherein:

$R_1$-$R_{19}$ and $R_{21}$-$R_{29}$ are independently selected from the group consisting of hydrogen and deuterium;

$R_{20}$ is selected from the group consisting of hydrogen, deuterium, —C(O)O-alkyl and —C(O)—$C_{1-6}$alkyl, or a group cleavable under physiological conditions, wherein said alkyl or $C_{1-6}$alkyl is optionally substituted with one or more substituents selected from the group consisting of —NH—C(NH)NH2, —CO$_2$H, —CO$_2$alkyl, —SH, —C(O)NH$_2$, —NH$_2$, phenyl, —OH, 4-hydroxyphenyl, imidazolyl, and indolyl, and any $R_{20}$ substituent is further optionally substituted with deuterium; and at least one of $R_1$-$R_{29}$ is deuterium or contains deuterium.

In certain embodiments, the compounds of Formula V have (+)-alpha stereochemistry.

In certain embodiments, the compounds of Formula V have (−)-alpha stereochemistry.

In further embodiments, the compounds of Formula V have (+)-beta stereochemistry.

In further embodiments, the compounds of Formula V have (−)-beta stereochemistry.

In yet further embodiments, the compounds of Formula I are a mixture of alpha and beta stereoisomers. In yet further embodiments, the ratio of alpha/beta stereoisomers is at least 100:1, at least 50:1, at least 20:1, at least 10:1, at least 5:1, at least 4:1, at least 3:1, or at least 2:1. In yet further embodiments, the ratio of beta/alpha stereoisomers is at least 100:1, at least 50:1, at least 20:1, at least 10:1, at least 5:1, at least 4:1, at least 3:1, or at least 2:1.

In certain embodiments, disclosed herein is a compound of structural Formula VI:

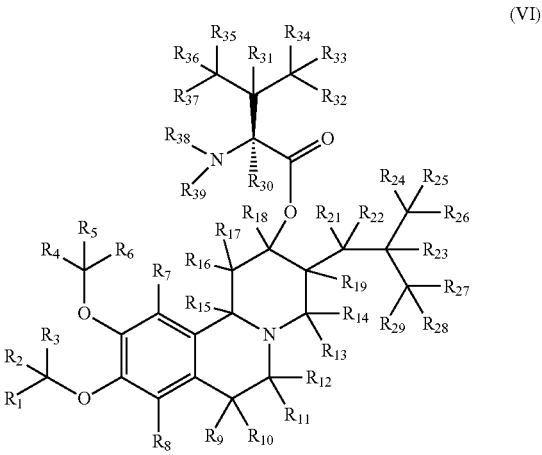

(VI)

or a salt or stereoisomer thereof, wherein:

$R_1$-$R_{19}$ and $R_{21}$-$R_{39}$ are independently selected from the group consisting of hydrogen and deuterium;

at least one of $R_1$-$R_{19}$ and $R_{21}$-$R_{39}$ is deuterium.

In certain embodiments of the present invention, compounds have structural Formula VII:

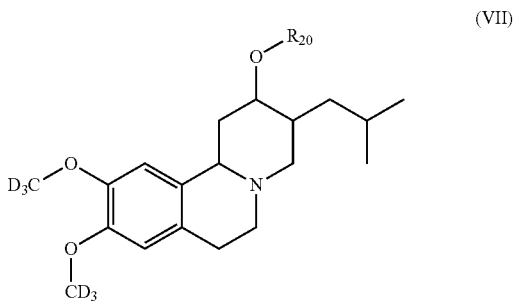

(VII)

or a salt or stereoisomer thereof, wherein:

$R_{20}$ is selected from the group consisting of —C(O)O-alkyl and —C(O)—$C_{1-6}$alkyl, or a group cleavable under physiological conditions, wherein said alkyl or $C_{1-6}$alkyl is optionally substituted with one or more substituents selected from the group consisting of —NH—C(NH)NH2, —CO$_2$H, —CO$_2$alkyl, —SH, —C(O)NH$_2$, —NH$_2$, phenyl, —OH, 4-hydroxyphenyl, imidazolyl, and indolyl, and any $R_{20}$ substituent is further optionally substituted with deuterium.

The compounds as disclosed herein may also contain less prevalent isotopes for other elements, including, but not limited to, $^{13}$C or $^{14}$C for carbon, $^{33}$S, $^{34}$S, or $^{36}$S for sulfur, $^{15}$N for nitrogen, and $^{17}$O or $^{18}$O for oxygen.

Deuterium Kinetic Isotope Effect

Deuterium (D) is a naturally occurring, non-radioactive, stable isotope of hydrogen (H), that contains both a proton and a neutron in its nucleus. The presence of the neutron doubles the mass of D when compared to H, which in turn increases the vibrational frequency of the C-D covalent bond as compared to the C—H covalent bond. An increase in the vibrational frequency of a covalent bond results in an increase in the activation energy required to break that bond, and consequentially an increase in the bond strength. This increased covalent bond strength can in certain instances alter the kinetics of the covalent bond cleavage resulting in what is known as the Kinetic Isotope Effect (KIE). Under certain specific conditions that involve various quantum mechanical aspects of the covalent bond cleavage, the replacement of a covalent C—H bond with a covalent C-D bond can result in a meaningful deuterium KIE. A large deuterium KIE for a drug that is a CYP450 substrate can in certain instances lead to an improvement in the pharmacokinetic parameters of that drug, which can potentially result in a differentiation between the deuterated and the non-deuterated drugs. The covalent C-D bonds in deutetrabenazine satisfy a number of chemical and biological criteria which work in concert to provide a deuterium KIE that is large enough to slow down the O-demethylation of the active metabolites of deutetrabenazine as compared to tetrabenazine. It is important to note that the magnitude of this deuterium KIE could not have been predicted a priori, and hence it was not possible to know ahead of time if the replacement of a C—H covalent bond in tetrabenazine with a C-D covalent bond would have led to a noticeable and/or improved biological difference.

Deutetrabenazine or $d_6$-tetrabenazine is a VMAT2 inhibitor.

In the $d_6$-tetrabenazine, six hydrogen atoms are replaced with deuterium atoms as shown in foregoing figure. There is substantial evidence that $d_6$-tetrabenazine forms stable covalent bonds, and that its trideuteromethyl group (—CD$_3$) is a covalently bound stable moiety with no distinctions or qualifications of that bond as compared to a methyl group (—CH$_3$).

First, the covalent nature of the C-D bond can be established by spectroscopic methods such as Infrared (IR) Spectroscopy. The characteristic IR absorption of C-D stretches at approximately 2000-2300 cm−1 (Miller and Corcelli, 2009) is often used by researchers as site-specific and non-perturbative probes for protein studies (Miller and Corcelli, 2009; Zimmermann et al., 2011). $d_6$-tetrabenazine has distinct IR absorptions at 2060-2250 cm−1 which are attributed to the C-D stretches. These absorption bands are absent from the IR spectrum of the non-deuterated form of tetrabenazine.

Second, $d_6$-tetrabenazine is not a salt form of tetrabenazine. The mass spectrum of deutetrabenazine displays the protonated molecular ion at m/z 324.18 [M+1]. This agrees with the predicted mass number of $d_6$-tetrabenazine as an intact molecule.

Third, deuterium atoms in $d_6$-tetrabenazine do not exchange with hydrogen under normal physiological conditions. The pKa of non-conjugated aliphatic C—H bonds is in the range of 45-50, which means that at equilibrium, the ratio of dissociated to non-dissociated species is less than 10-45. By comparison, the C—H bonds of the methoxy groups of tetrabenazine, and by extension, the C-D bonds of the methoxy groups of $d_6$-tetrabenazine are even less acidic, with a pKa value approaching 50. This means that one would need to increase the pH of an aqueous solution to more than 45 before any of the deuterium atoms in deutetrabenazine can potentially start exchanging with hydrogen atoms.

Finally, $d_6$-tetrabenazine or deutetrabenazine has been administered to humans in clinical studies, and subject to various in vitro incubations with multiple enzymatic processes. The known active metabolites as well as further downstream metabolites have been monitored in vitro incubates and/or in human plasma by LC/MS/MS methods. These metabolites have been synthesized and confirmed to contain the expected trideuteromethyl groups (—CD$_3$), confirming that the covalent C-D bonds in deutetrabenazine are stable and carried into the downstream metabolites of deutetrabenazine. Deutetrabenazine has a differentiated pharmacokinetics profile compared to $d_0$-tetrabenazine.

Due to the deuterium kinetic isotope effect (KIE), replacing H with a D in a covalent C—H bond in a small molecule drug has the potential to attenuate the metabolism of the drug (Baillie, 1981) by requiring more energy for cleavage by enzymes such as cytochrome P450 isozymes (CYP450). The magnitude of the deuterium KIE varies depending on the nature of the C—H bond that is being broken and whether the cleavage of that bond is the rate-limiting step in the oxidative metabolism of the drug by a CYP isozyme.

By attenuating metabolism in this manner, elimination half-life ($t_{1/2}$), exposure (AUC [area under the plasma level-time curve]), and peak plasma concentration (Cmax) may be altered relative to the non-deuterated form of the drug (Kushner et al., 1999; Baillie, 1981). The substitution of D for H at specific positions in a drug has also the potential to attenuate the breakdown of the deuterium containing metabolites of the deuterated parent drug. Many deuterium substitutions of key oxidative metabolic sites do not produce any effects; thus empirical data are required to determine whether deuteration has potentially relevant outcomes in vivo. Tetrabenazine contains numerous C—H covalent bonds that are subject to oxidative metabolism by CYP450 enzymes. For all of the foregoing reasons, a medicine with a longer half-life may result in greater efficacy, better safety and tolerability, improved quality of life and potential for cost savings in the long term. Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, (f) decrease the production of deleterious metabolites in specific tissues, and/or (g) create a more effective drug and/or a safer drug for polypharmacy, whether the polypharmacy be intentional or not. The deuteration approach has demonstrated the ability to slow the metabolism of tetrabenazine and attenuate interpatient variability.

Abbreviations and Definitions

To facilitate understanding of the disclosure, a number of terms and abbreviations as used herein are defined below as follows:

All publications and references cited herein are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

The singular forms "a," "an," and "the" may refer to plural articles unless specifically stated otherwise.

When ranges of values are disclosed, and the notation "from n1 . . . to n2" or "n1-n2" is used, where n1 and n2 are the numbers, then unless otherwise specified, this notation is intended to include the numbers themselves and the range between them. This range may be integral or continuous between and including the end values.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

As used herein, the term "abnormal" refers to an activity or feature that differs from a normal activity or feature.

As used herein, the term "abnormal muscular activity" refers to muscular activity that differs from the muscular activity in a healthy subject. The abnormal activity may be decreased or increased in comparison to normal activity. An increase in muscular activity can result in excessive abnormal movements, excessive normal movements, or a combination of both.

The term "adverse event" ("AE") means any untoward medical occurrence in a patient administered a drug, regardless of whether it has a causal relationship with this treatment. An adverse event can, therefore, be any unfavorable and unintended physical sign, symptom, or laboratory parameter that develops or worsens in severity during the course of this study, or significant worsening of the disease under study or of any concurrent disease, whether or not considered related to the study drug. A new condition or the worsening of a pre-existing condition will be considered an adverse event. Stable chronic conditions (such as arthritis) that are present before study entry and do not worsen during this study will not be considered adverse events. A mild AE is one which does not limit the subject's activities; a moderate AE is one which causes some limitation of usual activities; and a severe AE is one which renders a subject unable to carry out usual activities.

A "treatment-related adverse event" is an adverse event which, in a physician's or clinician's judgment, is related to the drug administered. Such a determination should be understood to often not reduce to a yes/no question, but may lie on a continuum wherein it is more or less likely that the AE is treatment-related, including the closeness of manifestation of the event to dosing, the disappearance of the AE upon discontinuation or reduction in dose of the drug, and the failure of other factors (e.g., preexisting conditions, environmental factors, etc.) to explain the AE.

The term "CYP2D6 inhibitor" refers to a drug which is inhibits CYP2D6, therefore making it unavailable to metabolize other substrate compounds; co-administration of a drug metabolized by CYP2D6 with a CYP2D6 inhibitor should be carried out with caution and often at a reduced dosage, as the plasma concentration of the drug will often be. CYP2D6 inhibitors include amiodarone, celecoxib, chloroquine, chlorpromazine, cimetidine, citalopram, clomipramine, codeine, deiavirdine, desipramine, dextroprpoxyphene, diltiazem, doxorubicin, entacapone (high dose), fluoxetine, fluphenazine, fluvaxamine, haloperidol, labetalol, lobeline, lomustine, methadone, mibefradil, moclobemide, nortuloxeline, paroxetine, perphenazine, propafenone, quinacrine, quinidine, ranitidine, risperidone, ritonavir, serindole, sertraline, thioridazine, valproic acid, venlafaxine, vinblastine, vincristine, vinorelbine, and yohimbine. Strong CYP2D6 inhibitors include fluoxetine, aroxetine, bupropion, quinidine, cinacalcet, and ritonavir.

The term "degree" as used herein in reference to control of abnormal muscular activity or abnormal involuntary movement (e.g., chorea) is meant to be synonymous with "level."

The term "disorder" as used herein is intended to be generally synonymous, and is used interchangeably with, the terms "disease", "syndrome", and "condition" (as in medical condition), in that all reflect an abnormal condition of the human or animal body or of one of its parts that impairs normal functioning, is typically manifested by distinguishing signs and symptoms.

The terms "treat," "treating," and "treatment" are meant to include alleviating or abrogating a disorder or one or more of the symptoms associated with a disorder; or alleviating or eradicating the cause(s) of the disorder itself. As used herein, reference to "treatment" of a disorder is intended to include prevention.

The terms "prevent," "preventing," and "prevention" refer to a method of delaying or precluding the onset of a disorder; and/or its attendant symptoms, barring a subject from acquiring a disorder or reducing a subject's risk of acquiring a disorder.

The terms "tolerable" and "tolerability" refer to that amount of deuterium-substituted tetrabenazine (e.g., deutetrabenazine) or other drug (e.g., deuterium-substituted VMAT inhibitor, or valbenazine) which produces low rates of adverse events such as somnolence, irritability, fatigue, vomiting and nausea in patients and where the adverse events do not lead to dose reduction of the deuterium substituted tetrabenazine or other drug, suspension of the deuterium substituted tetrabenazine or other drug, or withdrawal of the drug deuterium substituted tetrabenazine or other drug. The deuterium substituted tetrabenazine is also considered tolerable if any underlying symptoms such as depression, anxiety, suicidality, parkinsonism in patients having diseases or conditions, such as Huntington's disease, tardive dyskinesia or Tourette syndrome, are not worsened. Tolerable and tolerability shall also refer to that amount of deutetrabenazine (or other drug, if applicable) which does not necessitate a downward adjustment in regular (e.g., daily) dose, or a suspension of dose, for example due to adverse effects. A tolerable amount may vary from between subjects, and also within a subject over the course of a disease or course of treatment.

The term "adequate" as used herein in reference to control of abnormal muscular activity or abnormal involuntary movement (e.g., chorea) in a subject refers a level of control which is observable and satisfactory to the subject. The clinician, investigator, in consultation with the subject, will determine when an adequate level of control of abnormal muscular activity or abnormal involuntary movement (e.g., chorea) has been achieved. Typically, the adequacy of a level of control of abnormal muscular activity or abnormal involuntary movement provided by an amount of a drug will be affected by the tolerability of that amount, and will often be the maximum tolerated amount which yields an observable increase in control (the "optimal" amount). The amount of deutetrabenazine may be increased on a weekly basis until there is adequate control of chorea, the subject experiences a protocol defined "clinically significant" adverse event (defined as related to study medication and either a) moderate or severe in intensity or b) meets the criteria for a Serious Adverse Event (SAE), or the maximal allowable dose is reached. An adequate level may vary from between subjects, and also within a subject over the course of a disease or course of treatment.

The phrases "improve," "improved by," "reduce," "reduced by," and the like, used in reference to a level, degree, or amount by which some quality is reduced, improved, etc. in a subject or subjects by treatment with a compound, is meant to be in comparison to an untreated subject or subjects. Alternatively, if explicitly so stated, these phrases may be in comparison to a subject or subjects treated with a standard of care. Such measures may be made by reference to a relevant scale or assessment known in the art (see, e.g., examples provided herein of disorder-control and/or disorder-eradication endpoint scales, and Likert scales).

The term "abnormal involuntary movement," as used herein, includes involuntary movements associated with or caused by movement disorders.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human patient.

The GTS-QOL consists of two parts. The first part is typically a twenty-seven question assessment of various aspects of how tics affect the subject's life, each to be rated on a five-choice scale of no problem, slight problem, moderate problem, marked problem, or severe problem. Subscales combining some of these aspects can be focused upon, such as, e.g., the physical/activities of daily living (ADL) subscale. The second part is a simple rating of the subject's life satisfaction, where 100 is extremely satisfied and 0 is extremely dissatisfied.

SF-36 Physical Functioning Score. The SF-36 is a short-form health survey with 36 questions used to evaluate health-related quality of life (Ware, 1996). The SF-36 has been useful in comparing specific populations and comparing the relative burden of various diseases. The SF-36 has been evaluated in HD patients and shown to have robust construct validity and test-retest reliability and was also able to discriminate from age-matched controls and normative data on the 10-item physical functioning scale (Ho, 2004). While the entire SF-36 was administered in this study, the physical functioning scale (also known as the PF-10) was analyzed as a key secondary endpoint. The physical functioning scale is a 10-item subset of the SF-36 which examines a subject's perceived health-related limitations with physical activities. The SF-36 physical functioning score is a 10-item scale where subjects rate their ability to perform routine physical activities such as walking, climbing stairs, bathing, or dressing. Given the potential for chorea to interfere with basic motor skills, gait, and walking it is not unexpected that subjects with more impaired function would experience greater benefit on this measure.

The Tourette Syndrome Patient Global Impression of Severity (TS-PGIS) is a novel five-point scale in which 1 indicates no tics, 2 indicates mild tics (not distressing, noticeable, or interfering with daily life), 3 indicates moderate (can be distressing, noticeable, and sometimes interfering with daily life), 4 indicates marked (very distressing, noticeable, and interfering with daily life), and 5 indicates severe (severely distressing, always noticeable, and preventing of most daily activities).

The Tic-Free Interval is a five-point scale in which 1 indicates an interval of at least one day since the last tic, 2 indicates an interval of between 6 hours to less than one day since the last tic, 3 indicates an interval of between one hour and less than 6 hours since the last tic, 4 indicates an interval of between five minutes to less than one hour since the last tic, and 5 indicates less than five minutes since the last tic.

The TS-CGI is a seven-point scale scored by the clinician, in which 1 indicates normal or no tics, 2 indicates tics may or may not be present, 3 indicates mild, observable motor and/or phonic tics that may or may not be noticed, would not call attention to the individual, and are associated with no distress or impairment, 4 indicates moderate, observable motor and/or phonic tics that would always be noticed, would call attention to the individual, and may be associated with some distress or impairment, 5 indicates marked, exaggerated motor and/or phonic tics that are disruptive, would always call attention to the individual, and are always associated with significant distress or impairment, 6 indicates severe, extremely exaggerated motor and/or phonic tics that are disruptive, would always call attention to the individual, and are associated with injury or inability to carry out daily functions, and 7 indicates extreme, incapacitating tics.

The YGTSS is a comprehensive evaluation of various aspects and severity of motor and phonic tics. In one aspect, each of five categories—number, frequency, intensity, complexity, and interference—is scored from 0 to 5 for both motor and phonic tics, producing a tic severity score of 0 to 25 for each of Vocal Tic Severity Score (VTSS) and Motor Tic Severity Score (MTSS). Added together, these comprise the total tic severity (TTS) score. Separately, impairment of the patient's life is scored on a scale of 0 to 50, wherein 0 indicates no impairment, 10 is minimal, 20 is mild, 30 is moderate, 40 is marked, and 50 is severe, yielding an impairment score. When the Impairment score is added to the TTS score, this comprises the complete Global Severity Score (GSS) of the YGTSS.

The Tourette Syndrome Patient Global Impression of Change (TS-PGIC) is a seven-point scale in which −3 indicates very much worse, −2 indicates much worse, −1 indicated minimally worse, 0 indicated no change, 1 indicates minimally improved, 2 indicates much improved, and 3 indicates very much improved.

The GTS-QOL consists of two parts. The first part is typically a twenty-seven question assessment of various aspects of how tics affect the subject's life, each to be rated on a five-choice scale of no problem, slight problem, moderate problem, marked problem, or severe problem. The second part is a simple rating of the subject's life satisfaction, where 100 is extremely satisfied and 0 is extremely dissatisfied.

The Tic-Free Interval is a five-point scale in which 1 indicates an interval of at least one day since the last tic, 2 indicates an interval of between 6 hours to less than one day since the last tic, 3 indicates an interval of between one hour and less than 6 hours since the last tic, 4 indicates an interval of between five minutes to less than one hour since the last tic, and 5 indicates less than five minutes since the last tic.

The term "VMAT2" refers to vesicular monoamine transporter 2, an integral membrane protein that acts to transport monoamines—particularly neurotransmitters such as dopamine, norepinephrine, serotonin, and histamine—from cellular cytosol into synaptic vesicles.

The term "VMAT2-mediated disorder," refers to a disorder that is characterized by abnormal VMAT2 activity. A VMAT2-mediated disorder may be completely or partially mediated by modulating VMAT2. In particular, a VMAT2-mediated disorder is one in which inhibition of VMAT2 results in some effect on the underlying disorder e.g., administration of a VMAT2 inhibitor results in some improvement in at least some of the patients being treated.

The term "VMAT2 inhibitor", "inhibit VMAT2", or "inhibition of VMAT2" refers to the ability of a compound disclosed herein to alter the function of VMAT2. A VMAT2 inhibitor may block or reduce the activity of VMAT2 by forming a reversible or irreversible covalent bond between the inhibitor and VMAT2 or through formation of a noncovalently bound complex. Such inhibition may be manifest only in particular cell types or may be contingent on a particular biological event. The term "VMAT2 inhibitor", "inhibit VMAT2", or "inhibition of VMAT2" also refers to altering the function of VMAT2 by decreasing the probability that a complex forms between a VMAT2 and a natural substrate The compounds disclosed herein can exist as therapeutically acceptable salts. The term "therapeutically acceptable salt," as used herein, represents salts or zwitterionic forms of the compounds disclosed herein which are therapeutically acceptable as defined herein. The salts can be prepared during the final isolation and purification of the compounds or separately by reacting the appropriate compound with a suitable acid or base. Therapeutically acceptable salts include acid and basic addition salts.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecyl sulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methyl amine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

While it may be possible for the compounds of the subject invention to be administered as the raw chemical, it is also possible to present them as a pharmaceutical composition. Accordingly, provided herein are pharmaceutical compositions which comprise one or more of certain compounds disclosed herein, or one or more pharmaceutically acceptable salts, prodrugs, or solvates thereof, together with one or more pharmaceutically acceptable carriers thereof and optionally one or more other therapeutic ingredients. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (.

The compositions include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The compositions may conveniently be presented in unit dosage form and may be prepared by any of the methods well known in the art of pharmacy. Typically, these methods include the step of bringing into association a compound of the subject invention or a pharmaceutically salt, prodrug, or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose.

For administration by inhalation, compounds may be delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

In certain embodiments, the compounds disclosed herein may be formulated or administered using any of formulations and methods disclosed in U.S. patent application Ser. No. 14/030,322, filed Sep. 18, 2013, which is hereby incorporated by reference in its entirety.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the disorder being treated. Also, the route of administration may vary depending on the disorder and its severity.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

Disclosed herein are methods of treating a VMAT2-mediated disorder comprising administering to a subject having or suspected of having such a disorder, a therapeutically effective amount of a compound as disclosed herein or a pharmaceutically acceptable salt, solvate, or prodrug thereof.

VMAT2-mediated disorders, include, but are not limited to, chronic hyperkinetic movement disorders, Huntington's disease, hemiballismus, senile chorea, tic disorders, tardive dyskinesia, dystonia, Tourette syndrome, depression, cancer, rheumatoid arthritis, psychosis, multiple sclerosis, asthma, and/or any disorder which can lessened, alleviated, or prevented by administering a VMAT2 inhibitor.

Also disclosed herein are methods of treating abnormal muscular activity, abnormal involuntary movement, or movement disorders, comprising administering to a subject having or suspected of having such a disorder, a therapeutically effective amount of a compound as disclosed herein or a pharmaceutically acceptable salt, solvate, or prodrug thereof.

Movement disorders include akathisia, akinesia, ataxia, athetosis, ballismus, bradykinesia, cerebral palsy, chorea, corticobasal degeneration, dyskinesias (e.g., paroxysmal), dystonia (general, segmental, focal) including blepharospasm, writer's cramp (limb dystonia), laryngeal dystonia (spasmodic dysphonia), and oromandibular dystonia, essential tremor, geniospasm, hereditary spastic paraplegia, Huntington's Disease, multiple system atrophy (Shy Drager Syndrome), myoclonus, Parkinson's Disease, Parkinson's disease levodopa-induced dyskinesia, parkinsonism, progressive supranuclear palsy, restless legs syndrome, Rett Syndrome, spasmodic torticollis (cervical dystonia), spasticity due to stroke, cerebral palsy, multiple sclerosis, spinal cord or brain injury, stereotypic movement disorder, stereotypy, Sydenham's Chorea, synkinesis, tardive dyskinesia, tics, Tourette syndrome, and Wilson's Disease.

In certain embodiments, a method of treating abnormal muscular activity, abnormal involuntary movement, or movement disorder comprises administering to the subject a therapeutically effective amount of a compound as disclosed herein, or a pharmaceutically acceptable salt, solvate, or prodrug thereof, so as to affect: (1) decreased inter-individual variation in plasma levels of the compound or a metabolite thereof; (2) increased average plasma levels of the compound or decreased average plasma levels of at least one metabolite of the compound per dosage unit; (3) decreased inhibition of, and/or metabolism by at least one cytochrome P450 or monoamine oxidase isoform in the subject; (4) decreased metabolism via at least one polymorphically-expressed cytochrome P450 isoform in the subject; (5) at least one statistically-significantly improved disorder-control and/or disorder-eradication endpoint; (6) an improved clinical effect during the treatment of the disorder, (7) prevention of recurrence, or delay of decline or appearance, of abnormal alimentary or hepatic parameters as the primary clinical benefit, or (8) reduction or elimination of deleterious changes in any diagnostic hepatobiliary function endpoints, as compared to the corresponding non-isotopically enriched compound.

In certain embodiments, inter-individual variation in plasma levels of the compounds as disclosed herein, or metabolites thereof, is decreased; average plasma levels of the compound as disclosed herein are increased; average plasma levels of a metabolite of the compound as disclosed herein are decreased; inhibition of a cytochrome $P_{450}$ or monoamine oxidase isoform by a compound as disclosed herein is decreased; or metabolism of the compound as disclosed herein by at least one polymorphically-expressed cytochrome $P_{450}$ isoform is decreased; by greater than about 5%, greater than about 10%, greater than about 20%, greater than about 30%, greater than about 40%, or by greater than about 50% as compared to the corresponding non-isotopically enriched compound.

Plasma levels of the compound as disclosed herein, or metabolites thereof, may be measured using the methods described by Li et al. *Rapid Communications in Mass Spectrometry* 2005, 19, 1943-1950; Jindal, et al., *Journal of Chromatography, Biomedical Applications* 1989, 493(2), 392-7; Schwartz, et al., *Biochemical Pharmacology* 1966, 15(5), 645-55; Mehvar, et al., *Drug Metabolism and Disposition* 1987, 15(2), 250-5; Roberts et al., *Journal of Chromatography, Biomedical Applications* 1981, 226(1), 175-82; and any references cited therein or any modifications made thereof.

Examples of cytochrome P450 isoforms in a mammalian subject include, but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

Examples of monoamine oxidase isoforms in a mammalian subject include, but are not limited to, $MAO_A$, and $MAO_B$.

The inhibition of the cytochrome P450 isoform is measured by the method of Ko et al. (*British Journal of Clinical Pharmacology*, 2000, 49, 343-351). The inhibition of the $MAO_A$ isoform is measured by the method of Weyler et al. (*J. Biol Chem.* 1985, 260, 13199-13207). The inhibition of the $MAO_B$ isoform is measured by the method of Uebelhack et al. (*Pharmacopsychiatry*, 1998, 31, 187-192).

Examples of polymorphically-expressed cytochrome. Paso isoforms in a mammalian subject include, but are not limited to, CYP2C8, CYP2C9, CYP2C19, and CYP2D6.

The metabolic activities of liver microsomes, cytochrome $P_{450}$ isoforms, and monoamine oxidase isoforms are measured by the methods described herein.

Examples of improved disorder-control and/or disorder-eradication endpoints, or improved clinical effects include, but are not limited to:

b. improved Unified Huntington's Disease Rating Scale (UHDRS) scores;

c. improved Total Maximal Chorea (TMC) Scores of the UHDRS;
d. improved Total Motor Scores (TMS) of the UHDRS;
e. improved Patient Global Impression of Change (PGIC) scores;
f. improved Clinical Global Impression of Change (CGIC) scores;
g. improved Unified Parkinson's Disease Rating Scale scores, including the dysarthria score;
h. improved Abnormal Involuntary Movement Scale (AIMS) scores;
i. improved Goetz Dyskinesia Rating Scale scores;
j. improved Unified Dyskinesia Rating Scale scores;
k. improved PDQ-39 Parkinson's Disease Questionnaire scores;
l. improved Global Primate Dyskinesia Rating Scale scores;
m. improved Berg Balance Test scores;
n. improved Physical Functioning Scale of the SF-36 scores;
o. reduced Hospital Anxiety and Depression Scale (HADS) scores;
p. reduced Columbia Suicide Severity Rating Scale (C-SSRS) scores;
q. improved Swallowing Disturbance Questionnaire (SDQ) scores;
r. improved (reduced) Barnes Akathisia Rating Scale (BARS) scores;
s. reduced Epworth Sleepiness Scale (ESS) scores;
t. improved modified Craniocervical Dystonia 24 (CDQ-24) score;
u. Montreal Cognitive Assessment (MoCA);
v. improved Yale Global Tic Severity Scale (YGTSS) scores, including Motor Tic Severity, Vocal Tic Severity, Total Tic Severity Score (TTS) Impairment, and Global Severity (GSS) scores thereof;
w. improved (reduced) Total Tic Severity Score (TTS);
x. improved Tourette Syndrome Clinical Global Impression (TS-CGI) score;
y. improved Patient Global Impression of Severity in Tourette Syndrome (TS-PGIS) score;
z. Children's Depression inventory 2 (CDI-2; Parent and Self-report versions);
aa. Children's Columbia Suicide Severity Rating Scale (C-SSRS);
bb. Children's Yale-Brown Obsessive-Compulsive Scale (CY-BOCS) score;
cc. Gilles de la Tourette Syndrome—Quality of Life (GTS-QOL), including the physical/activities of daily living subscale score, the overall life satisfaction score as measured by the visual analog scale (VAS), the psychological subscale score, obsessive-compulsive subscale score, and/or the cognitive subscale score thereof;

Examples of diagnostic hepatobiliary function endpoints include, but are not limited to, alanine aminotransferase ("ALT"), serum glutamic-pyruvic transaminase ("SGPT"), aspartate aminotransferase ("AST" or "SGOT"), ALT/AST ratios, serum aldolase, alkaline phosphatase ("ALP"), ammonia levels, bilirubin, gamma-glutamyl transpeptidase ("GGTP," "γ-GTP," or "GGT"), leucine aminopeptidase ("LAP"), liver biopsy, liver ultrasonography, liver nuclear scan, 5'-nucleotidase, and blood protein. Hepatobiliary endpoints are compared to the stated normal levels as given in "Diagnostic and Laboratory Test Reference", 4$^{th}$ edition, Mosby, 1999. These assays are run by accredited laboratories according to standard protocol.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Combination Therapy

The compounds disclosed herein may also be combined or used in combination with other agents useful in the treatment of VMAT2-mediated disorders. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In certain embodiments, the compounds disclosed herein can be combined with one or more dopamine precursors, including, but not limited to, levodopa.

In certain embodiments, the compounds disclosed herein can be combined with one or more DOPA decarboxylase inhibitors, including, but not limited to, carbidopa.

In certain embodiments, the compounds disclosed herein can be combined with one or more catechol-O-methyl transferase (COMT) inhibitors, including, but not limited to, entacapone and tolcapone.

In certain embodiments, the compounds disclosed herein can be combined with one or more dopamine receptor agonists, including, but not limited to, apomorphine, bromocriptine, ropinirole, and pramipexole.

In certain embodiments, the compounds disclosed herein can be combined with one or more neuroprotective agents, including, but not limited to, selegeline and riluzole.

In certain embodiments, the compounds disclosed herein can be combined with one or more NMDA antagonists, including, but not limited to, amantidine.

In certain embodiments, the compounds disclosed herein can be combined with one or more anti-psychotics, including, but not limited to, chlorpromazine, levomepromazine, promazine, acepromazine, triflupromazine, cyamemazine, chlorproethazine, dixyrazine, fluphenazine, perphenazine, prochlorperazine, thiopropazate, trifluoperazine, acetophenazine, thioproperazine, butaperazine, perazine, periciazine, thioridazine, mesoridazine, pipotiazine, haloperidol, trifluperidol, melperone, moperone, pipamperone, bromperidol, benperidol, droperidol, fluanisone, oxypertine, molindone, sertindole, ziprasidone, flupentixol, clopenthixol, chlorprothixene, thiothixene, zuclopenthixol, fluspirilene, pimozide, penfluridol, loxapine, clozapine, olanzapine, quetiapine, tetrabenazine, sulpiride, sultopride, tiapride, remoxipride, amisulpride, veralipride, levosulpiride, lithium, prothipendyl, risperidone, clotiapine, mosapramine, zotepine, pripiprazole, and paliperidone.

In certain embodiments, the compounds disclosed herein can be combined with one or more benzodiazepines ("minor tranquilizers"), including, but not limited to alprazolam, adinazolam, bromazepam, camazepam, clobazam, clonazepam, clotiazepam, cloxazolam, diazepam, ethyl loflazepate, estizolam, fludiazepam, flunitrazepam, halazepam, ketazolam, lorazepam, medazepam, dazolam, nitrazepam, nordazepam, oxazepam, potassium clorazepate, pinazepam, prazepam, tofisopam, triazolam, temazepam, and chlordiazepoxide.

In certain embodiments, the compounds disclosed herein can be combined with olanzapine or pimozide.

The compounds disclosed herein can also be administered in combination with other classes of compounds, including, but not limited to, anti-retroviral agents; CYP3A inhibitors; CYP3A inducers; protease inhibitors; adrenergic agonists; anti-cholinergics; mast cell stabilizers; xanthines; leukotriene antagonists; glucocorticoids treatments; local or general anesthetics; non-steroidal anti-inflammatory agents (NSAIDs), such as naproxen; antibacterial agents, such as amoxicillin; cholesteryl ester transfer protein (CETP) inhibitors, such as anacetrapib; anti-fungal agents, such as isoconazole; sepsis treatments, such as drotrecogin-α; steroidals, such as hydrocortisone; local or general anesthetics, such as ketamine; norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor Vila Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-muscarinic agents; beta-muscarinic agents, such as carvedilol and metoprolol; antiarrhythmic agents; diuretics, such as chlorothlazide, hydrochlorothiazide, flumethiazide, hydroflumethiazide, bendroflumethiazide, methylchlorothiazi de, trichioromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors; (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, and octreotide acetate; microtubule-disruptor agents, such as ecteinascidins; microtubule-stablizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Thus, in another aspect, certain embodiments provide methods for treating VMAT2-mediated disorders in a subject in need of such treatment comprising administering to said subject an amount of a compound disclosed herein effective to reduce or prevent said disorder in the subject, in combination with at least one additional agent for the treatment of said disorder. In a related aspect, certain embodiments provide therapeutic compositions comprising at least one compound disclosed herein in combination with one or more additional agents for the treatment of VMAT2-mediated disorders.

General Synthetic Methods for Preparing Compounds

The compounds as disclosed herein can be prepared by methods known to one of skill in the art and routine modifications thereof, and/or following procedures similar to those described in US 20100130480 (paragraphs [0093]-[0121]), US 20120003330 (paragraphs [0104]-[0162]), WO 2005077946; WO 2008/058261; EP 1716145; Lee et al., *J. Med. Chem.*, 1996, (39), 191-196; Kilbourn et al., *Chirality*, 1997, (9), 59-62; Boldt et al., *Synth. Commun.*, 2009, (39), 3574-3585; Rishel et al., *J. Org. Chem.*, 2009, (74), 4001-4004; DaSilva et al., *Appl. Radiat. Isot.*, 1993, 44(4), 673-676; Popp et al., *J. Pharm. Sci.*, 1978, 67(6), 871-873; Ivanov et al., *Heterocycles* 2001, 55(8), 1569-1572; U.S. Pat. Nos. 2,830,993; 3,045,021; WO 2007130365; WO 2008058261, which are hereby incorporated in their entirety, and references cited therein and routine modifications thereof.

Isotopic hydrogen can be introduced into a compound as disclosed herein by synthetic techniques that employ deuterated reagents, whereby incorporation rates are pre-determined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. Exchange techniques, on the other hand, may yield lower tritium or deuterium incorporation, often with the isotope being distributed over many sites on the molecule.

In certain embodiments, specific examples of compounds of the present invention include a compound selected from the list described in paragraph [0122] of US 20100130480 and paragraph [0163] of US 20120003330, which are hereby incorporated by reference.

Changes in the in vitro metabolic properties of certain of the compounds disclosed herein as compared to their non-isotopically enriched analogs and methods of determining such changes have been described in paragraph [0125] of US 20100130480 and paragraphs [0165]-[0185] of US 20120003330, which are hereby incorporated by reference.

Formulations

Compounds may be formulated for use in the dosage regimens and methods disclosed herein by methods known in the art, e.g., as disclosed in US2014/0336386. Examples of these formulations are provided below.

15 mg $d_6$-Tetrabenazine Gastro-Erosional Extended Release (Small Tablet) (Formulation A). Table 1 below discloses the elements of a 350 mg total weight gastro-erosional granulation formulation tablet comprising 15 mg (RR, SS)-1,3,4,6,7,11b-hexahydro-9,10-di(methoxy-$d_3$)-3-(2-methylpropyl)-2H-benzo[a]quinolizin-2-one.

TABLE 1

| Material | mg/tab | % |
| --- | --- | --- |
| $d_6$-Tetrabenazine (milled) | 15.0 | 4.3 |
| Mannitol Powder | 185.4 | 53.0 |
| Microcrystalline Cellulose | 61.8 | 17.7 |
| PVP K29/32 | 14.0 | 4.0 |
| Tween 80 (Polysorbate 80) | 3.8 | 1.1 |
| Mannogem ® EZ (spray dried mannitol) | 31.5 | 9.0 |
| POLYOX ® N60K | 35.0 | 10.0 |
| Magnesium Stearate | 3.5 | 1.0 |
| Totals: | 350.0 | 100.0 |

$d_6$-Tetrabenazine (milled) is combined along with Mannitol Powder, Microcrystalline Cellulose, PVP K29/32 and Tween 80 (Polysorbate 80) into a high shear granulator and initially dry mixed at high impeller and chopper speed for 5 minutes. While mixing at high impeller speed and low chopper speed, Purified Water is added to the mixing powders to granulate the material. Additional mixing and water addition with high impeller and high chopper speed continues until the desired granulation end-point is achieved. The resulting granulation is wet screened to break up any oversized agglomerates and the material is added to a fluid bed drier and dried at 60° C. until the desired L.O.D. (loss on drying) is achieved. The dried material is sieved through a #20 mesh screen and the oversized material is milled to a particle size of just under 20 mesh in size. The dried and sized material is combined with Spray Dried Mannitol and POLYOX® N60K into a diffusive mixer (V-Blender) where it is blended for 15 minutes. Magnesium Stearate is then passed through a #30 mesh screen and added to the blended material in the V-Blender. The contents are then lubricated for 3 minutes and discharged for tablet compression. Using a rotary tablet press fitted with punches and dies of the desired shape and size, the lubricated blend is compressed into tablets of a theoretical weight of 350 mg.

7.5 mg $d_6$-Tetrabenazine Gastro-Erosional Extended Release (Small Tablet) (Formulation A). Table 2 below discloses the elements of a 350 mg total weight gastro-erosional granulation formulation tablet comprising 7.5 mg $d_6$-tetrabenazine. Same process as described for Example 1.

TABLE 2

| Material | mg/tab | % |
| --- | --- | --- |
| $d_6$-Tetrabenazine (milled) | 7.5 | 2.1 |
| Mannitol Powder | 191.0 | 54.6 |
| Microcrystalline Cellulose | 63.7 | 18.2 |
| PVP K29/32 | 14.0 | 4.0 |
| Tween 80 (Polysorbate 80) | 3.8 | 1.1 |
| Mannogem EZ (spray dried mannitol) | 31.5 | 9.0 |
| POLYOX ® N60K | 35.0 | 10.0 |
| Magnesium Stearate | 3.5 | 1.0 |
| Totals: | 350.0 | 100.0 |

15 mg $d_6$-Tetrabenazine Gastro-Retentive Extended Release (Large Tablet) (Formulation B). Table 3 below discloses the elements of a 700 mg total weight gastro-retentive formulation tablet comprising 15 mg $d_6$-tetrabenazine. The gastro-retentive tablet is an elongated capsule having dimensions of approximately 0.7087 in. long by 0.3071 in. wide, having rounded ends with a cup depth of 0.0540 in. on each opposing side.

TABLE 3

| Material | mg/tab | % |
| --- | --- | --- |
| $d_6$-Tetrabenazine (milled) | 15.0 | 2.1 |
| Mannitol Powder | 357.5 | 51.1 |
| Microcrystalline Cellulose | 119.0 | 17.0 |
| PVP K29/32 | 26.0 | 3.7 |
| Tween 80 (Polysorbate 80) | 7.5 | 1.1 |
| Mannogem EZ (spray dried mannitol) | 45.5 | 6.5 |
| POLYOX ® N60K | 122.5 | 17.5 |
| Magnesium Stearate | 7.0 | 1.0 |
| Totals: | 700.0 | 100.0 |

7.5 mg $d_6$-Tetrabenazine Gastro-Retentive Extended Release (Large Tablet) (Formulation B). Table 4 below discloses the elements of a 700 mg total weight gastro-retentive formulation tablet comprising 7.5 mg $d_6$-tetrabenazine. The gastro-retentive tablet is an elongated capsule having dimensions of approximately 0.7087 in. long by 0.3071 in. wide, having rounded ends with a cup depth of 0.0540 in. on each opposing side. Same process as described for Example 1. But theoretical compression weight is 700 mg.

TABLE 4

| Material | mg/tab | % |
| --- | --- | --- |
| $d_6$-Tetrabenazine (milled) | 7.5 | 1.1 |
| Mannitol Powder | 363.0 | 51.9 |
| Microcrystalline Cellulose | 121.0 | 17.3 |
| PVP K29/32 | 26.0 | 3.7 |
| Tween 80 (Polysorbate 80) | 7.5 | 1.1 |
| Mannogem ® EZ (spray dried mannitol) | 45.5 | 6.5 |
| POLYOX ® N60K | 122.5 | 17.5 |
| Magnesium Stearate | 7.0 | 1.0 |
| Totals: | 700.0 | 100.0 |

6 mg $d_6$-Tetrabenazine Immediate Release Tablet. Table 5 below discloses the elements of a 125 mg total weight immediate-release tablet comprising 6 mg $d_6$-tetrabenazine.

TABLE 5

| Material | mg/tab | % |
| --- | --- | --- |
| $d_6$-Tetrabenazine (milled) | 6.0 | 4.8 |
| Mannitol Powder | 75.0 | 60.0 |
| Microcrystalline Cellulose | 25.0 | 20.0 |
| Sodium Starch Glycolate | 2.5 | 2.0 |
| PVP K29/32 | 6.0 | 4.8 |
| Tween 80 (Polysorbate 80) | 1.0 | 0.8 |
| Mannogem ® EZ (spray dried mannitol) | 5.8 | 4.6 |
| Sodium Starch Glycolate | 2.5 | 2.0 |
| Magnesium Stearate | 1.2 | 1.0 |
| Totals: | 125.0 | 100.0 |

$d_6$-Tetrabenazine (milled) is combined along with Mannitol Powder, Microcrystalline Cellulose, Sodium Starch Glycolate, PVP K29/32 and Tween 80 (Polysorbate 80) into a high shear granulator and initially dry mixed at high impeller and chopper speed for 5 minutes. While mixing at high impeller speed and low chopper speed, Purified Water is added to the mixing powders to granulate the material. Additional mixing and water addition with high impeller and high chopper speed continues until the desired granulation end-point is achieved. The resulting granulation is wet screened to break up any oversized agglomerates and the material is added to a fluid bed drier and dried at 60° C. until the desired L.O.D. (loss on drying) is achieved. The dried material is sieved through a #20 mesh screen and the oversized material is milled to a particle size of just under 20 mesh in size. The dried and sized material is combined with Spray Dried Mannitol and Sodium Starch Glycolate.

In all of the the methods and compositions disclosed herein using deutetrabenazine, the deutetrabenazine may be administered or formulated as part of a pharmaceutical composition as disclosed in tables 1-5 above.

Clinical Trials and Results

First-HD

First-HD was a randomized, double-blind, placebo-controlled, parallel-group study designed to evaluate the efficacy, safety, and tolerability of deutetrabenazine in subjects with chorea associated with HD. This trial was conducted in the United States and Canada, in collaboration with the Huntington Study Group.

Study Design

Subjects in First-HD were treated with deutetrabenazine or placebo, starting at 6 mg once per day and titrating weekly to doses of up to 24 mg twice per day (48 mg total maximum daily dose). A total of 90 subjects (45 in each group) were enrolled for evaluation over 13 weeks. Subjects were individually titrated to an optimal dose over up to eight weeks, received maintenance therapy at the optimal dose for four weeks, and were taken off study medication in the final week of the trial.

Subject Disposition and Demographic and Baseline Characteristics

Of the 90 subjects randomized, 87 subjects completed the study. The study population was typical for subjects with chorea associated with HD. At baseline, the mean age of the subjects was 53.7 years. The majority of subjects were white (92.2%) and male (55.6%). The mean CAG repeat length among the subject population was 43.9. At baseline, the mean TMC score was 12.7 in the overall population (range 8.0-19.5).

Study Endpoints and Measurements

The primary efficacy endpoint for the study was the change from baseline to maintenance therapy (average of Week 9 and Week 12 values) in the maximal chorea score of the UHDRS. The total maximal score, or TMC, is a clinician-based, quantitative assessment of chorea in seven body regions: face, mouth/tongue, trunk, and the four extremities, with higher scores representing more severe chorea. This is the same endpoint that was accepted by the FDA when it considered and approved tetrabenazine in 2008 (NDA 21894).

The total motor score (TMS) of the UT-MRS was pre-specified as an additional efficacy endpoint in First-HD. The TMS assesses all the motor features of HD, including items addressing characteristic motor abnormalities other than chorea, such as dystonia, gait, parkinsonism, and postural instability.

The clinical relevance of the change in the TMC score was assessed with four prespecified secondary endpoints that assessed changes from baseline to end of treatment (Week 12). These secondary endpoints were tested in a hierarchical manner:

1. Treatment success based on patient global impression of change (PGIC);
2. Treatment success based on clinical global impression of change (CGIC);
3. Physical Functioning Scale of the SF-36; and
4. Balance, as assessed by the Berg Balance Test (BBT).

The PGIC and CGIC are single-item questionnaires that ask the subject and investigator, respectively, to assess a subject's overall HD symptoms at specific visits after initiating therapy. Both assessments use a 7-point Likert Scale, with responses ranging from Very Much Worse (−3) to Very Much Improved (+3) to assess overall response to therapy. Patients and clinicians were asked, "With respect to your (or the subject's) overall Huntington's disease symptoms, how would you describe yourself (or the subject) compared to immediately before starting study medication." Treatment success according to these scales was defined as a rating of Much Improved or Very Much Improved at Week 12. Subjects who did not have a response at Week 12 were assumed to be treatment failures.

Adverse events (AE) and their potential association with treatment were also monitored. Categories of AEs of particular focus included those known to be associated with tetrabenazine use:

Psychiatric disorders: insomnia, depression/agitated depression, abnormal dreams, agitation, anxiety, suicidal ideation, compulsions, impulsive behavior, and sleep disorders;

Nervous system disorders: somnolence, dizziness, akathisia/restlessness, cognitive disorders, drooling, dyskinesia, migraine, headache, loss of consciousness, and syncope (fainting);

General disorders: irritability, fatigue, gait disturbance, chest pain, and hangover; and Gastrointestinal disorders: diarrhea, dry mouth, constipation, nausea, upper abdominal pain, dyspepsia, frequent bowel movements, gastrointestinal pain, vomiting, dysphagia, flatulence, and salivary hypersecretion.

In addition to AE reporting, rating scales were used to monitor for potential subclinical toxicity due to excessive monoamine depletion. Such safety scales were employed in the tetrabenazine development program. These scales applied in First-HD included the Hospital Anxiety and Depression Scale (HADS), the Columbia Suicide Severity Rating Scale (C-SSRS), the Swallowing Disturbance Questionnaire (SDQ), the Unified Parkinson's Disease Rating Scale (dysarthria item) (UPDRS [dysarthria]), the Barnes Akathisia Rating Scale (BARS), and the Epworth Sleepiness Scale (ESS). In addition, the UHDRS, which includes cognitive, behavioral, and functional measures, was performed at key visits.

The Swallowing Disturbance Questionnaire (SDQ) was used prospectively to assess swallowing impairment during the study, as dysphagia is a common problem in patients with HD. This 15-item assessment has been validated in patients with Parkinson's disease and has been shown to be a sensitive and accurate tool for identifying patients with swallowing disturbances arising from different etiologies. The SDQ is recommended by the National Institute of Neurological Disorders and Stroke Common data elements for assessing swallowing impairment in Parkinson's disease, and thus is also relevant for patients with HD, given they may have bradykinesia and other parkinsonian symptoms as part of their illness.

Minor fluctuations in vital signs (blood pressure, heart rate, respiratory rate, and temperature) were observed during the study.

Results

The mean dose at the end of treatment period was 39.7 mg (SD 9.3 mg, range 12-48 mg) in the deutetrabenazine group and 43.3 mg (7.6 mg, range 12-48 mg) in the placebo group. Mean dosage for the 10 deutetrabenazine group subjects with impaired CYP2D6 function (poor metabolizers or on strong CYP2D6 inhibiting medications) was 34.8 mg (3.8 mg, range 30-42 mg). The overall compliance rates were 94.1% and 95.1% for placebo and deutetrabenazine groups, respectively.

Treatment with deutetrabenazine resulted in improvements in all endpoints and reduced incidence of adverse events. In the results below, DTBZ=deutetrabenazine, CI=confidence interval (based on the t-distribution); SD=standard deviation; Least squares means and p-value were obtained from a two-sided test of the effect of treatment from and analysis of covariance model with a term for treatment and the baseline score as covariate.

Total Maximal Chorea Score (TMC). Treatment with deutetrabenazine resulted in robust improvement in maximal chorea score. TMC score at a given time point is determined from Item 12 of the UHDRS. Change in TMC is the difference between baseline and maintenance therapy values. The baseline value is the mean of the Screening and Day 0 values and the maintenance therapy value is the mean of the Week 9 and Week 12 values. For the primary endpoint, subjects receiving deutetrabenazine achieved a significant reduction of 2.5 units on the TMC score from baseline to maintenance therapy compared with placebo (p<0.0001). This reduction in maximal chorea represented a reduction of 21 percentage points compared with placebo (p<0.0001). Deutetrabenazine (DTBZ) was administered at approximately half the daily dose of tetrabenazine. The efficacy of deutetrabenazine was therefore achieved at about half the daily dose of tetrabenazine.

TABLE 6

Total Maximal Chorea Score - Change from Baseline to Maintenance Therapy

| Statistic | Change in Total Maximal Chorea Score | | Difference in Means (DTBZ − Placebo) and 95% CI) |
|---|---|---|---|
| | DTBZ (N = 45) | Placebo (N = 45) | |
| Absolute Change in Total Maximal Chorea Score (Primary Efficacy Endpoint) | | | |
| Least Squares Mean (SD) | −4.4 (3.0) | −1.9 (2.7) | −2.5 (−3.7, −1.3) |
| p-value | — | — | <0.0001 |
| Percentage Change in Total Maximal Chorea Score (Additional Efficacy Endpoint) (%) | | | |
| Least Squares Mean (SD) | −37 (25.7) | −16 (19.6) | −21 (−30.5, −11.1) |
| p-value | — | — | <0.0001 |

Total Motor Score (TMS). Additionally, a statistically significant improvement in the TMS of 4.0 units, compared with placebo, was observed. The fact that the TMS improvement was greater in magnitude than the TMC score improvement (−2.5 units), suggests a benefit of deutetrabenazine treatment on other motor symptoms of HD, in addition to the reduction in chorea. The majority of this improvement was due to chorea, but the total maximal dystonia score also contributed, with deutetrabenazine improving by 0.9 (SE 0.24) points versus placebo 0.1 (SE 0.32) points (p=0.02). From baseline to maintenance therapy, TMC improved by 37% in the deutetrabenazine groups vs. 16% improvement in the placebo group (p<0.0001). Changes in other UHDRS motor components did not differ significantly between treatment groups, including no significant difference in the changes in the parkinsonism subscore (finger taps; pronation/supination; rigidity; bradykinesia; gait; tandem walking; and retropulsion pull test scores) between deutetrabenazine and placebo groups.

TABLE 7

Total Motor Score - Change from Baseline to Maintenance Therapy

| Statistic | DTBZ (N = 45) | Placebo (N = 45) | Difference in Means (DTBZ − Placebo) and 95% CI |
|---|---|---|---|
| Least Squares Mean (SD) | −7.4 (6.3) | −3.4 (5.5) | −4.0 (−6.5, −1.5) |
| p-value | — | — | 0.0023 |

Total Motor Score: comparison to tetrabenazine. In contrast, in a 12-week placebo-controlled study, tetrabenazine was demonstrated to improve the TMC score of the UHDRS but the tetrabenazine treatment failed to show statistically significant improvement in TMS (Huntington Study Group, 2006). These results suggest that tetrabenazine controls chorea associated with HD, but patients may experience a possible decline in motor function that offsets the observed benefit on chorea.

Conclusion. Therefore, deutetrabenazine may represent a superior choice for treatment of movement disorders generally. It is noteworthy that deutetrabenazine achieved efficacy at about half the daily dose of tetrabenazine.

Patient Global Impression of Change (PGIC) and Clinical Global Impression of Change (CGIC). At end of therapy, 51% (23 of 45) of deutetrabenazine-treated subjects were much improved or very much improved based on the PGIC, compared with 20% (9 of 45) subjects in the placebo group (p=0.0020). Similar findings were observed by the treating physicians, where 42% (19 of 45) deutetrabenazine-treated subjects were assessed as having achieved treatment success based on the CGIC compared with 13% (6 of 45) subjects in the placebo group (p=0.0022). These results indicate that deutetrabenazine-treated subjects experienced a clinically meaningful benefit on their overall symptoms of HD and their treating clinicians were also able to observe the benefit.

Improvement in these physician and patient assessment scores indicate that the improvement measured by the TMC and TMS translated into improvement of HD symptoms and further supports the clinical benefit of deutetrabenazine.

TABLE 8

Treatment Success at End of Therapy Determined by PGIC and CGIC

| | DTBZ (N = 45) (%) | Placebo (N = 45) (%) | Difference in Percentages for Treatment Success (DTBZ − Placebo) and 95% CI (%) |
|---|---|---|---|
| Patient Global Impression of Change: Treatment Success at the End of Therapy[b] | | | |
| p-value[c] | 51 — | 20 — | 31 (12.4, 49.8) 0.0020 |
| Clinical Global Impression of Change: Treatment Success at the End of Therapy[b] | | | |
| p-value[c] | 42 — | 13 — | 29 (11.4, 46.4) 0.0022 |

SF-36 Physical Functioning Score. The Physical Functioning Score of the SF-36 was selected as a key secondary endpoint because it is a patient-reported instrument that has been used in many disease states and it assesses physical activities relevant to patients living with HD. The 10-item physical functioning score queries patients regarding self-care such as bathing, dressing, lifting or carrying groceries, climbing one or more flights of stairs, bending, kneeling, walking 100 yards or more, and moderate to vigorous activities. The SF-36 physical functioning score has been shown to measure impairment experienced by people living with HD.

The mean change from baseline to Week 12 in the SF-36 physical functioning score is provided below, where deutetrabenazine treated subjects demonstrated a mean improvement of 0.74 in treated patients over baseline, compared to a worsening of 3.61 units in the placebo group (a difference of 4.3 units). In subjects with more severe chorea at baseline (TMC >the median of the population, or TMC >12; n=49), the benefit of deutetrabenazine on physical functioning was more pronounced, with a mean improvement of 7.1 units over placebo (p=0.0075).

Change from Baseline to Week 12 on the SF-36 physical functioning score showed that SD-809-treated subjects had greater improvement in physical function compared with placebo-treated subjects (p=0.03). Analysis of SF-36 by baseline severity of chorea indicated that SD-809 had a greater benefit in subjects with more severe chorea (p=0.0075). Given the potential for chorea to interfere with basic motor skills, gait, and walking it is not unexpected that subjects with more impaired function would experience greater benefit on this measure.

Given the significant negative impact that chorea has on the patient's quality of life and physical functioning, the statistically significant improvement in the subjects' assessment of their ability to perform activities of daily living further supports the clinical benefit of deutetrabenazine.

TABLE 9

SF-36 Physical Functioning Score - Change from Baseline to Week 12

| | Change in SF-36 Score from Baseline to Week 12 | | |
|---|---|---|---|
| Statistic | DTBZ (N = 45) | Placebo (N = 45) | Difference in Means (DTBZ − Placebo) and 95% CI |
| N | 45 | 43 | |
| Least Squares Mean (SD) | 0.74 (9.773) | −3.61 (9.669) | 4.34 (0.41, 8.27) |
| p-value | — | — | 0.0308 |

Berg Balance Test. The BBT is a 14-item assessment of balance that was used to evaluate if reducing chorea had an impact on balance, since many medications currently used to treat chorea may worsen balance. The BBT was assessed as a safety measure and efficacy endpoint. As summarized below, deutetrabenazine did not worsen balance at end of treatment, and in fact the data numerically favored deutetrabenazine, although the improvement was not statistically significant (p=0.1415). In addition, there was no statistically significant difference between deutetrabenazine and placebo on the BBT observed during the course of the study.

TABLE 10

Change in Berg Balance Test Score from Baseline to Week 12

| | Change in BBT Score from Baseline to Week 12 | | |
|---|---|---|---|
| Statistic | DTBZ (N = 45) | Placebo (N = 45) | Difference in Means (DTBZ − Placebo) and 95% CI |
| Least Squares Mean (SD) | 2.2 (3.47) | 1.3 (4.04) | 1.0 (−0.3, 2.3) |
| p-value | — | — | 0.1415 |

Adverse Events. Deutetrabenazine was generally well tolerated. The overall rates of adverse events (AEs) were the same between the deutetrabenazine and placebo groups, with (60.0%) of subjects in each group experiencing at least one AE. There were no deaths in the study. There was one subject with two serious AEs (cholecystitis and agitated depression) in the deutetrabenazine group, and one subject with one serious AE (exacerbation of chronic obstructive pulmonary disease, or COPD) in the placebo group. The same subject experiencing the serious AEs in the deutetrabenazine group also reported suicidal ideation, which was not considered a serious AE, and subsequently withdrew from the study due to an AE of agitation. In the placebo group, one subject reported suicidal ideation on the Columbia Suicide Severity Rating Scale and one subject withdrew from the study due to an AE of atrial fibrillation. Evidence of good tolerability is further indicated by the same rates of AEs leading to dose reduction, dose suspension and withdrawal. Finally, CYP2D6 genetic status did not impact dosing in this study or the rate of AE. As expected, poor metabolizers, either through genetics or concomitant medications, were dosed slightly lower and without additional AEs, supporting the notion that deutetrabenazine dosing may be managed clinically without reliance on expensive genotyping.

TABLE 11

Overview of Treatment-Emergent Adverse Events

| Type of Event | DTBZ (N = 45) n (%) | Placebo (N = 45) n (%) |
|---|---|---|
| Any Treatment-Emergent AEs (TEAEs) | 27 (60.0) | 27 (60.0) |
| Any Psychiatric Disorders TEAE | 8 (17.8) | 8 (17.8) |
| Any Nervous System Disorders TEAE | 8 (17.8) | 10 (22.2) |
| Any Serious TEAEs | 1 (2.2) | 1 (2.2) |
| Any TEAEs Resulting in Dose Reduction | 3 (6.7) | 3 (6.7) |
| Any TEAEs Resulting in Dose Suspension | 1 (2.2) | 1 (2.2) |
| Any TEAE that led to Withdrawal from the Study | 1 (2.2) | 1 (2.2) |

Similar rates of AEs were also observed among the psychiatric and nervous system body systems, which are areas of particular importance for patients with HD. The numbers of subjects reporting AEs in certain system organ classes of psychiatric, nervous system, gastrointestinal and other general disorders are listed in Table 12 below. These body systems are highlighted because they include many of the underlying symptoms observed in patients with HD and were also frequent AEs observed with tetrabenazine. Deutetrabenazine-treated subjects had low rates of insomnia, depression, anxiety, agitation, suicidal ideation, akathisia, irritability, and fatigue and these rates were similar to or lower than the incidence observed in placebo-treated subjects. Importantly, no AEs of parkinsonism or dysphagia were reported in the deutetrabenazine group. The most common AE observed in the deutetrabenazine group was somnolence, which was observed in 11.1% of subjects versus 4.4% in the placebo group, or a drug-placebo difference of 6.7%.

TABLE 12

Treatment-Emergent Adverse Events

| System Organ Class | Preferred Term | DTBZ (N = 45) n (%) | Placebo (N = 45) n (%) |
|---|---|---|---|
| PSYCHIATRIC DISORDERS | Insomnia | 3 (6.7) | 2 (4.4) |
| | Depression/Agitated Depression | 2 (4.4) | 3 (6.7) |
| | Abnormal Dreams | 1 (2.2) | 1 (2.2) |
| | Agitation | 1 (2.2) | 0 |
| | Anxiety | 1 (2.2) | 1 (2.2) |
| | Suicidal Ideation | 1 (2.2) | 0 |
| | Compulsions | 0 | 1 (2.2) |
| | Impulsive Behavior | 0 | 1 (2.2) |
| | Sleep Disorder | 0 | 3 (6.7) |
| NERVOUS SYSTEM DISORDERS | Somnolence | 5 (11.1) | 2 (4.4) |
| | Dizziness | 2 (4.4) | 4 (8.9) |
| | Akathisia/Restlessness | 1 (2.2) | 1 (2.2) |
| | Cognitive Disorder | 1 (2.2) | 0 |
| | Drooling | 1 (2.2) | 0 |
| | Dyskinesia | 1 (2.2) | 0 |
| | Migraine | 1 (2.2) | 0 |
| | Headache | 0 | 3 (6.7) |
| | Loss of Consciousness | 0 | 1 (2.2) |
| | Syncope | 0 | 1 (2.2) |
| GENERAL DISORDERS | Irritability | 3 (6.7) | 6 (13.3) |
| | Fatigue | 3 (6.7) | 2 (4.4) |
| | Gait disturbance | 1 (2.2) | 0 |
| | Chest pain | 1 (2.2) | 0 |
| | Hangover | 1 (2.2) | 0 |
| GASTRO-INTESTINAL DISORDERS | Diarrhea | 4 (8.9) | 0 |
| | Dry mouth | 4 (8.9) | 3 (6.7) |
| | Constipation | 2 (4.4) | 1 (2.2) |
| | Nausea | 1 (2.2) | 2 (4.4) |
| | Abdominal pain upper | 1 (2.2) | 0 |
| | Dyspepsia | 1 (2.2) | 0 |
| | Frequent bowel movements | 1 (2.2) | 0 |
| | Gastrointestinal pain | 1 (2.2) | 0 |
| | Vomiting | 0 | 3 (6.7) |
| | Dysphagia | 0 | 1 (2.2) |
| | Flatulence | 0 | 1 (2.2) |
| | Salivary hypersecretion | 0 | 1 (2.2) |

Safety. In addition to AE reporting, rating scales were used to monitor for potential subclinical toxicity due to excessive monoamine depletion. Such safety scales were employed in the tetrabenazine development program. These scales applied in First-HD included the Hospital Anxiety and Depression Scale (HADS), the Columbia Suicide Severity Rating Scale (C-SSRS), the Swallowing Disturbance Questionnaire (SDQ), the Unified Parkinson's Disease Rating Scale (dysarthria item) (UPDRS [dysarthria]), the Barnes Akathisia Rating Scale (BARS), and the Epworth Sleepiness Scale (ESS). In addition, the UHDRS, which includes cognitive, behavioral, and functional measures, was performed at key visits.

These safety scales showed that deutetrabenazine did not cause depression, anxiety, suicidality, akathisia, somnolence, or difficulty speaking, as between group difference on the scales were small and not clinically significant. In fact, swallowing function, which is an important cause of morbidity and mortality in patients with HD, was shown to significantly improve in deutetrabenazine-treated subjects compared with placebo and was consistent with improvement seen in motor function. The clinical relevance of this improvement is described below.

Figure 2:
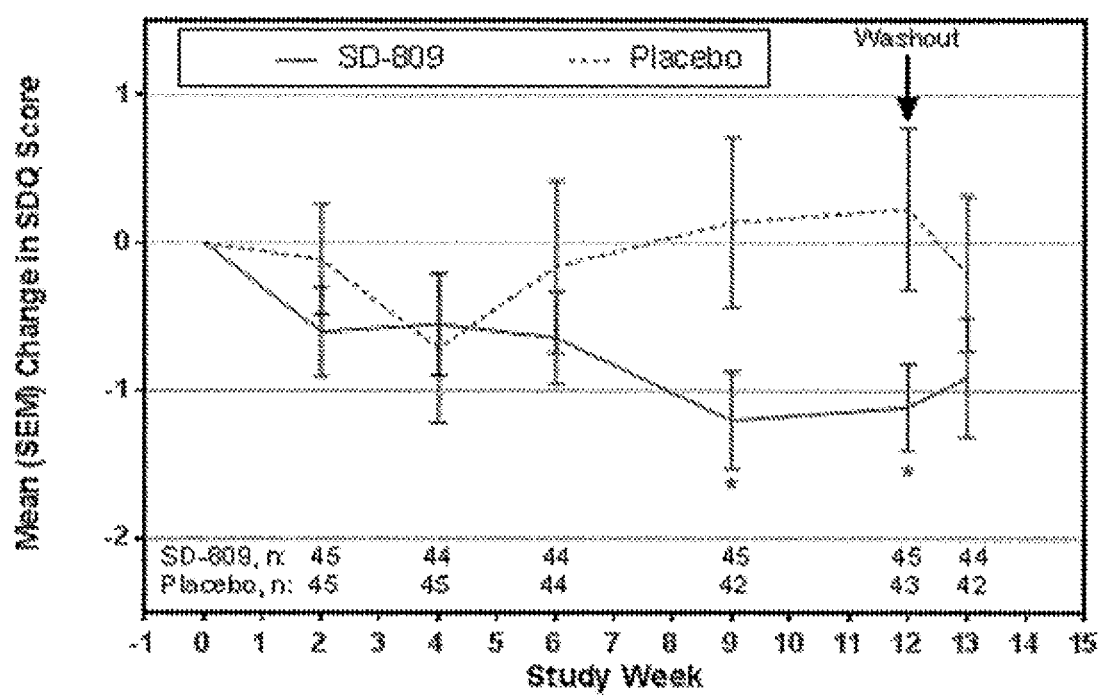
FIG. 2 presents the mean change from baseline in swallowing disturbance over time for deutetrabenazine and placebo (as determined by questionnaire), demonstrating a significant improvement in swallowing with deutetrabenazine treatment.
Figure 3:
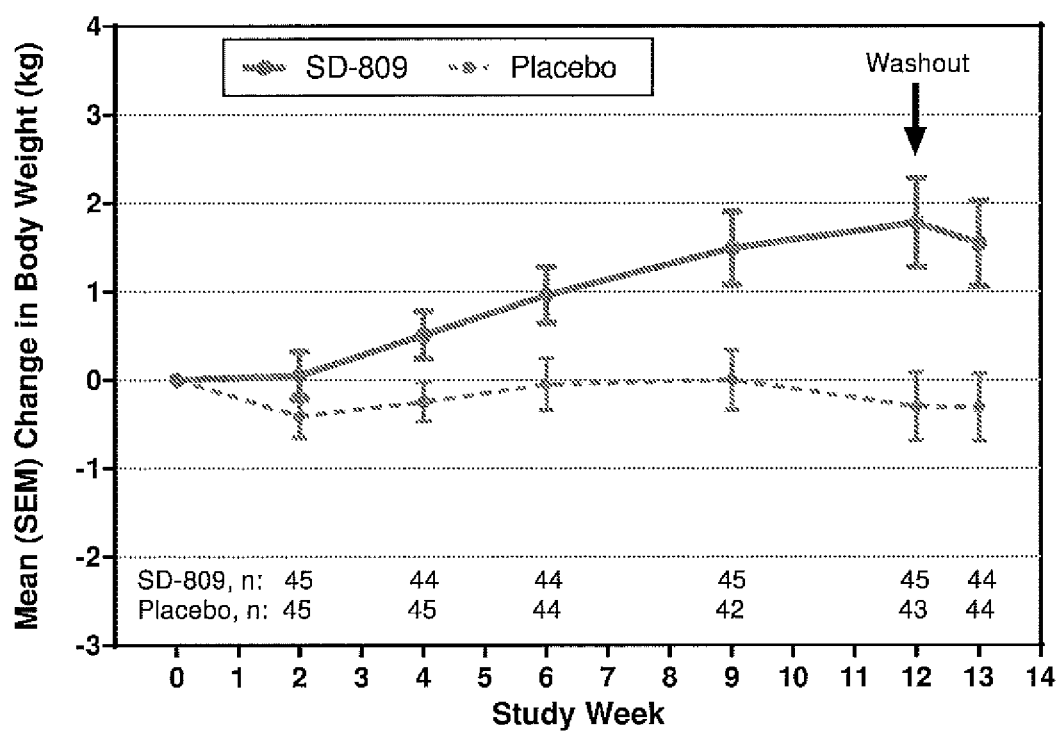
FIG. 3 presents the mean change from baseline in body weight (kg) over time for deutetrabenazine and placebo from the First-HD study.

Swallowing Disturbance. The Swallowing Disturbance Questionnaire (SDQ) was used prospectively to assess swallowing impairment during the study, as dysphagia is a common problem in patients with HD. This 15-item assessment has been validated in patients with Parkinson's disease and has been shown to be a sensitive and accurate tool for identifying patients with swallowing disturbances arising from different etiologies. The SDQ is recommended by the National Institute of Neurological Disorders and Stroke Common data elements for assessing swallowing impairment in Parkinson's disease, and thus is also relevant for patients with HD, given they may have bradykinesia and other parkinsonian symptoms as part of their illness. FIG. 2 presents the mean change from baseline in the SDQ by over time, demonstrating a significant improvement in swallowing with deutetrabenazine treatment, compared with placebo.

Additional UHDRS Assessments. The UHDRS rating scale was assessed throughout the First-HD Study to monitor for safety. Evaluation of the parkinsonism subscore of the UHDRS Motor Assessment (Part I) did not identify evidence of parkinsonism in subjects treated with deutetrabenazine or placebo, consistent with the absence of extrapyramidal symptom AEs. These results were further supported by the lack of meaningful changes in either treatment group on the UPDRS dysarthria question.

The results of the UHDRS Cognitive Assessment (Part II) also demonstrated no meaningful changes from baseline or consistent trends between treatment groups, indicative of no decline in cognitive function with treatment.

Figure 4:
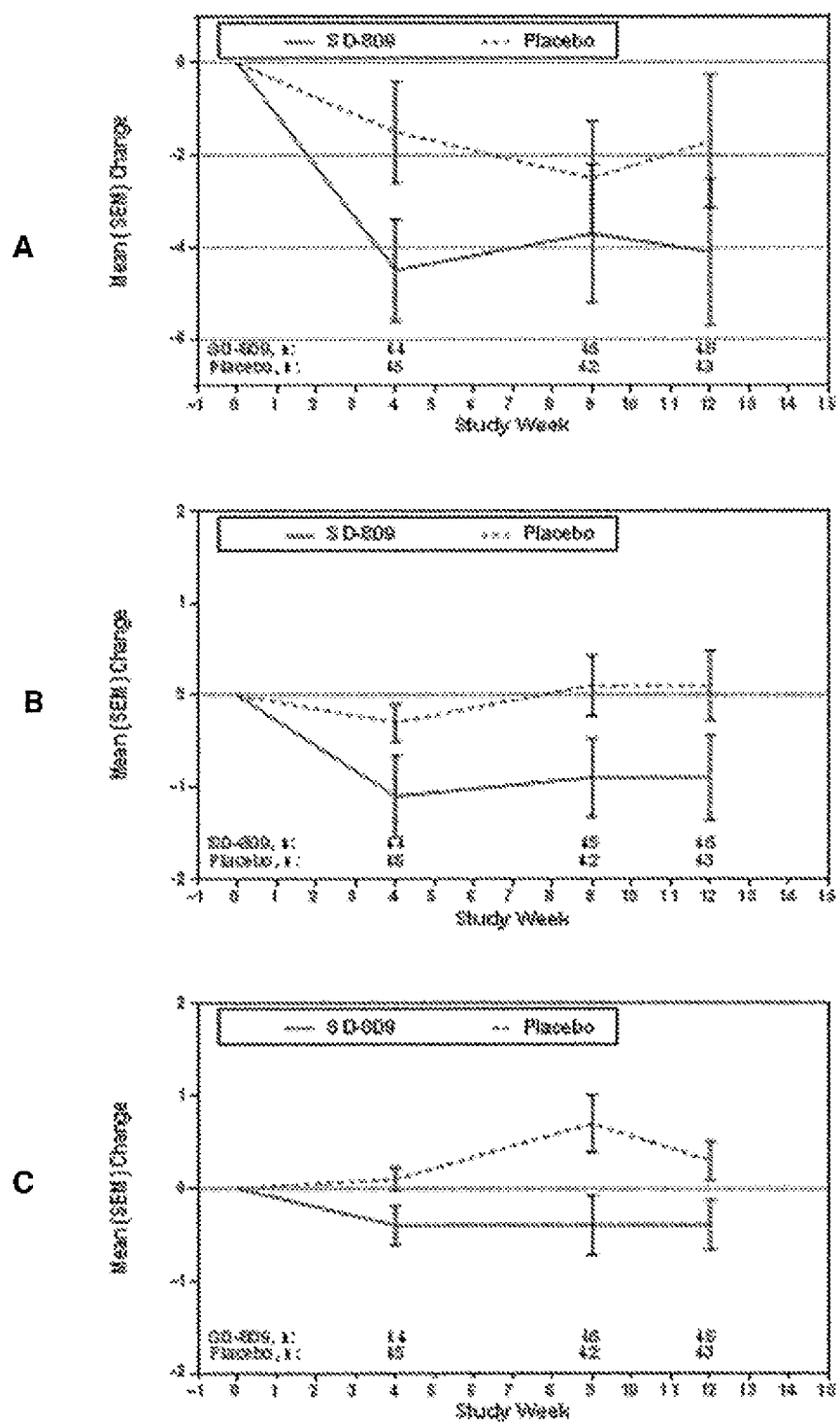
FIG. 4 shows the mean total behavior score (A), anxiety (B) and compulsive behavior (C) for deutetrabenazine-treated subjects compared with the placebo group, from the First-HD study.
Figure 5:
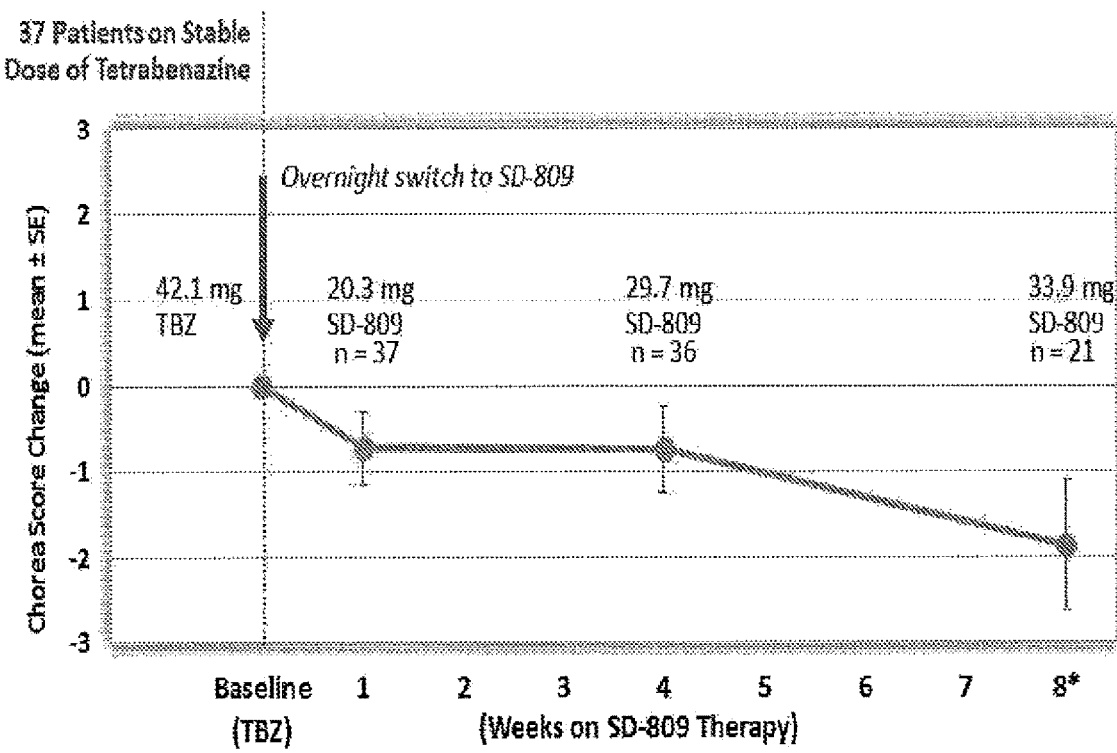
FIG. 5 shows change in mean chorea score observed in patients switched from tetrabenazine to deutetrabenazine, and the mean daily dose of tetrabenazine or deutetrabenazine corresponding to the chorea score, from the ARC-HD study. In the figure, the asterisk (*) at week 8 indicates p=0.0252.

The UHDRS Behavioral Assessment (Part III) demonstrated improvement in the in the mean total behavior score for deutetrabenazine-treated subjects compared with the placebo group, however the difference did not achieve statistical significance. Importantly, there was no worsening of depressed mood, apathy, self-esteem, irritability, aggressive behavior, suicidal thoughts, hallucinations, or delusions. The improvement in the overall score was driven by differences in anxiety and compulsive behavior (FIG. 4 A-C).

The UHDRS Functional Assessment Score (Part IV), Independence Scale Score (Part V) and the Total Functional Capacity Score (Part VI), which were assessed at Baseline and again at Week 12, did not show clinically relevant changes from baseline in either treatment group or differences between the treatment groups.

Minor fluctuations in vital signs (blood pressure, heart rate, respiratory rate, and temperature) were observed during the study; these changes were generally similar in the deutetrabenazine and placebo treatment groups and were not assessed as clinically significant. No consistent between group differences were observed. In addition, there was no evidence that hypotension, dizziness, or orthostasis was associated with deutetrabenazine treatment.

Body weight. Compared with the placebo group, deutetrabenazine treatment led to a mean weight gain of approximately 2.1 kg over placebo (at week 12, mean (SD) change in body weight of +1.8 (3.4) kg for deutetrabenazine vs −0.30 (2.5) kg in placebo (treatment effect, +2.1 kg). Weight gain correlates with improved treatment outcome and health in chorea patients, and may result in part from reduced chorea (whereby the improved swallowing may lead to better intake of food, which when combined with less caloric energy used due to reduced abnormal involuntary movements, may translate into weight gain), in addition to improved function or behavioral symptoms such as anxiety, which may suppress appetite.

Adverse Events and Safety: comparison to tetrabenazine. The variable pharmacokinetics of tetrabenazine can affect its tolerability and limit its clinical use. The half-lives of the circulating active metabolites, α- and β-dihydrotetrabenazine, are short. These short half-lives necessitate frequent dosing and result in large fluctuations in plasma concentrations. The high peak concentrations and variability in plasma levels associated with tetrabenazine may contribute to the poor tolerability that is often observed.

Accordingly, the prescribing information for tetrabenazine contains several warnings regarding adverse effects and the potential for safety issues:

A boxed warning indicates that tetrabenazine increases the risk of depression and suicidal thoughts and behavior (suicidality) in patients with HD.

High rates of treatment-emergent adverse events were observed in patients treated with tetrabenazine compared with placebo-treated patients, including somnolence/sedation, insomnia, depression, akathisia, anxiety, and fatigue (see Table #13 below).

Dose escalation was discontinued or dosage of study drug was reduced due to adverse events in 52% (28 of 54) of patients randomized to tetrabenazine.

In the 12-week, randomized controlled trial of tetrabenazine, adverse events suggestive of parkinsonism (e.g., parkinsonism, bradykinesia, hypertonia, rigidity) were observed in 15% of tetrabenazine patients compared with 0% of placebo patients.

A Warning and Precaution cites the risk of dysphagia, an underlying symptom of HD and a known side effect of reduced dopaminergic neurotransmission. Although low rates of dysphagia were reported in the 12-week trial, in open-label studies, dysphagia was observed in 8% to 10% of tetrabenazine-treated patients, with some cases associated with aspiration pneumonia. It is unclear whether these cases were associated with treatment, however FDA expressed concern that events of dysphagia, which can have devastating clinical consequences, may have been significantly underestimated in the tetrabenazine NDA. Of note, in a retrospective study of 98 patients treated with tetrabenazine for hyperkinetic movement disorders, dysphagia was observed in 19% of patients.

At 50 mg, tetrabenazine caused an approximately 8 ms mean increase in QTc interval (90% two-sided Confidence Interval [CI]: 5.0, 10.4 ms).

The safety profile of tetrabenazine observed in the 12-week, controlled trial is reflected in the prescribing information, as summarized below.

TABLE 13

Treatment Emergent Adverse Reactions in Patients Treated with Tetrabenazine Occurring with a Greater Frequency than Placebo in 12-Week, Double-Blind, Placebo-Controlled Trial of Tetrabenazine

| Body System | Preferred Term | Tetrabenazine (N = 54) n (%) | Placebo (N = 30) n (%) |
|---|---|---|---|
| PSYCHIATRIC DISORDERS | Sedation/somnolence | 17 (31) | 1 (3) |
| | Insomnia | 12 (22) | 0 |
| | Depression | 10 (19) | 0 |
| | Anxiety/anxiety aggravated | 8 (15) | 1 (3) |
| | Irritability | 5 (9) | 1 (3) |
| | Appetite decreased | 2 (4) | 0 |
| | Obsessive reaction | 2 (4) | 0 |
| CENTRAL & PERIPHERAL NERVOUS SYSTEM | Akathisia | 10 (19) | 0 |
| | Balance difficulty | 5 (9) | 0 |
| | Parkinsonism/ bradykinesia | 5 (9) | 0 |
| | Dizziness | 2 (4) | 0 |
| | Dysarthria | 2 (4) | 0 |
| | Gait unsteady | 2 (4) | 0 |
| | Headache | 2 (4) | 1 (3) |
| GASTRO-INTESTINAL SYSTEM DISORDERS | Nausea | 7 (13) | 2 (7) |
| | Vomiting | 3 (6) | 1 (3) |
| BODY AS A WHOLE GENERAL | Fatigue | 12 (22) | 4 (13) |
| | Fall | 8 (15) | 4 (13) |
| | Laceration (head) | 3 (6) | 0 |
| | Ecchymosis | 3 (6) | 0 |
| RESPIRATORY SYSTEM DISORDERS | Upper respiratory tract infection | 6 (11) | 2 (7) |
| | Shortness of breath | 2 (4) | 0 |
| | Bronchitis | 2 (4) | 0 |
| URINARY SYSTEM DISORDERS | Dysuria | 2 (4) | 0 |

In comparison to deutetrabenazine, tetrabenazine appears to produce more adverse effects.

ARC-HD

In a second clinical trial, a method for converting patients with adequate control of chorea with tetrabenazine to deutetrabenazine treatment was implemented. Alternatives for Reducing Chorea in Huntington Disease (ARC-HD) was an open-label, single-arm study in which subjects with manifest HD who were receiving FDA-approved doses of tetrabenazine for the treatment of chorea or had successfully completed First-HD were invited to participate.

The study thus comprised two cohorts. The Rollover Cohort (75 subjects) successfully completed the First-HD study described above, including a 1-week washout; the Switch Cohort (37 subjects) switched overnight from stable dosing (≥8 weeks) with tetrabenazine to deutetrabenazine based on a conversion method designed to achieve comparable systemic exposure to total α and β metabolites. Other key inclusion criteria for the study included: diagnosed with manifest HD, as indicated by characteristic motor examination features; a documented expanded cytosine adenine guanine (CAG) repeat (≥37) and Total Functional Capacity (TFC) score ≥5 at or before Screening; able to ambulate without assistance for at least 20 yards (assistive devices such as walker or cane permitted); and subject has a reliable caregiver who interacts with the subject on a daily basis, oversees study drug administration, assures attendance at study visits, and participates in evaluations, as required. Key exclusion criteria included serious untreated or undertreated psychiatric illness (e.g., depression) at Screening or Baseline; concomitant dopamine receptor antagonists, dopamine agonists, levodopa, reserpine, N-methyl-D-aspartate receptor antagonists, or monoamine oxidase inhibitors within 30 days of Screening or Baseline; and score ≥11 on the depression subscale of the Hospital Anxiety and Depression Scale (HADS), a score of ≥11 on the Swallowing Disturbance Questionnaire (SDQ), or a Unified Parkinson's Disease Rating Scale (UPDRS) dysarthria score of ≥3 at Screening or Baseline.

Participants were 58% male, 95% White, and had a mean age of 54 years. The mean (SD) TMC score at Baseline was 12.2 (4.6) and the mean (SD) CAG repeat length was 44 (3.7)

Study Design

The guidance for investigators on conversion of subjects from stable doses of tetrabenazine to deutetrabenazine in the ARC-HD Switch study was designed to minimize the risk that dose conversion would result in either loss of efficacy or increased adverse events. The conversion method applied was based on modeling and simulation of Phase 1 pharmacokinetic data for deutetrabenazine and tetrabenazine. The objective of the pharmacokinetic analysis was to identify an initial dosing regimen of deutetrabenazine predicted to provide exposure at steady state of the active α and β metabolites that was less than or equal to the predicted AUC at steady state of the active alpha and beta metabolites of tetrabenazine, but with a lower Cmax.

In a Phase 1 single-center, open-label, crossover clinical trial, each of 24 healthy volunteer subjects received single doses of 25 mg of tetrabenazine and 15 mg of deutetrabenazine. One of the objectives of the clinical trial was to evaluate and compare the safety of deutetrabenazine relative to tetrabenazine.

Subjects in the Switch cohort completed a full screening evaluation. Subjects who were eligible to enroll in the study were subsequently converted from their tetrabenazine dose regimen to a deutetrabenazine dose regimen predicted to be comparable to their existing tetrabenazine regimen. Subjects received existing tetrabenazine regimen through midnight of Day 0 and switched to their assigned deutetrabenazine regimen the next morning (Day 1 of the study). The initial dose was based on a conversion method, defined by a Phase 1 pharmacokinetic comparison of deutetrabenazine and tetrabenazine suggesting an initial dose of deutetrabenazine that is approximately 50% of the existing tetrabenazine dose (Table 15). Following the first week of deutetrabenazine treatment, the dose of deutetrabenazine was allowed to be adjusted upward or downward once per week in increments of 6 mg/day until a dose that adequately controls chorea was identified, the subject experienced a protocol defined "clinically significant" adverse event, or the maximal allowable dose was reached. The investigator, in consultation with the subject and caregiver, determined when an adequate level of chorea control had been achieved. If a subject experienced a "clinically significant" adverse event attributable to deutetrabenazine, the investigator determined if a dose reduction or suspension was necessary.

TABLE 15

Method for Converting Patients from Tetrabenazine to deutetrabenazine Therapy

| Incoming Total Daily Tetrabenazine Dose | Initial Total Daily deutetrabenazine Dose | Initial Total Daily deutetrabenazine Dose Regimen | | Subsequent deutetrabenazine Dosing Regimen |
|---|---|---|---|---|
| | | Morning Dose | Evening Dose | |
| 12.5 mg | 6 mg | 6 mg | — | Dose adjusted upward or downward in 6-mg/day increments once per week to achieve dose that adequately controls chorea |
| 25 mg | 12 mg | 6 mg | 6 mg | |
| 37.5 mg | 18 mg | 9 mg | 9 mg | |
| 50 mg | 24 mg | 12 mg | 12 mg | |
| 62.5 mg | 30 mg | 15 mg | 15 mg | |
| 75 mg | 36 mg | 18 mg | 18 mg | |
| 87.5 mg | 42 mg | 21 mg | 21 mg | |
| 100 mg | 48 mg | 24 mg | 24 mg | |

Subjects in the Rollover cohort completed a 1-week washout at the conclusion of First-HD, during which mean TMC scores returned to baseline. The deutetrabenazine dose for these subjects was titrated from a starting dose of 6 mg per day to a dose that controlled chorea and was well tolerated.

For both cohorts, oral tablets at strengths of 6 mg, 9 mg, and 12 mg were used. Doses of 12 mg and higher were administered in two divided doses approximately 10 hours apart. All study treatment regimens were administered orally with meals. The maximum total daily dose of deutetrabenazine was set at 72 mg per day, unless the subject was receiving a strong CYP2D6 inhibitor (e.g., paroxetine), in which case the maximum total daily dose was 36 mg.

Subjects attended regular clinic visits to evaluate safety and establish an optimal dose. The investigator, in consultation with the subject and caregiver, determined when an adequate level of chorea control was achieved; the dose of DTBZ could be increased on a weekly basis until there was adequate control of chorea, the subject experienced a protocol defined clinically significant adverse event, or the maximal allowable dose was reached. During long-term treatment, all subjects had regular contact with the study site for evaluation of safety and chorea control. Long-term treatment will continue until deutetrabenazine becomes commercially available in the U.S.

A total of 37 subjects with chorea associated with HD that was adequately controlled with tetrabenazine who had converted from tetrabenazine to deutetrabenazine treatment in ARC-HD Switch were included in an analysis conducted to assess maintenance of chorea control following dose conversion. The subjects included in the analysis were each converted from tetrabenazine treatment to a deutetrabenazine daily dose, administered twice daily, that was approximately 30% to 50% of their prior total daily tetrabenazine dose.

Results

Dose & Efficacy. Given the differences in prior therapy and expected changes in chorea control following initiation of deutetrabenazine therapy in the two cohorts, efficacy data are summarized separately for these two groups. Data from the two cohorts is provided below through Week 15. As this study is ongoing, data from subsequent weeks are still being gathered and analyzed, and results comprise too few patients to draw meaningful conclusions at this stage.

Dose—Switch Cohort. The mean dose of TBZ at baseline was 42 mg and, after the overnight switch, the mean dose of deutetrabenazine was 20 mg. Mean daily doses of deutetrabenazine following the switch from TBZ are given below in Table 15.

TABLE 15

TBZ Dose at Baseline and DTBZ Dose Conversion and Titration

| | | DTBZ Daily Dose (mg) | | | |
| --- | --- | --- | --- | --- | --- |
| Statistic | TBZ Dose at Baseline (mg) | Day 1 through Week 1 | Week 4 | Week 8 | Week 15 |
| n | 37 | 37 | 36 | 22 | 15 |
| Mean (SD) Dose | 42.1 (19.58) | 20.3 (10.23) | 29.7 (10.44) | 33.5 (11.36) | 36.0 (14.70) |
| Minimum, Maximum | 12.5, 100 | 6, 48 | 12, 48 | 12, 48 | 12, 60 |

Dose—Rollover Cohort. Mean daily doses of deutetrabenazine following wash-out and initial doses of 6 mg/day are given below in Table 16.

TABLE 16

DTBZ Daily Dose Titration

| | DTBZ Daily Dose (mg) | | | |
| --- | --- | --- | --- | --- |
| Statistic | Week 2 | Week 4 | Week 8 | Week 15 |
| n | 62 | 56 | 44 | 34 |
| Mean (SD) Dose | 11.8 (1.07) | 24.2 (4.57) | 38.9 (11.09) | 41.1 (9.24) |
| Minimum, Maximum | 6, 12 | 6, 36 | 6, 48 | 18, 48 |

Figure 6:
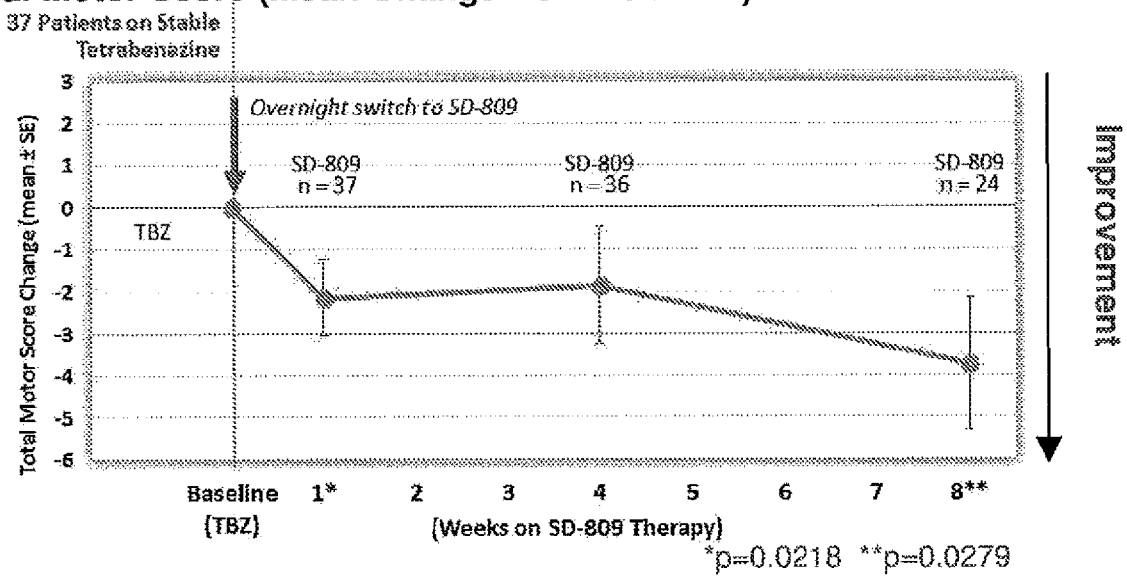
FIG. 6 shows change in mean total motor score observed in patients switched from tetrabenazine to deutetrabenazine from the ARC-HD study.

Total Maximal Chores (TMC)—Switch Cohort. One week following the switch to deutetrabenazine, at a time when subjects were still receiving their initial total daily deutetrabenazine dose, the mean total chorea score decreased by approximately one point from baseline (mean±standard error [SE] change from baseline was −0.72±2.6), indicating that deutetrabenazine maintained chorea control in these subjects. A subset of 35 subjects also had chorea assessed four weeks after switching to deutetrabenazine. In this set of subjects, the mean (±SE) change from baseline was −0.7±3.0 at Week 4, providing further demonstration of maintenance of chorea control. In addition, data from 21 patients were available at Week 8; these data demonstrated change from baseline of −1.9±3.5 units on the TMC score; at week 15, −1.2±4.1 units. Results are given below in Table 17. A summary of the change in mean chorea score observed and the mean daily dose of tetrabenazine or deutetrabenazine corresponding to the chorea score is provided in FIG. 6.

TABLE 17

Total Maximal Chorea Score (Switch Cohort)

| | Total Maximal Chorea Score | | | | |
| --- | --- | --- | --- | --- | --- |
| Time Point | n | Mean (SD) Score | n | Mean (SD) Change from Baseline | p-value$^a$ |
| Baseline | 37 | 12.47 (5.26) | — | — | — |
| Week 1 | 37 | 11.76 (5.11) | 37 | −0.72 (2.59) | 0.1007 |
| Week 4 | 36 | 11.86 (5.23) | 36 | −0.74 (3.01) | 0.1507 |
| Week 8 | 21 | 10.10 (5.56) | 21 | −1.86 (3.52) | 0.0252 |
| Week 15 | 15 | 10.87 (5.99) | 15 | −1.17 (4.07) | 0.2850 |

Total Maximal Chores (TMC)—Rollover Cohort. At Week 2, a statistically significant mean (SD) decrease from Baseline of 1.9 (3.0) units was observed (p<0.0001). This effect persisted through Week 15, at which time the mean (SD) decrease from baseline was 4.5 (5.0) units (p=0.0001). These results are consistent with those observed for DTBZ in First-HD. Results are given below in Table 18.

TABLE 18

Total Maximal Chorea Score (Rollover Cohort)

| | Total Maximal Chorea Score | | | | |
| --- | --- | --- | --- | --- | --- |
| Time Point | n | Mean (SD) Score | n | Mean (SD) Change from Baseline | p-value$^a$ |
| Baseline | 71 | 12.0 (4.25) | — | — | — |
| Week 2 | 61 | 10.1 (3.41) | 58 | −1.9 (2.95) | <0.0001 |
| Week 4 | 55 | 9.8 (3.69) | 52 | −2.5 (3.21) | <0.0001 |
| Week 8 | 43 | 7.9 (3.91) | 40 | −4.5 (3.34) | <0.0001 |
| Week 15 | 34 | 7.9 (4.05) | 33 | −4.5 (4.04) | <0.0001 |

Total Motor Score (TMS)—Switch Cohort. Additionally, overall motor symptoms, as assessed by the TMS, were maintained following dose conversion and appeared to improve at Week 8, as indicated by a mean (SD) change from baseline in TMS of −3.7 (7.8). Results are given below in Table 19.

TABLE 19

Total Motor Score Over Time (Switch Cohort)

| | Total Motor Score | | | | |
| --- | --- | --- | --- | --- | --- |
| Time Point | n | Mean (SD) Score | n | Mean (SD) Change from Baseline | p-value$^a$ |
| Baseline | 37 | 38.49 (18.679) | — | — | — |
| Week 1 | 37 | 36.35 (18.043) | 37 | −2.14 (5.414) | 0.0218 |

TABLE 19-continued

Total Motor Score Over Time (Switch Cohort)

| | | Total Motor Score | | | |
|---|---|---|---|---|---|
| Time Point | n | Mean (SD) Score | n | Mean (SD) Change from Baseline | p-value[a] |
| Week 4 | 36 | 37.14 (19.516) | 36 | −1.85 (8.419) | 0.1966 |
| Week 8 | 24 | 34.58 (18.268) | 24 | −3.73 (7.787) | 0.0279 |
| Week 15 | 15 | 35.00 (22.984) | 15 | −1.93 (10.910) | 0.5037 |

Figure 7:
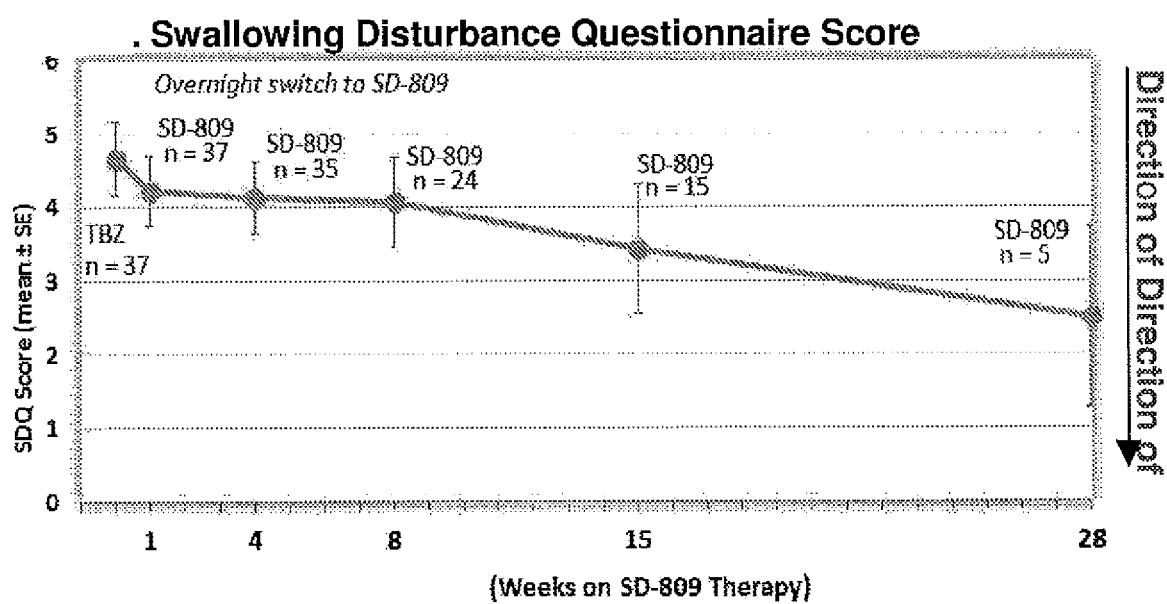
FIG. 7 presents the mean change from baseline in swallowing disturbance over time in patients switched from tetrabenazine to deutetrabenazine (as determined by questionnaire) from the ARC-HD study, demonstrating a trend toward improvement in swallowing with deutetrabenazine treatment.
Figure 8:
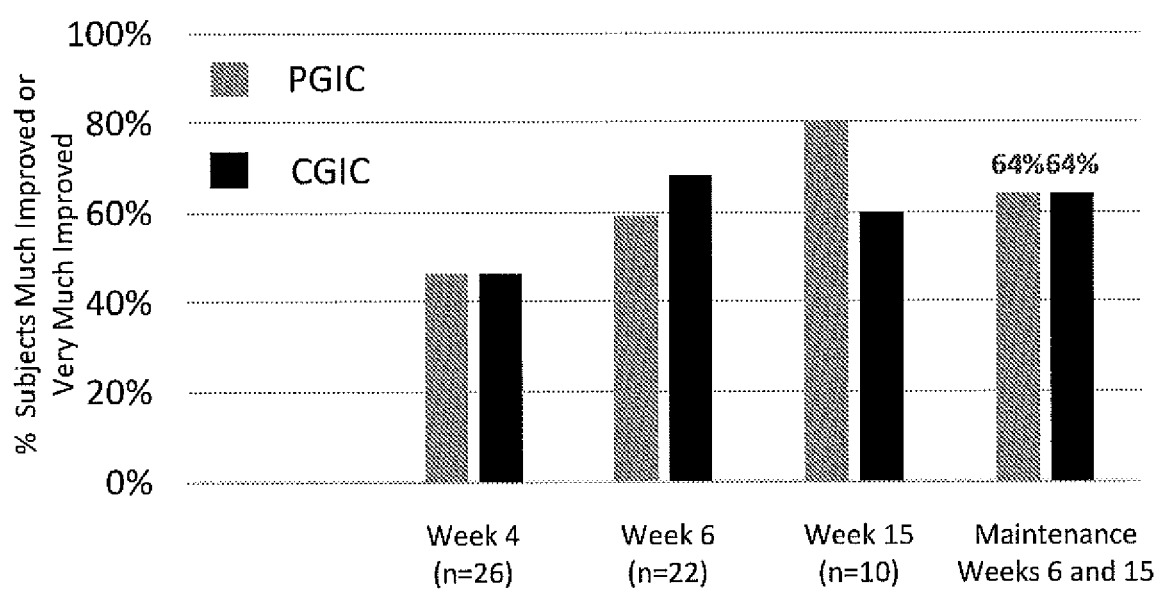
FIG. 8 shows the open-label long-term data in tardive dyskinesia patients from a tardive dyskinesia study as percent of treated subjects who were much improved or very much improved on a seven-point Likert scale of Patient Global Impression of Change (PGIC) and Clinical Global Impression of Change (CGIC).

A summary of the change in mean chorea score observed and the mean daily dose of tetrabenazine or deutetrabenazine corresponding to the chorea score is provided in FIG. 7.

Total Motor Score (TMS)—Rollover Cohort. Statistically significant mean decreases in TMS from baseline were observed as early as Week 2 (3.9 units; p<0.0001) and persisted through Week 15 (8.0 units; p=0.0001). Results are given below in Table 20.

TABLE 20

Total Motor Score (Rollover Cohort)

| | | Total Motor Score | | | |
|---|---|---|---|---|---|
| Time Point | n | Mean (SD) Score | n | Mean (SD) Change from Baseline | p-value[a] |
| Baseline | 71 | 35.3 (16.34) | — | — | — |
| Week 2 | 61 | 32.4 (15.23) | 58 | −3.9 (6.67) | <0.0001 |
| Week 4 | 55 | 32.1 (16.84) | 52 | −5.9 (7.88) | <0.0001 |
| Week 8 | 43 | 31.0 (18.07) | 40 | −8.3 (8.58) | <0.0001 |
| Week 15 | 35 | 30.5 (17.70) | 33 | −8.0 (8.41) | <0.0001 |

The fact that the mean TMS improvement ((−3.7 units at Week 8 in the Switch cohort and −8.0 units at Week 15 in the Rollover cohort) was greater in magnitude than the mean TMC score improvement (−1.9 units at Week 8 in the Switch cohort and −4.5 units at Week 15 in the Rollover cohort) suggests a benefit of DTBZ treatment on other motor symptoms of HD, in addition to the reduction in chorea.

It is expected that other deuterium substituted tetrabenazines and valbenazines will be efficacious in the treatment of chorea and other symptoms associated with Huntington's disease and other movement disorders, as well as abnormal involuntary movements generally.

Adverse Events. DTBZ was generally well tolerated, with safety results in both the Rollover and Switch Cohorts consistent with the safety profile observed in First-HD.

In the Rollover Cohort, 39 (52.0%) subject experienced AEs, with the AEs assessed as mild or moderate in intensity in 36 (92.3%) of these 39 subjects. The most common AEs in the Rollover Cohort were fall (10 subjects, [13%]), somnolence (6 [8%]), depression (6 [8%]), and insomnia (6 [8%]). A similar percentage of subjects in the Rollover Cohort experienced AEs from Day 1 through Week 8 (45.3%) compared with Week 8 through the visit cut-off date (43.2%). Five subjects had an AE that led to a dose reduction or dose suspension. Three subjects experienced serious AEs (anxiety, major depression, suicidal ideation, dehydration, encephalopathy, and depression suicidal), with one of these serious AEs (major depression) leading to study withdrawal. Three additional subjects withdrew from the study due to an AE (worsening chorea, suicidal ideation, and depression).

In the Switch Cohort, 21 (56.8%) subjects experienced at least one AE, with AEs assessed as mild to moderate in intensity in 20 (95.2%) of the 21 subjects. The most common AEs in the Switch Cohort were somnolence (9 subjects [24%]), anxiety (3 [8%]), and fall (3 [8%]). The majority of these common events occurred during the first 8 weeks of the study (22 Switch subjects had reached Week 8 by the visit cut-off date). The most common AEs occurred at similar rates from Day 1 through Week 1, Week 2 through Week 4, and Week 5 through Week 8. There were no adverse events of chorea or worsening chorea during the reporting period, including the first week after the conversion from tetrabenazine to deutetrabenazine. Two subjects experienced serious AEs (pneumonia and dehydration), no subjects withdrew from the study due to an AE, and four subjects had an AE that led to a dose reduction or dose suspension.

There were no apparent increases in the overall incidence of AEs in subjects with impaired CYP2D6 metabolism (including subjects using a strong CYP2D6 inhibitor and CYP2D6 poor metabolizers).

Frequent treatment-emergent AEs, defined as events occurring in at least 4% of subjects across all time periods in either cohort, are summarized below in Table 21. The most common AEs during the Entire Treatment Period in the Rollover Cohort were fall (10 subjects, [13.3%]), somnolence (6 [8.0%]), depression (8 [10.7%]), and insomnia (6 [8.0%]). The most common AEs during the Entire Treatment Period in the Switch Cohort were fall (3 subjects, [8.1%]), somnolence (9 [24.3%], but most were transient and did not require dose adjustment), depression (8 [10.7%]), and anxiety (3 [8.1%]). The types of common adverse events observed were consistent with those observed with deutetrabenazine treatment in First-HD. Falls are difficult to assess in this study population with chorea and HD; the majority of the falls were not considered to be related to study drug.

TABLE 21

TEAEs Occurring in at Least 4% of Subjects in Either Cohort

| Event | Rollover Cohort (N = 75) n (%) | Switch Cohort (N = 37) n (%) |
|---|---|---|
| Fall | 10 (13.3) | 3 (8.1) |
| Depressiona | 8 (10.7) | 2 (5.4) |
| Somnolence | 6 (8.0) | 9 (24.3) |
| Insomnia | 6 (8.0) | 1 (2.7) |
| Diarrhoea | 4 (5.3) | 2 (5.4) |
| Anxiety | 3 (4.0) | 3 (8.1) |
| Constipation | 3 (4.0) | 2 (5.4) |
| Dry mouth | 3 (4.0) | 2 (5.4) |
| Irritability | 3 (4.0) | 2 (5.4) |
| Vomiting | 3 (4.0) | 1 (2.7) |
| Fatigue | 3 (4.0) | 1 (2.7) |
| Sleep disorder | 3 (4.0) | 0 |
| Nasopharyngitis | 2 (2.7) | 2 (5.4) |
| Disorientation | 0 | 2 (5.4) |

Additional Safety Measures. Safety scales were incorporated into the study design to monitor for subclinical toxicity associated with deutetrabenazine treatment. These included observed values and changes in the UHDRS, SDQ, UPDRS dysarthria question, Barnes Akathisia Rating Scale (BARS), HADS, Epworth Sleepiness Scale (ESS), Columbia Suicide Severity Rating Scale (C-SSRS), and Montreal Cognitive Assessment (MoCA©). The overall analysis of the safety scales showed no increased risk with deutetrabenazine treatment through Week 28 as of the visit cut-off date for this study. Eight Rollover patients had apparent decline in two of four cognitive measures (MoCA and the verbal fluency task) at Week 28. These changes were often associated with AEs (e.g., somnolence, fatigue, urinary tract infection) and were typically not associated with reduced performance on functional measures. No clinically relevant changes in vital signs, ECGs, or clinical laboratory assessments were observed during the study. Regarding body weight, from baseline through Week 15, body weight increased in the Rollover cohort and changed minimally in the Switch Cohort. Following Week 15, there was a trend toward weight loss at Week 28 in both cohorts (Rollover Cohort, 1.4 kg; Switch cohort 1.9 kg), however the decrease in the number of subjects that reached the Week 28 milestone limits the interpretation of these results.

Taken together, the results of this study support deutetrabenazine as an effective therapeutic option, with a favorable safety profile, for treatment of chorea associated with HD. The results support the safety of an overnight switch from TBZ to a predicted AUC-matched dose of deutetrabenazine, which can be achieved without a loss of chorea control.

Tardive Dyskinesia

An open-label, single-arm study in which male and female subjects with moderate to severe drug-induced tardive dyskinesia (TD) was conducted to evaluate the safety and tolerability of long-term maintenance therapy with deutetrabenazine, and to evaluate the efficacy of long-term maintenance therapy of deutetrabenazine to reduce the severity of abnormal involuntary movements of TD.

Study Design. Inclusion criteria included: at least 18 years of age; successful completion of prior deutetrabenazine controlled study for treatment of moderate to severe TD; history of using a dopamine receptor antagonist for at least 3 months (or 1 month in subjects 60 years of age and older); clinical diagnosis of TD and has had symptoms for at least 3 months; for subjects with underlying psychiatric illness:
  psychiatrically stable and no change in psychoactive medications for ≥30 days before screening (45 days for antidepressants);
  subjects on long acting (depot) medications have been on stable therapy (dose, frequency) for ≥3 months before Screening; and
  subject has a mental health provider who is aware of the subject's participation in the trial and does not anticipate any changes to the subject's treatment regimen (drug, dose, frequency) in the next 3 months;
history of being compliant with prescribed medications; able to swallow study drug whole; lives in a stable environment, and has adequate supervision when necessary to comply with all study procedures, attend all study visits, and safely participate in the trial; sufficient reading skills to comprehend the subject-completed rating scales; female subjects of childbearing potential agree to use one of the following acceptable methods of contraception from screening through study completion if sexually active:
IUD or intrauterine system in place for at least 3 months prior to screening;
Subject or partner using barrier method with spermicide from screening through study completion;
Partner has a documented vasectomy >6 months prior to enrollment; or
Stable hormonal contraception (with approved oral, transdermal, or depot regimen) for at least 3 months prior to screening;
Exclusion criteria included: subject has received tetrabenazine within 7 days of baseline, or any of the following medications within 30 days of Baseline: reserpine, α-methyl-p-tyrosine (AMPT), botulinum toxin (within 3 months of Baseline), and medications with strong anticholinergic activity (trihexyphenidyl, benztropine, orphenadrine, procyclidine, and biperiden), metoclopramide, promethazine, prochlorperazine, stimulants (i.e., methylphenidate, amphetamine/dextroamphetamine, lisdexamphetamine, etc.), monoamine oxidase inhibitors, and (MAOIs), levodopa or dopamine agonists; subject has a neurological condition other than TD that may interfere with assessing the severity of dyskinesias; serious untreated or undertreated psychiatric illness at baseline; active suicidal ideation at baseline; history of any of the following within 6 months of Baseline: previous intent to act on suicidal ideation with a specific plan (positive answer to question 5 on C-SSRS) irrespective of level of ambivalence at the time of suicidal thought, previous preparatory acts to commit suicide or suicidal behavior, or previous actual, interrupted, or aborted suicide attempt; score ≥11 on the depression subscale of the Hospital Anxiety and Depression Scale (HADS) at baseline; subject is developmentally disabled or has evidence of dementia; subject has an unstable or serious medical illness at baseline; history (within 3 months) or presence of violent behavior; QTcF value >450 ms (males) or >460 ms (females), or >480 ms (with right bundle branch block [RBBB]) on 12-lead electrocardiogram (ECG) at baseline; evidence of hepatic impairment at Screening, as indicated by: aspartate transaminase (AST) or alanine aminotransferase (ALT) >2.5 times the upper limit of normal (ULN), alkaline phosphatase (ALP) or total bilirubin (TBil) >2 times the ULN (but subjects with Gilbert's Syndrome are eligible to participate if approved by the medical monitor, and subjects with abnormalities in two or more of these analytes (AST, ALT, ALP, TBil) must be approved by the Medical Monitor to be enrolled), and prothrombin time >4 sec prolonged; positive Hepatitis B surface antigen (HBsAg); evidence of significant renal impairment at Screening, indicated by a creatinine clearance <50 mL/min, as estimated by the Cockroft-Gault formula; known allergy to tetrabenazine or to any of the components of deutetrabenazine; has participated in an investigational drug or device trial (other than eligible deutetrabenazine study) and received study drug within 30 days (or 5 drug half-lives) of baseline, whichever is longer; subject is pregnant or breastfeeding at baseline; and present use of illicit drugs at baseline.

Dose Regimen. Deutetrabenazine tablets were provided in dosage strengths of 6, 9, 12, 15, and 18 mg. During dose adjustment/titration, deutetrabenazine was supplied in weekly blister cards. During long-term treatment, deutetrabenazine will be supplied in 30-count bottles. Study drug were administered as follows. All treatment regimens were administered twice daily (BID) with meals, approximately 10 hours apart during the day. The starting dose was deutetrabenazine 12 mg/day (6 mg BID) regardless of previous treatment in the parent trial. Prior treatment assignment from the parent trial remained blinded. The maximum total daily dose of deutetrabenazine was 48 mg/day (24 mg BID) unless the subject is on a strong CYP2D6 inhibitor (paroxetine, fluoxetine, or bupropion), in which case the maximum total daily dose is 36 mg/day. Daily doses up to 36 mg/day were given as one tablet BID whereas daily doses of 42 mg/day and 48 mg/day were given as two tablets BID. During the titration period, the dose of deutetrabenazine should be increased on a weekly basis in increments of 6 mg per day until 1) there was adequate control of dyskinesia; 2) the subject experienced a protocol defined clinically significant AE (defined as related to study drug and either a) moderate or severe in intensity or b) meets the criteria for a SAE); or 3) the maximal allowable dose was reached. If a subject experienced a clinically significant AE attributable to deutetrabenazine, the Investigator determined if a dose reduction or suspension was necessary.

Long-Term Treatment. For all subjects participating in the Long-Term Treatment Period, the dose of deutetrabenazine may be adjusted (upward or downward) in increments of 6 mg per day, if necessary, to optimize dyskinesia control while minimizing AEs. However, such changes in dose may not occur more frequently than once per week.

Titration Period (up to 6 weeks). Subjects who successfully completed a parent study were eligible to enroll into this study after a 1-week washout period and the final evaluation. As subjects had discontinued study drug or placebo for 1 week, they underwent deutetrabenazine dose titration in this study. During titration, the investigator, in consultation with the subject determined when an adequate level of dyskinesia control had been achieved. The dose of deutetrabenazine was adjusted (upward or downward) in increments of 6 mg per day up to once per week, until adequate control of dyskinesia was achieved, a clinically significant adverse event related to study drug (either a) moderate or severe in intensity or b) a serious adverse event) occurred, or the maximal allowable dose is reached. If a subject experienced a clinically significant AE attributable to deutetrabenazine, the investigator determined if a dose reduction or suspension was necessary. Subjects had a telephone contact at Week 1 and a clinic visit at Week 2, to evaluate safety and establish a dose of study drug that adequately controlled dyskinesia and was well tolerated. Although subjects entered the long-term treatment period after Week 2, titration continued through Week 6 to optimize dose.

Long-Term Treatment Period (up to 52 weeks). During long-term treatment, subjects will continue titration through Week 6. During this period, all subjects will be contacted by telephone at Week 3 (the first week of the Long-Term Treatment Period) and Week 5 and will return to the clinic at Weeks 4, 6, 15, 28, 41, and 54 for evaluation of safety and dyskinesia control. Subjects who have not achieved a dose level that adequately controls dyskinesia and is well tolerated by the Week 6 visit should have unscheduled visits or telephone contacts to further adjust their dose upward or downward. Interactions with the clinical site for dose adjustment should alternate between telephone contacts and clinic visits. During long-term treatment, further dose adjustments of deutetrabenazine may be made, if necessary, but not more often than weekly and only in increments of 6 mg per day. Dose adjustments should be based on all available information, including the subject's and caregiver's (if appropriate) reports of AEs and dyskinesia control, as well as information from rating scales and safety evaluations, when available.

Post-Treatment Safety Follow Up. All subjects will discontinue study drug at the Week 54 visit and return for their final clinic visit at Week 55 for evaluation of safety, dyskinesia control, and motor function. During this 1-week washout period, subjects should not take prohibited concomitant medications. Subjects will also have a follow-up telephone contact at Week 58, four weeks after their last dose of study drug, to evaluate AEs and concomitant medication usage.

Safety Endpoints. Safety and tolerability will be assessed throughout the study by monitoring the following parameters: adverse events (AEs), clinical laboratory tests, physical examination, vital signs, 12-lead ECGs, Unified Parkinson's Disease Rating Scale (UPDRS) Part III (motor examination), Barnes Akathisia Rating Scale (BARS), Hospital Anxiety and Depression Scale (HADS), Columbia Suicide Severity Rating Scale (C-SSRS), Epworth Sleepiness Scale (ESS), and Montreal Cognitive Assessment (MoCA©).

Efficacy Endpoints. The following measures were or will be used to assess efficacy: change in Abnormal Involuntary Movement Scale (AIMS) score (items 1 through 7) from baseline to end of long-term therapy (Week 54) as assessed by blinded central video rating; proportion of subjects who are a treatment success at the end of long-term therapy (Week 54), based on the Clinical Global Impression of Change (CGIC) (in which a treatment success is defined as Much or Very Much Improved); change in the modified Craniocervical Dystonia (CDQ-24) score from baseline of this study to the end of long-term therapy (Week 54); proportion of subjects who have a 50% or greater reduction in AIMS score from baseline of this study to the end of long term therapy (Week 54); proportion of subjects who are a treatment success at the end of long-term therapy (Week 54), based on the Patient Global Impression of Change (PGIC) (in which a treatment success is defined as Much or Very Much Improved); percent change in AIMS score from Baseline of this study to the end of long term therapy (Week 54); and based on the change in AIMS score from baseline of this study to the end of long-term therapy (Week 54), as assessed by blinded central video rating, the cumulative proportion of responders ranging from a 10% improvement from baseline to a 90% improvement from baseline in steps of 10 percentage points.

Figure 9:
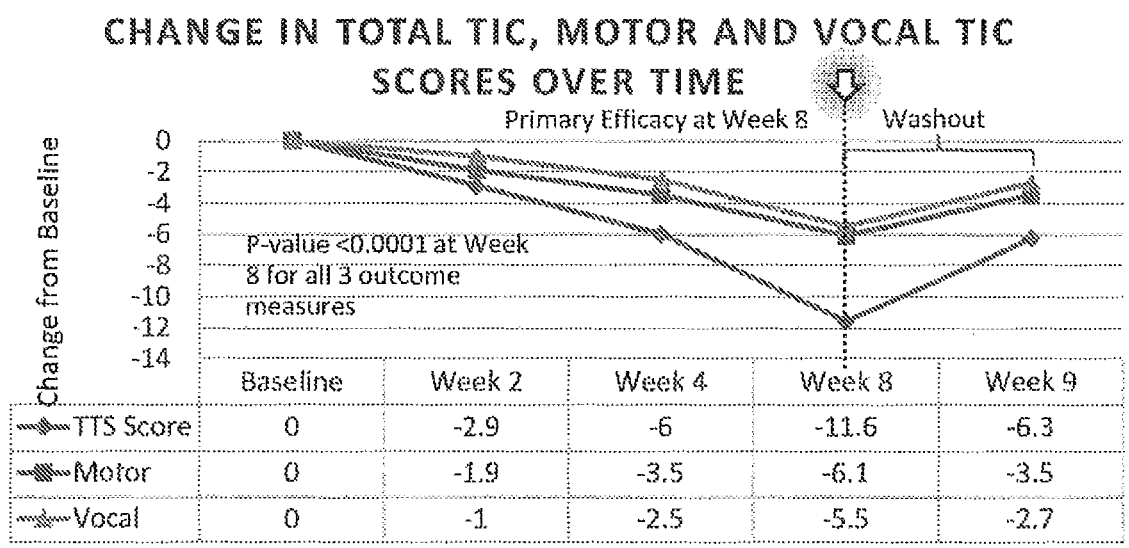
FIG. 9 shows the mean change in motor, vocal, and combined total tic scores in subjects treated in the pilot Tourette Syndrome study, from baseline through the end of treatment at week 8 and washout at week 9. The top line (triangles) represents the vocal tic score; the middle line represents motor (squares) tic score, and the bottom line (diamonds) represents the total (combined motor and vocal) tic score. Treatment with deutetrabenazine lowered (improved) both motor and vocal tics.
Figure 10:
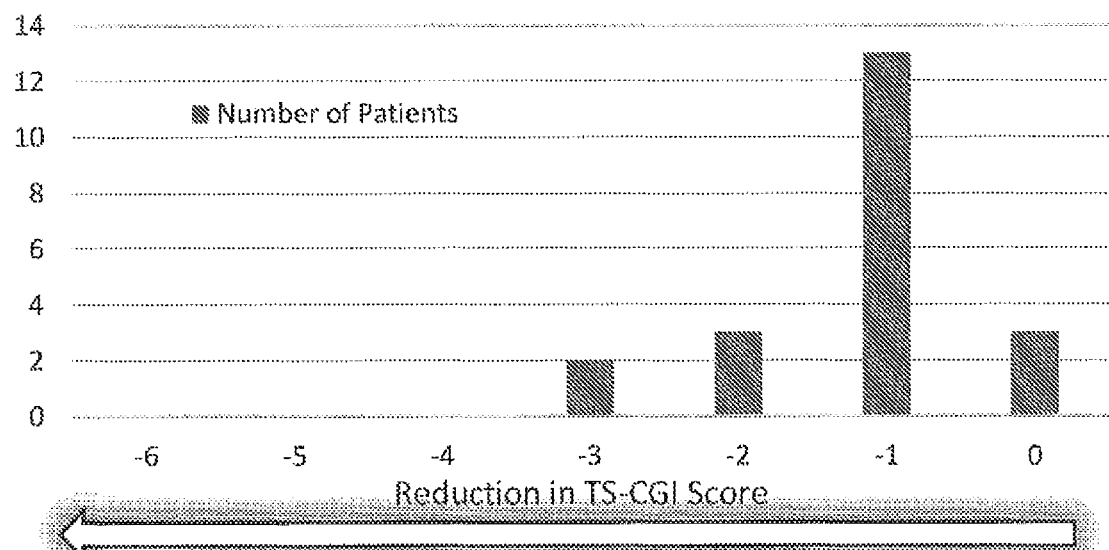
FIG. 10 shows the change in the Tourette Syndrome Clinical Global Impression in subjects treated in the pilot Tourette Syndrome study, from baseline through week 8; improvement is measured by reduction in TS-CGI score.
Figure 11:
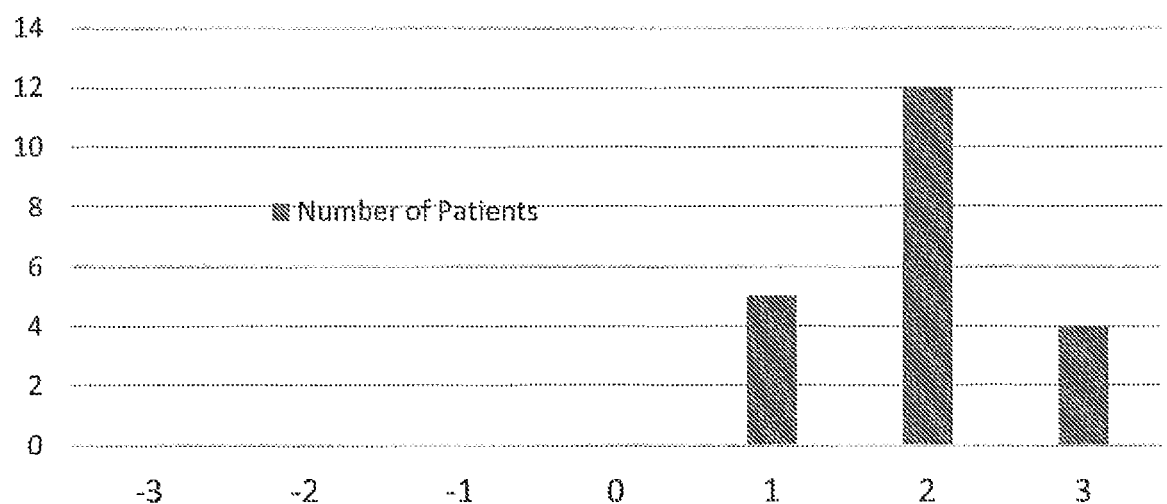
FIG. 11 shows the Tourette Syndrome Patient Global Impression of Change in subjects treated in the pilot Tourette Syndrome study, at week 8; improvement is measured by positive increase in TS-PGIC score wherein, e.g., 1 indicates minimally improved; 2, much improved; and 3, very much improved.

Results. Results are given in FIG. 9, which shows that by Week 6 of the study, over 50% of subjects were much or very much improved according to PGIC and CGIC.

ARM-TD

An additional clinical study, Aim to Reduce Movements in Tardive Dyskinesia (ARM-TD) was designed and conducted to evaluate the efficacy of SD-809 (deutetrabenazine) in the treatment of moderate to severe tardive dyskinesia. The ARM-TD study was a 1:1 randomized, double-blind, placebo-controlled, parallel-group study of 117 patients globally (with 104 patients completing the trial) with moderate to severe tardive dyskinesia.

Subjects were screened for inclusion in the study as follows. Inclusion criteria included: between 18 and 75 years of age, inclusive; history of using a dopamine receptor antagonist for at least 3 months (or 1 month in subjects 60 years of age and older); clinical diagnosis of TD, and has had symptoms for at least 3 months prior to Screening; TD symptoms are bothersome to the subject or cause functional impairment; at Screening and Baseline visits, the subject has moderate or severe abnormal movements as judged by the Investigator based on Item 8 of the AIMS and a total motor AIMS score of ≥6 (based on Items 1 through 7) as assessed by the Principal Investigator; for subjects with underlying psychiatric illness, subject is psychiatrically stable and has had no change in psychoactive medications (including, but not limited to neuroleptics, benzodiazepines, anticonvulsants, and mood stabilizers) for ≥30 days before Screening (45 days for antidepressants); subjects on long-acting (depot) medications have been on stable therapy (dose, frequency) for ≥3 months before Screening; and subject has a mental health provider who is aware of the subject's participation in the trial, and does not anticipate any changes to the subject's treatment regimen (drug, dose, frequency) in the next 3 months; history of being compliant with prescribed medications; able to swallow study drug whole; written, informed consent; subject has good general health, lives in a stable environment, is expected to complete all study assessments, and has adequate supervision when necessary to comply with all study procedures, attend all study visits and safely participate in the trial; sufficient reading skills to comprehend the subject-completed rating scales; and, if female and of childbearing potential, agree to use acceptable methods of contraception from Screening through study completion if sexually active.

Exclusion criteria included: score ≥11 on the depression subscale of the Hospital Anxiety and Depression Scale (HADS) at Screening or Baseline; developmentally disabled or has evidence of dementia; unstable or serious medical illness at Screening or Baseline; history (within 3 months) or presence of violent behavior; QTcF value >450 ms (males) or >460 ms (females), or >480 ms (with right bundle branch block [RBBB]) on 12-lead ECG at Screening; evidence of hepatic impairment at Screening, as indicated by: AST or ALT >2.5 times the upper limit of normal (ULN), or ALP or total bilirubin >2 times the ULN (wherein abnormalities in two or more of these AST, ALT, ALP, TBil must be approved by the Medical Monitor to be enrolled, but subjects with Gilbert's Syndrome eligible if approved by the Medical Monitor), or Prothrombin time >4 seconds prolonged, or positive HBsAg; evidence of significant renal impairment at Screening, indicated by a creatinine clearance <50 mL/min, as estimated by the Cockroft-Gault formula; known allergy to tetrabenazine or to any of the components of deutetrabenazine; subject has participated in an investigational drug or device trial and received study drug within 30 days (or 5 drug half-lives) of Screening, whichever is longer; pregnant or breast-feeding at Screening or Baseline; acknowledged present use of illicit drugs at Screening; history of alcohol or substance abuse in the previous 12 months, as defined in the DSM-V, or subject is unable to refrain from substance abuse throughout the study; and positive urine drug screen (for amphetamines, barbiturates, benzodiazepine, phencyclidine, cocaine, or opiates) at Screening or Baseline, except if subject is receiving a stable dose of a benzodiazepine.

Dosing. Enrolled patients received either deutetrabenazine or placebo, which was titrated from a starting dose of 6 mg of deutetrabenazine (which, as in previous studies, provides an AUC of total $(\alpha+\beta)$-HTBZ that is comparable to 12.5 mg of tetrabenazine) to optimal dosage between 12 and 48 mg/day over the course of six weeks, in increments of 6 mg/day per week. Drug was then administered at that dose for another six weeks for a total treatment of 12 weeks, followed by a 1-week washout period. Randomization to each group was 1:1 and was stratified by baseline use of dopamine receptor antagonists (currently taking versus not). Deutetrabenazine tablets or placebo, were supplied as 6, 9, 12, 15, and 18 mg tablets and administered BID with meals in the morning and evening (recommended 10 hours apart; minimum 6 hours apart). Dose suspensions of up to one week were permitted if the subject experienced a clinically significant adverse event.

Study Objectives and Endpoints. The objectives of the study was to evaluate the efficacy of SD-809 in reducing the severity of abnormal involuntary movements associated with tardive dyskinesia and the safety and tolerability of titration and maintenance therapy with deutetrabenazine in subjects with drug-induced tardive dyskinesia. The primary efficacy endpoint is the change in AIMS score (Items 1 through 7) from baseline to Week 12, as assessed by blinded central video rating. Baseline AIMS score is defined for each subject as the Day 0 assessment. The AIMS is composed of 12 clinician-administered and scored items. Items 1-10 are rated on a 5-point, anchored scale and consist of the following:

Items 1-4 assess orofacial movements;
Items 5-7 deal with extremity and truncal dyskinesia;
Items 8-10 deal with global severity as judged by the examiner, and the patient's awareness of the movements and the distress associated with them; and
Items 11-12 are yes/no questions concerning problems associated with teeth and/or dentures, as such problems can be mistaken for dyskinesia.

A total score from items 1 through 7 (orofacial, extremity and truncal movements) can be calculated and represent observed movements, with higher scores indicative of more severe dyskinesia. Item 8 can be used as an overall severity index; items 9 and 10 provide additional information with regard to patient incapacitation and awareness; and items 11 and 12 provide information that may be useful in determining lip, jaw, and tongue movements.

The key secondary endpoints are: 1) the proportion of subjects who are a treatment success at Week 12, based on the Clinical Global Impression of Change (CGIC); 2) the proportion of subjects who are a treatment success at Week 12, based on the Patient Global Impression of Change (PGIC); and 3) the change in the modified Craniocervical Dystonia Questionnaire (CDQ-24) from baseline to Week 12. As with previous studies, PGIC/CGIC treatment success may be defined as Much or Very Much Improved on a 7-point Likert Scale, ranging from very much worse to very much improved at Week 12. The CDQ-24 is a disease-specific quality of life questionnaire developed for use in patients with craniocervical dystonia, including both cervical dystonia (CD) and blepharospasm (BPS). The CDQ-24 was selected for use in the present study because it includes domains which are relevant not only to CD and BPS, but to TD, such as stigma, emotional well-being, pain, activities of daily living, and social/family life. For the present study, the CDQ-24 has been modified such that the questions focus more directly on the impact of TD (as opposed to CD/BPS) on quality of life.

Additional secondary endpoints included 1) the percent change in AIMS score (central rating) from baseline to Week 12; 2) based on the change in AIMS score (central rating) from baseline to Week 12, the cumulative proportion of responders for responder levels ranging from a 10% improvement from baseline to a 90% improvement from baseline in steps of 10 percentage points; and 3) Change in AIMS score (Items 1 through 7) from baseline to Week 12, as assessed by the local rater, wherein baseline AIMS score is defined for each subject as the Day 0 assessment.

Finally, at each clinical site, an Investigator experienced in assessing movement disorders, was responsible for confirming the diagnosis of TD, performing all clinical assessments, and making decisions about adjusting the dose of study drug. Safety was also monitored via adverse events reporting and other measures, including but not limited to the UPDRS, BARS, HADS, C-SSRS, ESS, and MoCA.

Measurements and Statistics. Digital video recordings of AIMS assessments made at all clinic visits (at Screening, Baseline, Weeks 2, 4, 6, 9, and 12) were rated by pairs of central raters who were experts in movement disorders and were blinded to treatment arm, sequence of video, and the investigator AIMS score. Analysis was carried out using a linear mixed model for repeated measurements (MMRM) with the change in the AIMS score as the dependent variable. The model included fixed effects for treatment group, time point (five levels: Weeks 2, 4, 6, 9, and 12), the treatment group by time point interaction, and the randomization stratification variable. The unstructured covariance model was used and the primary analysis compared the deutetrabenazine and placebo groups at Week 12 using a two-sided test at the 5% level of significance.

Efficacy Results. Top-line data showed that the study met its primary endpoint. Patients taking deutetrabenazine achieved an improvement of 3.0 points on the AIMS score from baseline to end of therapy compared to 1.6 points in placebo (p=0.0188) for a clinically meaningful effect. Additionally, secondary endpoints numerically favored deutetrabenazine. Results are given in Table 22,

TABLE 22

| | DTBZ (N = 56) | Placebo (N = 57) | Treatment Difference |
|---|---|---|---|
| AIMS Change (LS Mean) | −3 | −1.6 | −1.4 (p-value 0.0188) |
| PGIC Treatment Success N (%) | 42.90% | 29.80% | 13.00% |
| CGIC Treatment Success (%) | 48.20% | 40.40% | 7.90% |
| Change from baseline mCDQ-24* | −11.1 | −8.3 | −2.7 |

Safety Results. The study also showed a favorable safety and tolerability profile for deutetrabenazine, including low rates of depression, somnolence, insomnia and akathisia. Fewer patients taking deutetrabenazine than placebo experienced serious adverse events (SAEs) (4 patients [6.9%] in deutetrabenazine versus 6 [10.2%] in placebo; none of the SAEs were treatment related) or experienced adverse events leading to discontinuation (1 patient [1.7%] versus 2 patients [3.4%]). Neuropsychiatric adverse events in this patient population were infrequently associated with SD-809 treatment compared to placebo, and included somnolence/sedation (9 [15.5%] versus 6 [10.2%]), insomnia (4 [6.9%] versus 1 [1.7%]), akathisia (3 [5.2%] versus 0 [0.0%]) (Depression/depressed mood was reported by one patient in each treatment group, and suicidal ideation was reported by one patient in the placebo group versus none in the SD-809 group. Three patients discontinued from the study for adverse events (1 in deutetrabenazine group vs. 2 in placebo group). For all other side effects reported in the study, rates in the deutetrabenazine group were similar or lower than the placebo group. Results are shown below in Table 23, which includes adverse events observed in 3 or more subjects.

TABLE 23

| | | DTBZ (n = 58) | Placebo (n = 59) |
|---|---|---|---|
| Any TEAEs (Treatment-Emergent Adverse Events) | | 41 (70.7%) | 36 (61.0%) |
| Serious TEAEs | | 4 (6.9%) | 6 (10.2%) |
| TEAEs Resulting in Study Withdrawal | | 1 (1.7%) | 2 (3.4%) |
| Nervous system disorders | Somnolence/sedation | 9 (15.5%) | 6 (10.2%) |
| | Headache | 4 (6.9%) | 6 (10.2%) |
| | Dizziness | 2 (3.4%) | 3 (5.1%) |
| | Akathisia | 3 (5.2%) | 0 (0.0%) |
| Psychiatric disorders | Anxiety | 3 (5.2%) | 4 (6.8%) |
| | Insomnia | 4 (6.9%) | 1 (1.7%) |
| Gastrointestinal disorders | Dry mouth | 2 (3.4%) | 6 (10.2%) |
| | Diarrhea | 3 (5.2%) | 3 (5.1%) |
| | Constipation | 2 (3.4%) | 2 (3.4%) |
| | Nausea | 2 (3.4%) | 2 (3.4%) |
| | Vomiting | 1 (1.7%) | 3 (5.1%) |
| General disorders | Fatigue | 4 (6.9%) | 5 (8.5%) |
| | Chest pain | 1 (1.7%) | 2 (3.4%) |
| Infections and infestations | Upper respiratory tract infection | 2 (3.4%) | 4 (6.8%) |
| | Nasopharyngitis | 2 (3.4%) | 1 (1.7%) |
| | Pneumonia | 1 (1.7%) | 2 (3.4%) |

Based on the studies disclosed herein, it is expected that deutetrabenazine, other deuterium substituted tetrabenazines and valbenazine will be efficacious in the treatment of tardive dyskinesia and other movement disorders and symptoms, such as dyskinesias generally, dystonia, ballismus, akinesia, and parkinsonism, and that the dosing regimens and methods disclosed herein will yield significant patient benefits.

Tourette Syndrome

Tourette syndrome (TS) is a neurological disorder characterized by repetitive, stereotyped, involuntary movements and vocalizations called tics, which per DSM-V criteria first presents in childhood, before 18 years of age. Several studies have been or could be used to demonstrate the efficacy and tolerability of deutetrabenazine in the reduction of symptoms associated with TS, including motor and phonic tics.

Open-Label Pilot Study of Safety and Efficacy in TS Patients

An open-label, pilot study was undertaken 1) to evaluate the safety and tolerability of treatment with deutetrabenazine, and 2) to evaluate the efficacy of deutetrabenazine to suppress the motor and phonic tics of TS.

Study Design. Inclusion criteria (at screening, unless otherwise indicated) included: 12 to 18 years of age, inclusive; DSM-V diagnosis of TS and has manifested motor and phonic tics within 3 months before screening; total tic score of 19 or higher on the YGTSS; TS-CGI score of 4 or higher (consistent with moderately ill); tic severity and frequency has been stable for at least 2 weeks; able to swallow study medication whole; willing to adhere to medication regimen and to comply with all procedures; in good general health, as indicated by medical and psychiatric history as well as physical and neurological examination; written, informed consent (subject and parent/guardian); and female subjects of childbearing potential agree to use an acceptable method of contraception through study completion, including abstinence, IUD or intrauterine system in place for at least 3 months prior; subject or partner using barrier method (e.g., condom, diaphragm, or cervical cap) with spermicide; partner has a documented vasectomy >6 months prior to enrollment; stable hormonal contraception (with approved oral, transdermal, or depot regimen) for at least 3 months prior.

Exclusion criteria (at screening or baseline, unless otherwise indicated) included: serious untreated or undertreated psychiatric illness, such as depression, schizophrenia, or bipolar disorder (but subjects receiving antidepressant therapy may be enrolled if on a stable dose for at least 8 weeks before); history of suicidal thoughts or behavior, including previous intent to act on suicidal ideation with a specific plan (positive answer to question 5 on the Columbia Suicide Severity Rating Scale [C-SSRS] irrespective of level of ambivalence at the time of suicidal thought, previous preparatory acts or behavior, or previous actual, interrupted, or aborted suicide attempt; subject has received any of the following concomitant medications within 14 days prior to screening or baseline: tetrabenazine, neuroleptics (oral or depot, typical and atypical; depot \within 3 months of screening), guanfacine or clonidine (within 7 days of screening or baseline), benzodiazepines such as clonazepam, topiramate, metoclopramide, monoamine oxidase inhibitors (MAOIs), levodopa or dopamine agonists, reserpine (within 21 days of screening or baseline), botulinum toxin (within 3 months of screening or baseline); subject is being treated with deep brain stimulation for control of tics; below-average intelligence or mental abilities, in the opinion of the Investigator; progressive or degenerative neurological disorder or a structural disorder of the brain; subject receiving more than one agent for the treatment of each co-morbid behavioral symptom; subject requires treatment with drugs known to prolong the QT interval (but citalopram and escitalopram allowed when administered according to approved labeling); QTcF value >440 ms on 12-lead electrocardiogram (ECG); known allergy to any of the components of study medication; participation in an investigational drug or device trial within 30 days (or 5 drug half-lives) of screening, whichever is longer; pregnant or breast-feeding; present use of illicit drugs; and history of alcohol or substance abuse in the previous 12 months, as defined in the DSM-V, or unable to refrain from substance abuse throughout the study.

Subjects completing the trial received treatment with study drug for a total of 8 weeks and had safety follow-up 4 weeks after treatment. Throughout the study, an independent rater assessed tic severity with the Yale Global Tic Severity Scale (YGTSS) and tic impact with the TS-Clinical Global Impression (TS-CGI) scale. The independent rater will not have knowledge of the subject's clinical care, including medications or reports of adverse events (AEs).

Dose regimen. Study drug was available in five dose strengths: 6, 9, 12, 15, and 18 mg, all of which were identical in size, shape, and color (white). Subjects who qualified for the study were assigned to treatment with deutetrabenazine and were titrated over 6 weeks to a dose level of study drug that adequately suppressed tics and was well tolerated (i.e., optimal dose). Subjects then maintained that dose level for the duration of the treatment period. Subjects who were receiving CBIT (Comprehensive Behavioral Intervention for Tics) therapy were permitted to participate as long as therapy had been stable/ongoing for at least 4 weeks before Screening and was expected to be stable for the duration of the trial. Study drug was dosed as follows. All treatment doses were administered with meals. A daily dose of 6 mg was given once a day in the morning, and daily doses of 12 mg and higher were administered twice daily in divided doses, approximately 10 hours apart during the day. The starting dose was deutetrabenazine 6 mg in the AM. The dose of study drug was optionally adjusted weekly in increments of 6 mg/day during the titration period to identify a dose level that suppressed tics and was well tolerated. Dose reductions were in increments of 6 mg/day. In this study, the maximum total daily dose of deutetrabenazine at the Week 5 visit or later was 36 mg (18 mg twice daily [BID]).

Screening/Baseline visit. After informed consent/written assent was obtained, subjects who met selection criteria had a comprehensive evaluation including physical and neurological examination. Subjects then underwent a baseline assessment of tic severity (performed by an independent rater) and co-morbid illnesses. Following this evaluation, subjects continuing to meet selection criteria were provided with deutetrabenazine and were instructed to start treatment on Day 1, the day after the baseline visit.

Titration period (6 weeks). Subjects and their parent/guardian interacted weekly with the clinical research staff, either by telephone contact or clinic visit, through the sixth week of the titration period, in order to evaluate safety and establish a dose of deutetrabenazine that adequately suppressed tics and was well tolerated. Safety evaluations during titration included assessment of vital signs, monitoring for adverse events, and rating scales for depression and suicidal ideation and behavior. In-person study visits were scheduled at Weeks 2 and 4 after initiating therapy and telephone contacts were scheduled for Weeks 1, 3, 5, and 6 after initiating therapy in order to assess tic suppression and adverse events. The YGTSS and TS-CGI were assessed by an independent rater. The Investigator, in consultation with the subject and parent/guardian, determined when an adequate level of tic suppression had been achieved. The dose of deutetrabenazine was increased on a weekly basis until there was adequate suppression of tics, the subject experienced a protocol-defined "clinically significant" AE (defined as an AE that is related to study medication and either (1) moderate or severe in intensity or (2) meets the criteria for a serious adverse event [SAE]), or the maximal allowable dose was reached. Although dose adjustments could made up to and including the Week 5 phone call, if a stable dose was reached before then, the subject continued on that dose for the remainder of the titration period and throughout maintenance dosing. Once adequate suppression of tics had been achieved, the dose of study drug was not increased further. If a subject experienced a "clinically significant" AE that was attributed to study drug, the Investigator used his or her judgment to determine if a dose reduction or suspension was necessary. Dose adjustments were to be made based on all available information, including the subject and parent/guardian reports of AEs and tic suppression, the clinical assessment of safety and efficacy by the Investigator, as well as information from rating scales. At the end of the titration period, the subject's dose was established for the maintenance period.

Maintenance period (2 weeks). Subjects continued to receive their maintenance dose over the next 2 weeks, although dose reductions for AEs were allowed. Subjects returned to the clinic at Week 8 for a complete evaluation, including physical and neurological examination and performance of all rating scales, including the YGTSS and TS-CGI, which were assessed by an independent rater. Subjects discontinued study drug at the Week 8 visit.

Follow-up (4 weeks). Subjects returned 1 week after the Week 8 visit for evaluation of safety and tic suppression. Subjects also had a follow-up telephone contact 4 weeks after their last dose of study drug. Subjects who completed the study were potentially eligible to participate in a long-term safety study if such a study were conducted.

Pharmacokinetics. A PK substudy was conducted to evaluate the PK of deutetrabenazine and its metabolites in up to 9 of the 21 enrolled subjects. Subjects in the PK substudy underwent sequential PK blood sampling over the course of 6 hours postdose at the Week 8 visit. For the subjects not participating in the PK substudy, a single PK sample was obtained at Week 8 at the time of the blood draw for clinical laboratory tests.

Safety Endpoints. Safety and tolerability were assessed throughout the study by monitoring the following parameters: adverse events (AEs), clinical laboratory tests, physical examination, vital signs, 12-lead ECGs, Columbia Suicide Severity Rating Scale (C-SSRS), Beck Depression Inventory, Second Version (BDI-II), and the Children's Yale-Brown Obsessive-Compulsive Scale (CY-BOCS).

Efficacy Endpoints. The following measures were used to assess efficacy: Yale Global Tic Severity Scale (YGTSS), Total Tic Severity Score (TTS) of the YGTSS, Global Severity Score (GSS) of the YGTSS, Tourette Syndrome Clinical Global Impression (TS-CGI), and Tourette Syndrome Patient Global Impression of Change (TS-PGIC).

Results. Initial results indicate that deutetrabenazine is efficacious in the treatment of tics associated with Tourette syndrome. A consistent trend of improvement was observed in motor, vocal, total tic severity, and Yale global total tic severity from baseline through the end of the eight-week treatment phase. This culminated in a mean change of −10.4 units in total tic severity. Additionally, discontinuation in treatment after week 8 led to a slight increase in tics. Results are given below in Table 24; ND indicates no data.

TABLE 24

| Visit | | Overall (N = 23) | | | | |
|---|---|---|---|---|---|---|
| | | MTSS | VTSS | TTS | Impairment | GSS |
| B* | n | 23 | 23 | 23 | 23 | 23 |
| | Mean | 17.4 | 14.2 | 31.6 | 34.3 | 66.0 |
| | (SD) | (3.95) | (5.66) | (7.92) | (9.45) | (15.99) |
| | Median | 18 | 15 | 31 | 30 | 68 |
| | Min, Max | 10, 24 | 0, 22 | 19, 46 | 20, 50 | 39, 96 |
| Wk 2 | n | 21 | 21 | 21 | ND | 21 |
| | Mean | 15.9 | 13.5 | 29.4 | ND | 59.4 |
| | (SD) | (5.06) | (5.64) | (9.81) | | (19.45) |
| | Median | 16 | 14 | 28 | ND | 57 |
| | Min, Max | 0, 24 | 4, 22 | 4, 46 | ND | 4, 96 |
| Δ B-Wk 2 | n | 21 | 21 | 21 | ND | 21 |
| | Mean | −1.9 | −1.0 | −2.9 | ND | −7.7 |
| | (SD) | (2.67) | (3.29) | (5.37) | | (12.25) |
| | Median | 0 | 0 | 0 | ND | 0 |
| | Min, Max | −10, 0 | −11, 4 | −21, 4 | ND | −41, 12 |
| Wk 4 | n | 21 | 21 | 21 | ND | 21 |
| | Mean | 14.2 | 12.1 | 26.3 | ND | 51.1 |
| | (SD) | (6.30) | (6.60) | (11.91) | | (22.64) |
| | Median | 14 | 12 | 27 | ND | 51 |
| | Min, Max | 0, 25 | 0, 25 | 0, 50 | ND | 0, 100 |
| Δ B-Wk 24 | n | 21 | 21 | 21 | ND | 21 |
| | Mean | −3.5 | −2.5 | −6.0 | ND | −16.0 |
| | (SD) | (4.32) | (4.55) | (8.18) | | (18.84) |
| | Median | −2 | 0 | −3 | ND | −12 |
| | Min, Max | −15, 2 | −12, 4 | −25, 4 | ND | −55, 4 |
| Wk 8 | n | 23 | 23 | 23 | 21 | 23 |
| | Mean | 12.0 | 9.2 | 21.2 | 22.9 | 45.1 |
| | (SD) | (5.35) | (6.64) | (10.95) | (11.46) | (21.71) |
| | Median | 11 | 9 | 23 | 20 | 47 |
| | Min, Max | 0, 24 | 0, 24 | 0, 48 | 0-50 | 0, 98 |
| Δ B-Wk 28 | n | 23 | 23 | 23 | 21 | 23 |
| | Mean | −5.3 | −5.0 | −10.4 | −11.9 | −20.8 |
| | (SD) | (4.98) | (4.41) | (8.83) | (9.28) | (17.61) |
| | Median | −4 | −4 | −10 | −10 | −16 |
| | Min, Max | −15, 6 | −14, 2 | −25, 5 | −30-0 | −50, 15 |
| Wk 9 | n | 18 | 18 | 18 | ND | 18 |
| | Mean | 13.9 | 11.7 | 25.6 | ND | 51.7 |
| | (SD) | (4.94) | (7.30) | (11.06) | | (22.98) |
| | Median | 14.5 | 10.5 | 26 | ND | 51 |
| | Min, Max | 5, 25 | 0, 25 | 10, 50 | ND | 14, 100 |
| Δ B-Wk 9 | n | 18 | 18 | 18 | ND | 18 |
| | Mean | −3.4 | −2.9 | −6.3 | ND | −14.7 |
| | (SD) | (3.15) | (3.80) | (6.49) | | (15.50) |
| | Median | −3 | −2.5 | −5 | ND | −10.5 |
| | Min, Max | −11, 1 | −11, 3 | −22, 4 | ND | −45, 4 |

*B = baseline;
Wk = week

Additionally, preliminary results indicate improvements in several other relevant measures. In PGIC, a mean improvement of 1.8 points was observed (on the 7-point scale above where 1=minimally improved, 2=much improved, 3=very much improved), suggesting patients are generally improved after 8 weeks of treatment (about 75% much or very much improved). In TS-CGI, mean improvement from a baseline of 4.7 to 3.7 at Week 8 was observed (on a 7 point scale where lower is better). Finally, the adverse event profile appeared generally consistent with previous studies.

It is expected that deutetrabenazine, other deuterium substituted tetrabenazines and valbenazine will be efficacious in the treatment of Tourette syndrome and other movement disorders and symptoms, such as tics, stereotypy, akathisia, dyskinesia, and restless legs syndrome, and that the dosing regimens and methods disclosed herein will yield significant patient benefits.

Twelve-Week Randomized Phase 2/3 Study of Safety and Efficacy in TS Patients

Purpose. The primary objective of this study is to evaluate the efficacy of deutetrabenazine to reduce motor and phonic tics associated with TS; the secondary objective of this study is to evaluate the safety and tolerability of titration and maintenance therapy with deutetrabenazine.

Study Design. This is a Phase 2/3, randomized, double-blind, placebo-controlled, parallel group study in which patients with tics associated with TS will be invited to participate. The study will include male and female patients between 6 and 16 years of age (inclusive) with a tic associated with Tourette syndrome (TS). Patients will be randomized and stratified by age at baseline [6 to 11 years, 12 to 16 years]). The dose of study drug for each patient will be titrated to an optimal level followed by maintenance therapy at that dose. The overall treatment period will be 12 weeks in duration. The titration period will be 7 weeks, and the maintenance period will be 5 weeks, which will be followed by a washout period of 1 week. Patients Inclusion criteria. Patients may be enrolled in the study if they meet all of the following criteria: 6 to 16 years of age, inclusive, at baseline; weight of at least 44 pounds (20 kg) at baseline; meets the Diagnostic and Statistical Manual of Mental Disorders, Fifth Edition (DSM-V) diagnostic criteria for TS and, in the opinion of the investigator, patient, and caregiver/adult, the patient's active tics are causing distress or impairment; TTS of 20 or higher on the YGTSS at screening and baseline; able to swallow study medication whole; patient and caregiver/adult are willing to adhere to the medication regimen and to comply with all study procedures; good general health, as indicated by medical and psychiatric history as well as physical and neurological examination; ability to understand the nature of the study and its procedures, and expected to complete the study as designed (in investigator's opinion); written informed consent; women/girls of childbearing potential (not surgically sterile (≥3 months)—via tubal ligation, hysterectomy, oophorectomy—or congenitally sterile) whose male partners are of childbearing potential must use contraception for the duration of the study and for 30 days after discontinuation of study drug (acceptable methods of contraception are those with a failure rate of less than 1% per year, e.g., IUD, oral, implanted, transdermal, or injected hormonal contraceptive, barrier method with spermicide, and partner vasectomy.

Exclusion Criteria. Patients will not be enrolled in this study if they meet any of the following criteria: neurologic disorder other than TS that could obscure the evaluation of tics; patient's predominant movement disorder is stereotypy (coordinated movements that repeat continually and identically) associated with Autism Spectrum Disorder; confirmed diagnosis of bipolar disorder, schizophrenia, or another psychotic disorder; clinically significant depression at screening or baseline (but patients receiving antidepressant therapy may be enrolled if on a stable dose for at least 6 weeks before screening (see list below for prohibited antidepressants); history of suicidal intent or related behaviors within 2 years of screening: previous intent to act on suicidal ideation with a specific plan, irrespective of level of ambivalence, at the time of suicidal thought; previous suicidal preparatory acts or behavior; history of a previous actual, interrupted, or aborted suicide attempt; a first-degree relative who has completed suicide; clinically significant OCD at baseline that, in the opinion of the investigator, is the primary cause of impairment; patient has received CBIT for TS or CBT for OCD within 4 weeks of screening; patient has received any of the following concomitant medications for tics within the specified exclusionary windows of screening:

Within 3 months: depot neuroleptics, botulinum toxin, or tetrabenazine;
Within 21 days: reserpine;
Within 14 days: monoamine oxidase inhibitors, neuroleptics (oral), typical and atypical antipsychotics, metoclopramide, levodopa, and dopamine agonists (note: use of benzodiazepines is allowed if primary use is not for tics and dosing has been stable for at least 4 weeks before screening; use of topiramate (up to 200 mg/day) is allowed if dosing has been stable for at least 4 weeks before screening; and use of guanfacine or clonidine is allowed if dosing has been stable for at least 4 weeks before screening);
treatment with deep brain stimulation, or transmagnetic stimulation or transcranial direct current stimulation for reduction of tics within 4 weeks of the screening visit; an unstable or serious medical illness at screening or baseline; patient requires treatment with drugs known to prolong the QT interval (list below); QTcF interval value >440 msec on 12-lead ECG at screening; evidence of hepatic impairment (as indicated by AST or ALT >2.5×the upper limit of the normal range (ULN) at screening or ALP or total bilirubin (Tbil) >2×ULN at screening, though patients with Gilbert's Syndrome and patients with abnormalities in 2 or more of AST, ALT, ALP, and Tbil are eligible to participate if approved by the medical monitor; evidence of clinically significant renal impairment, indicated by a serum creatinine >1.5×ULN at screening; known allergy to any of the components of the study drug product; patient has participated in an investigational drug or device trial and received study drug/intervention within 30 days or 5 drug half-lives of baseline, whichever is longer; pregnant or breastfeeding; history of or acknowledged alcohol or substance abuse in the previous 12 months, as defined in the DSM-V; positive urine drug screen test result or is unable to refrain from substance abuse throughout the study; and a DSM-V diagnosis based on the MINI Kid Inventory modules performed at screening that, in the opinion of the investigator, makes the patient unsuitable for the study.

Prohibited drugs include: azithromycin, chloroquine/Mefloquine, clarithromycina, domperidone, droperidol, erythromycina, moxifloxacin, sevoflurane, probucol, sparfloxacin, chlorpromazine, aripiprazole, haloperidol, asenapine maleate, loxapine, clozapine, molindone, iloperidone, perphenazine, lurasidone, pimozide, olanzapine, prochlorperazine, olanzapine/fluoxetine, thioridazine paliperidone, thiothixene, quetiapine, trifluoperazine, risperidone, promethazine-containing compounds, ziprasidone, and tiapride.

Efficacy Endpoints. The study's primary efficacy endpoint will be the change in the Total Tic Score (TTS) of the Yale Global Tic Severity Scale (YGTSS) from baseline to week 12, with a goal of reducing motor and phonic/vocal tics. Secondary efficacy endpoints will be changes in the Tourette Syndrome-Clinical Global Impression (TS-CGI) score, Tourette Syndrome-Patient Global Impression of Severity (TS-PGIS) score, and the Gilles de la Tourette Syndrome-Quality of Life (GTS-QOL) physical/activities of daily living (ADL) subscale, all from baseline to week 12.

Safety Endpoints. Safety endpoints will be: incidence of adverse events; observed values and changes from baseline in vital signs; observed values and change from baseline in the Children's Depression Inventory 2 (CDI-2; Parent and Self-report versions); observed values in the children's Columbia Suicide Severity Rating Scale (C-SSRS); observed values in electrocardiogram (ECG) parameters and shifts from screening for clinically significant abnormal findings; and observed values and changes from screening in clinical laboratory parameters (hematology, chemistry, and urinalysis).

Titration Period (7 weeks). Patients who remain eligible for participation in the study will be randomized at the baseline visit (day 1) and that evening (ie, after the study visit) will receive 6 mg of blinded study drug with food.

The dose of the study drug will be increased until 1) there is optimal reduction of tics, as determined by the investigator, in consultation with the patient and caregiver/adult; 2) the dose is not tolerable.

Maintenance Period. At the end of the titration period, the patient's dose will be established for the maintenance period. Patients will continue to receive their maintenance dose over the next 5 weeks, although dose reductions for adverse events are allowed. Patients will return to the clinic at weeks 9 and 12 for assessments of safety and efficacy. At week 12, patients will undergo a complete evaluation, including safety and efficacy measures.

Washout Period. All patients will discontinue study drug at the week 12 visit and will return 1 week later for evaluation of safety and tic reduction (week 13).

Dose regimen. As discussed above, study drug will be administered as oral tablets at a starting dose of 6 mg once daily and titrated. Tablets of deutetrabenazine will be available in the following dose strengths: 6, 9, 12, 15, and 18 mg, distinguishable by imprint and color. Instruction will be provided to ensure that: the starting dose of 6 mg in all patients will be administered in the evening on days 1 and 2, followed by AM administration for the remainder of week 1 (if body weight is <40 kg); study drug should be swallowed whole and taken with food; subsequent daily doses of 12 mg and higher will be administered twice daily in 2 divided doses, approximately 8 to 10 hours apart during the day; a minimum of 6 hours should elapse between doses; if a patient misses a dose, and it is within 6 hours of the next dose, the missed dose should be skipped; if patients experience insomnia while taking the initial 6-mg dose in the evening, they may switch to taking it as a morning dose for 2 days; after week 1, dose increases should not occur more frequently than every 5 days; and dose reductions, if required, should be in increments of 6 mg.

Blinding and Randomization. Patients will be randomly assigned to receive treatment with deutetrabenazine or matching placebo in a 1:1 ratio.

Expected Results. It is expected that administration of a tolerable amount of deutetrabenazine, between 6 and 48 mg, in the above study in Tourette syndrome patients will: reduce total tic severity, both motor and phonic/vocal tics, impairment, and/or global severity scores, improve quality of life, overall life satisfaction, and/or patient or clinical global impression of change, and improve (lengthen) tic-free interval. It is expected that safety will be consistent with what has been observed in previous studies.

Long-Term Open-Label Phase 3 Study of Safety and Efficacy in TS Patients

Purpose. The primary objective of this study is to evaluate the safety and tolerability of long-term therapy with deutetrabenazine; the secondary objective is to evaluate efficacy.

Study Design. The study will include male and female patients with a tic associated with Tourette syndrome (TS) who have previously completed participation in either of the above clinical studies of deutetrabenazine.

Screening. Informed consent/assent will be obtained before any study procedures are performed. Patients who have been off study drug for several months at the time of enrollment, and who are stable from a medical and psychiatric standpoint, will undergo a screening evaluation as described above in the randomized study. To reduce patient burden, some data collected in the randomized study above will be used to provide corresponding data in this open label study. Patients may be rescreened at the discretion of the medical monitor. Inclusion and exclusion criteria will be similar to those discussed above for the randomized trial, with the exception that participation in either of the trials above is an inclusion, and not an exclusion, criterion, and that data regarding disqualifying DSM-V diagnoses may be obtained from the screening visit of the randomized study.

Baseline visit. For patients enrolled in the randomized study above, the baseline visit will occur simultaneously with the week 13 visit of that study. Week 13 assessments specified for that are also specified for the baseline visit of that study need not be repeated. For all patients, the baseline visit will occur on the same day as the scheduled first dose of the study drug (day 1). For patients with clinically significant laboratory abnormalities at week 12 in the randomized study above, the week 13 value will serve as baseline in this study. Rollover for such patients must be approved by the medical monitor and may be delayed.

Titration Period (7 weeks). As patients from the pilot study will have been off study drug for several months at the time of enrollment, and since patients from the randomized study will have discontinued study drug or placebo for 1 week, all patients will undergo dose titration in this study. Patients will receive 6 mg of deutetrabenazine with food on the evening of day 1.

Maintenance Period (47 weeks). At the end of the titration period, the patient's initial dose for the maintenance period will be established. Dose adjustments of deutetrabenazine (upward or downward) may be made during the maintenance period, if necessary, but not more often than every 5 days and only in increments of 6 mg. Dose adjustments should be made based on all available information, including the patient and caregiver/adult reports of adverse events and tic reduction, the clinical assessment of safety and efficacy by the investigator, the patient's weight and CYP2D6 medication status, and information from the rating scales. During the maintenance period, in-person (in-clinic) study visits will be scheduled at weeks 8, 15, 28, 41, and 54 for assessments of safety and efficacy. At week 54, patients will undergo a complete evaluation as above in the randomized trial.

Washout and follow-up. All patients will discontinue study drug at the week 54 visit and will return 1 week later (week 55) for evaluation of safety and tic reduction. Patients will have a follow-up telephone contact for safety evaluation 1 week after the end of the washout period (2 weeks after their last dose of study drug [week 56]).

Dose regimen. Study drug will be administered as above for the randomized trial.

Study Endpoints. Safety endpoints will be as above in the randomized study. Efficacy endpoints will include the Primary and Secondary Efficacy Endpoints as above in the randomized study, with a goal of reducing severity of motor and phonic/vocal tics. Exploratory endpoints be as above in the randomized study, from baseline to each visit.

Expected Results. It is expected that administration of a tolerable amount of deutetrabenazine, between 6 and 48 mg, in the above study in Tourette syndrome patients will: reduce total tic severity, both motor and phonic/vocal tics, impairment, and/or global severity scores, improve quality of life, overall life satisfaction, and/or patient global impression of severity or clinical global impression of change, and improve (lengthen) tic-free interval. It is expected that safety will be consistent with what has been observed in previous studies.

QT Prolongation

Drug-drug interactions in the treatment of patients with HD and other disorders involving abnormal involuntary movement may also be a serious concern. Depression is a common comorbidity in HD and patients are often treated with selective serotonin reuptake inhibitors (SSRIs), including citalopram and escitalopram, that have a risk for QT prolongation. Additionally, owing to frequent behavioral abnormalities, several studies indicated that patients with HD often receive treatment with antipsychotics (one-quarter up to two-thirds of patients of HD have received antipsychotics. Antipsychotics are known to prolong the QT interval. According to FDA guidance, prolongation of the QT interval can favor the development of cardiac arrhythmias, such as torsade de pointes, which can degenerate into ventricular fibrillation and lead to death. Per the United States prescribing information, tetrabenazine should not be used in conjunction with agents known to prolong the QT interval.

Study Design. Given the known risk for tetrabenazine to increase the QT interval, a TQT study of deutetrabenazine, which included tetrabenazine as a treatment arm, was conducted in 48 healthy volunteers. This was a single-center, randomized, double-blind, placebo- and positive-controlled six-period crossover study to evaluate the effects of low-dose (12 mg) and high-dose (24 mg) deutetrabenazine on cardiac repolarization, based on placebo-corrected, time-matched changes from baseline in the QTcF interval. Assay sensitivity was established by using moxifloxacin 400 mg as the positive control.

The key outcome measure was to determine the effect of single doses of deutetrabenazine on the QTc interval. A 50 mg dose of tetrabenazine was selected as this was the maximal dose employed in the TQT study for tetrabenazine and resulted in the Warning and Precaution in the product label. A 24-mg dose of deutetrabenazine was selected as it provides comparable systemic exposure (AUC) to 50 mg of tetrabenazine, but with a lower peak concentration (Cmax).

Results. For deutetrabenazine, 12-mg and 24-mg doses led to placebo-corrected time-matched maximal increases in QTc of 2.8 ms and 4.5 ms, respectively. For deutetrabenazine, the placebo-corrected change from baseline in QTcF and the upper bound of the two-sided 90% confidence interval was below the threshold of regulatory concern (5 ms) for both dose levels. In contrast, the maximum time-matched, placebo-adjusted change from baseline in QTcF for tetrabenazine 50 mg was 7.6 ms, consistent with the tetrabenazine prescribing information. Results are given below in Table 25.

TABLE 25

Maximum Placebo-Adjusted Change from Baseline in QTcF with deutetrabenazine and Tetrabenazine

| Parameter | DTBZ 12 mg | DTBZ 24 mg | Tetra-benazine 50 mg | Moxifloxacin 400 mg |
|---|---|---|---|---|
| Placebo-Adjusted Change from Baseline (ms) | 2.8 | 4.5 | 7.6 | 14.0 |
| 90% 2-sided Confidence Interval | (0.7, 4.8) | (2.4, 6.5) | (5.6, 9.5) | (11.9, 16.0) |

In the table above, AAQTcF is defined as the difference between the least squares mean change from baseline for the active drug and placebo. deutetrabenazine was compared with deutetrabenazine placebo (administered under fed conditions) and tetrabenazine was compared with tetrabenazine placebo (administered under fasted conditions). The maximal AAQTcF was observed at the 8-hour time point for deutetrabenazine and the 3-hour time point for tetrabenazine. The upper limit of the 95% one-sided confidence interval is the upper limit of the 90% 2-sided confidence interval.

Conclusion. These results support the fact that the differentiated pharmacokinetic profile and lower Cmax associated with deutetrabenazine compared with tetrabenazine improves the safety profile of deutetrabenazine by reducing the risk for life-threatening arrhythmias.

From the foregoing description, one skilled in the art can ascertain the essential characteristics of this invention, and without departing from the spirit and scope thereof, can make various changes and modifications of the invention to adapt it to various usages and conditions.

What is claimed is:

1. A method of transitioning a human from tetrabenazine to deutetrabenazine for the treatment of chorea associated with Huntington's disease, comprising:
    a) discontinuing a daily amount of tetrabenazine; and
    b) administering an initial daily amount of deutetrabenazine the next day to the human,
        wherein the daily amount of tetrabenazine is 12.5 mg and the initial total daily amount of deutetrabenazine is 6 mg; or
        wherein the daily amount of tetrabenazine is 25 mg and the initial total daily amount of deutetrabenazine is 12 mg; or
        wherein the daily amount of tetrabenazine is 37.5 mg and the initial total daily amount of deutetrabenazine is 18 mg; or
        wherein the daily amount of tetrabenazine is 50 mg and the initial total daily amount of deutetrabenazine is 24 mg; or
        wherein the daily amount of tetrabenazine is 62.5 mg and the initial total daily amount of deutetrabenazine is 30 mg; or
        wherein the daily amount of tetrabenazine is 75 mg and the initial total daily amount of deutetrabenazine is 36 mg; or
        wherein the daily amount of tetrabenazine is 87.5 mg and the initial total daily amount of deutetrabenazine is 42 mg; or
        wherein the daily amount of tetrabenazine is 100 mg and the initial total daily amount of deutetrabenazine is 48 mg.

2. The method of claim 1, wherein the transitioning results in the chorea control is improved by a reduction of at least 0.5 points on the Total Maximal Chorea (TMC) score.

3. The method of claim 2, wherein the improvement is measured from a pre-treatment, baseline to maintenance therapy.

4. The method of claim 1, wherein the transitioning results in a reduction of chorea by at least 15%.

5. The method of claim 1, wherein:
    (i) the transitioning results in a reduction of chorea by at least 10% and said method also provides at least one of the following:
        motor function is improved by at least 10%;
        the human's physical functioning is improved;
        swallowing is improved;
        balance is not worsened;
        treatment causes no significant increase in insomnia, depression, anxiety, agitation, suicidal ideation, akathisia, irritability, fatigue, parkinsonism or dysphagia;
        the maximal increases in QTcF is less than 5 ms;
        or combinations thereof; or
    (ii) motor function is improved by at least 10%, and said method also provides at least one of the following:
        chorea is reduced by at least 10%;
        the human's physical functioning is improved;
        swallowing is improved;
        balance is not worsened;

treatment causes no significant increase in insomnia, depression, anxiety, agitation, suicidal ideation, akathisia, irritability, fatigue, parkinsonism or dysphagia;

the maximal increases in QTcF is less than 5 ms;

or combinations thereof.

6. The method of claim 1, wherein the initial daily amount is 12 mg, 18 mg, 24 mg, 30 mg, 36 mg, 42 mg, or 48 mg and the initial daily amount is administered in two doses.

7. The method of claim 6, wherein:
the first dose is 6 mg and the second dose is 6 mg;
the first dose is 9 mg and the second dose is 9 mg;
the first dose is 12 mg and the second dose is 12 mg;
the first dose is 15 mg and the second dose is 15 mg;
the first dose is 18 mg and the second dose is 18 mg;
the first dose is 21 mg and the second dose is 21 mg; or
the first dose is 24 mg and the second dose is 24 mg.

8. The method of claim 7, further comprising:
c) after about one week, determining the degree of control of abnormal involuntary movement achieved with the initial daily amount of the deutetrabenazine and the tolerability of the initial daily amount of the deutetrabenazine; and
d) increasing the daily amount of the deutetrabenazine upward by 6 mg/day to a subsequent daily amount of the deutetrabenazine if the transitioning does not result in at least a maintenance of chorea control and the initial daily amount is tolerable.

9. The method of claim 8, further comprising:
e) after about one week, repeating steps c) and d) in those humans wherein abnormal involuntary movement is reduced and the daily amount of deutetrabenazine is tolerated.

10. The method of claim 9,
decreasing the amount of deutetrabenazine by 6 mg/day to a subsequent daily amount in those humans wherein any subsequent daily amount is not tolerated.

11. The method of claim 9, further comprising repeating step e) until the degree of control of abnormal involuntary movement is adequate and the daily amount of deutetrabenazine is tolerable.

12. The method of claim 1, wherein the initial daily amount is 6 mg and is administered in one dose.

13. The method of claim 1, wherein the initial daily amount of deutetrabenazine is 6 mg, 12 mg, 18 mg, 24 mg, 30 mg, 36 mg, or 42 mg, further comprising:
c) after about one week, determining the degree of control of abnormal involuntary movement achieved with the initial daily amount of the deutetrabenazine and the tolerability of the initial daily amount of the deutetrabenazine; and
d) increasing the daily amount of the deutetrabenazine by 6 mg/day to a subsequent daily amount in those humans wherein the transitioning does not result in at least a maintenance of chorea control and the initial daily amount is tolerable.

14. The method of claim 13, wherein the subsequent daily amount is 12 mg, 18 mg, 24 mg, 30 mg, 36 mg, or 42 mg, further comprising:
e) after about one week, repeating steps c) and d) in those patients wherein abnormal involuntary movement is reduced and the daily amount of deutetrabenazine is tolerated.

15. The method of claim 14, wherein the daily amount is 18 mg, 24 mg, 30 mg, 36 mg, or 42 mg, further comprising repeating step e) until the degree of control of abnormal involuntary movement is adequate and the daily amount of deutetrabenazine is tolerable.

16. The method of claim 15, wherein the total maximum daily dose is 48 mg.

17. The method of claim 15, where in the total maximum daily dose is 36 mg.

18. The method of claim 17, wherein the human is concurrently receiving a strong CYP2D6 inhibitor.

19. The method of claim 18, wherein the strong CYP2D6 inhibitor is fluoxetine, paroxetine, bupropion, quinidine, cinacalcet, or ritonavir.

20. The method of claim 19, wherein the strong CYP2D6 inhibitor is paroxetine, fluoxetine, or bupropion.

21. The method of claim 1, wherein the daily amount of tetrabenazine is 12.5 mg and the initial total daily amount of deutetrabenazine is 6 mg.

22. The method of claim 1, wherein the daily amount of tetrabenazine is 25 mg and the initial total daily amount of deutetrabenazine is 12 mg.

23. The method of claim 22, wherein the initial total daily amount of deutetrabenazine is administered in two doses, wherein the first dose is 6 mg and the second dose is 6 mg.

24. The method of claim 1, wherein the daily amount of tetrabenazine is 37.5 mg and the initial total daily amount of deutetrabenazine is 18 mg.

25. The method of claim 22, wherein the initial total daily amount of deutetrabenazine is administered in two doses, wherein the first dose is 9 mg and the second dose is 9 mg.

26. The method of claim 1, wherein the daily amount of tetrabenazine is 50 mg and the initial total daily amount of deutetrabenazine is 24 mg.

27. The method of claim 22, wherein the initial total daily amount of deutetrabenazine is administered in two doses, wherein the first dose is 12 mg and the second dose is 12 mg.

28. The method of claim 1, wherein the daily amount of tetrabenazine is 62.5 mg and the initial total daily amount of deutetrabenazine is 30 mg.

29. The method of claim 22, wherein the initial total daily amount of deutetrabenazine is administered in two doses, wherein the first dose is 15 mg and the second dose is 15 mg.

30. The method of claim 1, wherein the daily amount of tetrabenazine is 75 mg and the initial total daily amount of deutetrabenazine is 36 mg.

31. The method of claim 22, wherein the initial total daily amount of deutetrabenazine is administered in two doses, wherein the first dose is 18 mg and the second dose is 18 mg.

32. The method of claim 1, wherein the daily amount of tetrabenazine is 87.5 mg and the initial total daily amount of deutetrabenazine is 42 mg.

33. The method of claim 22, wherein the initial total daily amount of deutetrabenazine is administered in two doses, wherein the first dose is 21 mg and the second dose is 21 mg.

34. The method of claim 1, wherein the daily amount of tetrabenazine is 100 mg and the initial total daily amount of deutetrabenazine is 48 mg.

35. The method of claim 22, wherein the initial total daily amount of deutetrabenazine is administered in two doses, wherein the first dose is 24 mg and the second dose is 24 mg.

36. The method of claim 1, wherein the transitioning results in at least a maintenance of chorea control in the human.

37. The method of claim 1, wherein the initial total daily amount of deutetrabenazine is 6 mg, 12 mg, 18 mg, 24 mg, 30 mg, or 36 mg.

38. The method of claim 37, wherein the human is concurrently receiving a strong CYP2D6 inhibitor.

39. The method of claim 38, wherein the strong CYP2D6 inhibitor is fluoxetine, paroxetine, bupropion, quinidine, cinacalcet, or ritonavir.

40. The method of claim 38, wherein the strong CYP2D6 inhibitor is paroxetine, fluoxetine, or bupropion.

* * * * *

UNITED STATES PATENT AND TRADEMARK OFFICE
CERTIFICATE OF CORRECTION

PATENT NO. : 10,959,996 B2  
APPLICATION NO. : 16/040012  
DATED : March 30, 2021  
INVENTOR(S) : Stamler et al.

Page 1 of 1

It is certified that error appears in the above-identified patent and that said Letters Patent is hereby corrected as shown below:

In the Claims

At Column 94, Line 27 (Claim 25), delete "claim 22" and substitute therefor -- claim 24 --

At Column 94, Line 33 (Claim 27), delete "claim 22" and substitute therefor -- claim 26 --

At Column 94, Line 39 (Claim 29), delete "claim 22" and substitute therefor -- claim 28 --

At Column 94, Line 45 (Claim 31), delete "claim 22" and substitute therefor -- claim 30 --

At Column 94, Line 51 (Claim 33), delete "claim 22" and substitute therefor -- claim 32 --

At Column 94, Line 57 (Claim 35), delete "claim 22" and substitute therefor -- claim 34 --

Signed and Sealed this  
Seventeenth Day of August, 2021

Drew Hirshfeld  
*Performing the Functions and Duties of the*  
*Under Secretary of Commerce for Intellectual Property and*  
*Director of the United States Patent and Trademark Office*